(12) United States Patent
Samuels et al.

(10) Patent No.: US 8,795,964 B2
(45) Date of Patent: Aug. 5, 2014

(54) GRM3 MUTATIONS AND USE THEREOF FOR THE DIAGNOSIS AND TREATMENT OF MELANOMA

(75) Inventors: Yardena R. Samuels, Rehovot (IL); Todd D. Prickett, Sterling, VA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/825,713

(22) PCT Filed: Sep. 16, 2011

(86) PCT No.: PCT/US2011/052032
§ 371 (c)(1), (2), (4) Date: Mar. 22, 2013

(87) PCT Pub. No.: WO2012/040065
PCT Pub. Date: Mar. 29, 2012

(65) Prior Publication Data
US 2013/0190374 A1    Jul. 25, 2013

Related U.S. Application Data

(60) Provisional application No. 61/385,925, filed on Sep. 23, 2010.

(51) Int. Cl.
*C12Q 1/68* (2006.01)

(52) U.S. Cl.
USPC .......................................................... 435/6.1

(58) Field of Classification Search
CPC .................................. C12Q 1/68; A61K 39/00
See application file for complete search history.

(56) References Cited

U.S. PATENT DOCUMENTS

| | | |
|---|---|---|
| 6,485,919 B1 | 11/2002 | Daggett et al. |
| 2006/0134109 A1 | 6/2006 | Gaitanaris et al. |
| 2006/0147923 A1 | 7/2006 | Daggett et al. |

FOREIGN PATENT DOCUMENTS

| | | |
|---|---|---|
| WO | WO 01/96350 | 12/2001 |
| WO | WO 2004/024936 | 3/2004 |

OTHER PUBLICATIONS

Tockman et al (Cancer Res., 1992, 52:2711s-2718s).*
Ciceroni et al., "Type-3 metabotropic glutamate receptors negatively modulate bone morphogenetic protein receptor signaling and support the tumourigenic potential of glioma-initiating cells," *Neuropharmacology* vol. 55(4):568-576, 2008.
Kan et al., "Diverse somatic mutation patterns and pathway alterations in human cancers," *Nature* vol. 466(7308):869-873, 2010.
Prickett et al., "Exon capture analysis of G protein-coupled receptors identifies activating mutations in GRM3 in melanoma," Vol. *Nat Genet* 43(11):1119-1126, 2012.
Shin et al., "Metabotropic Glutamate Receptors (mGluRs) and Cellular Transformation," *Neuropharmacology*, vol. 55(4):396-402, 2008.

* cited by examiner

*Primary Examiner* — Sean Aeder
(74) *Attorney, Agent, or Firm* — Klarquist Sparkman, LLP

(57) ABSTRACT

Described herein is a G-protein coupled receptor (GPCR)-directed mutational analysis of tumor DNA obtained from melanoma tissue samples. The GPCR gene glutamate receptor, metabotropic 3 (GRM3) was identified as the most highly mutated GPCR gene in this screen. Functional characterization of GRM3 mutants revealed that these mutants promote activation of MEK, anchorage-independent cell growth and metastasis. Thus, provided herein are methods of diagnosing a subject as having melanoma, or susceptible to developing melanoma, by detecting the presence of at least one mutation in GRM3. Also provided are methods of treating a subject with melanoma by detecting the presence of at least one mutation in GRM3 and administering an appropriate therapy. Further provided are methods of selecting a subject diagnosed with melanoma as a candidate for treatment with a GRM3 inhibitor, an MEK inhibitor, or both, by detecting the presence of at least one mutation in GRM3.

20 Claims, 22 Drawing Sheets

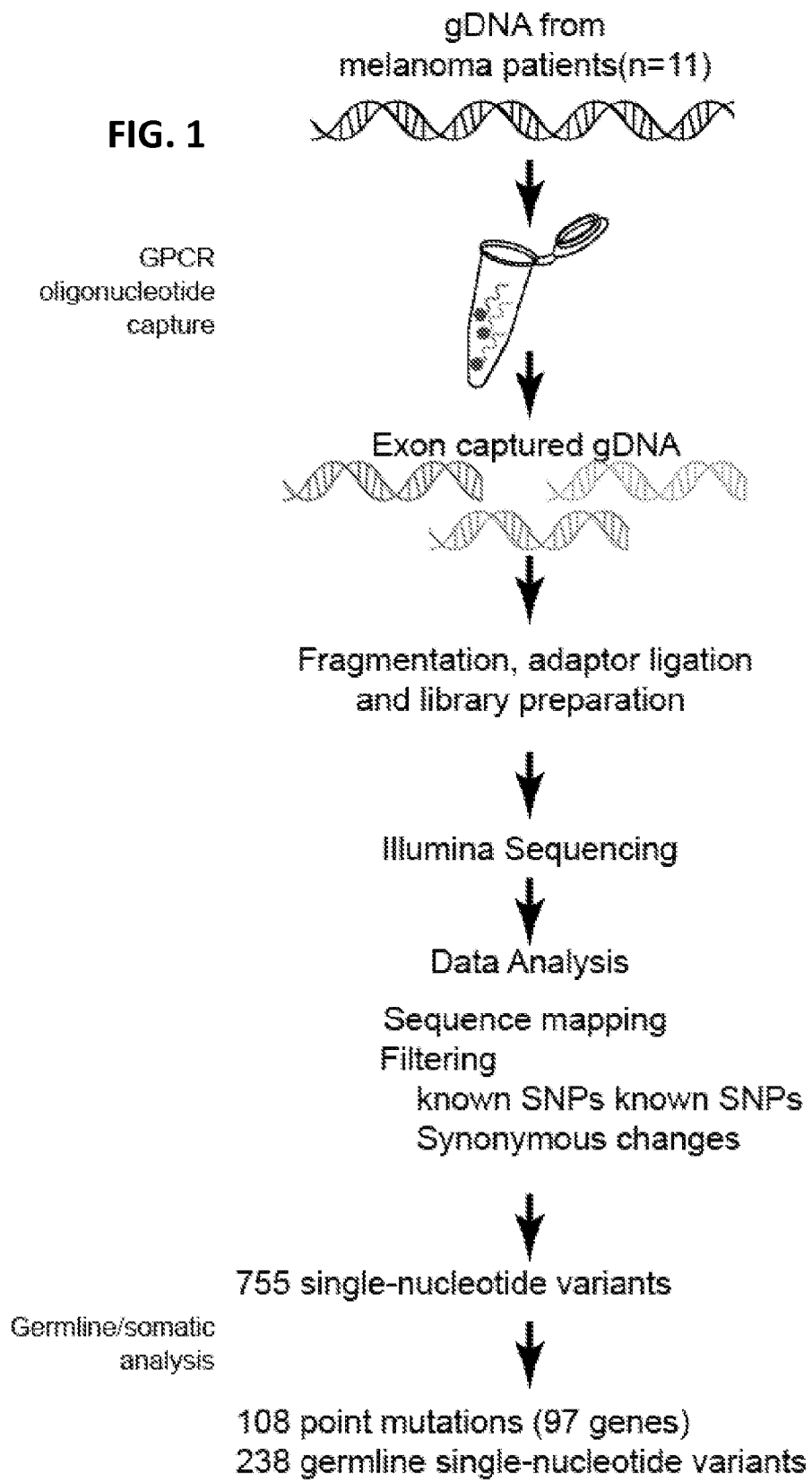

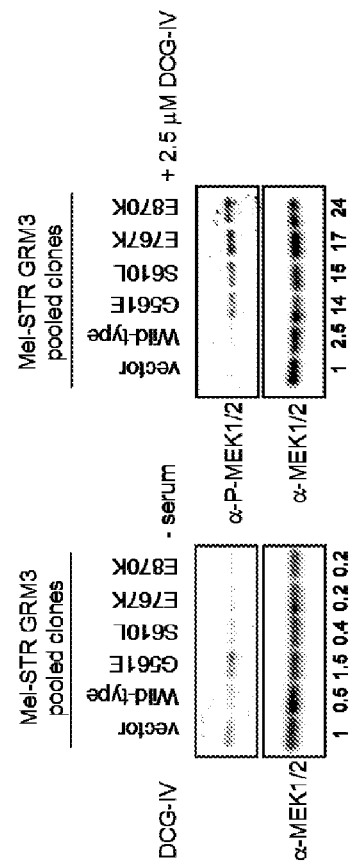
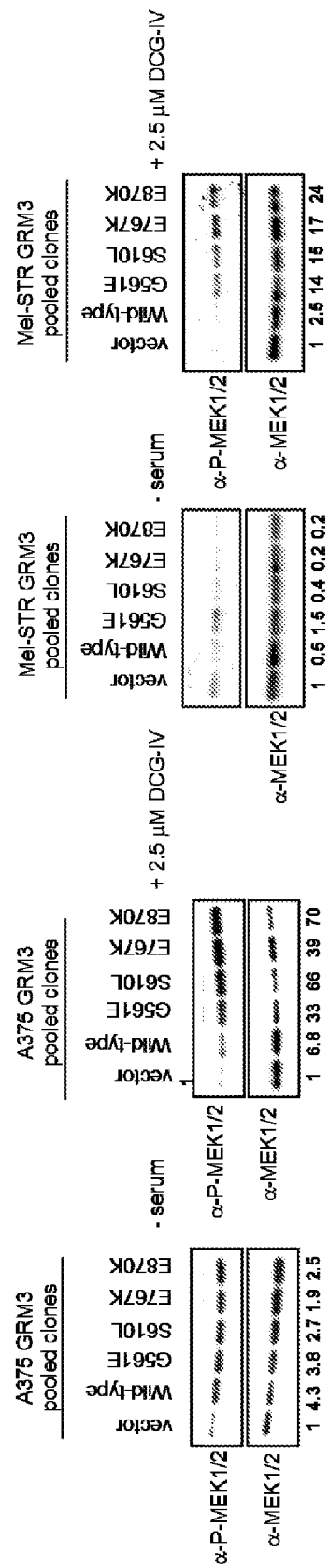
FIG. 2C
FIG. 2D

FIG. 3B
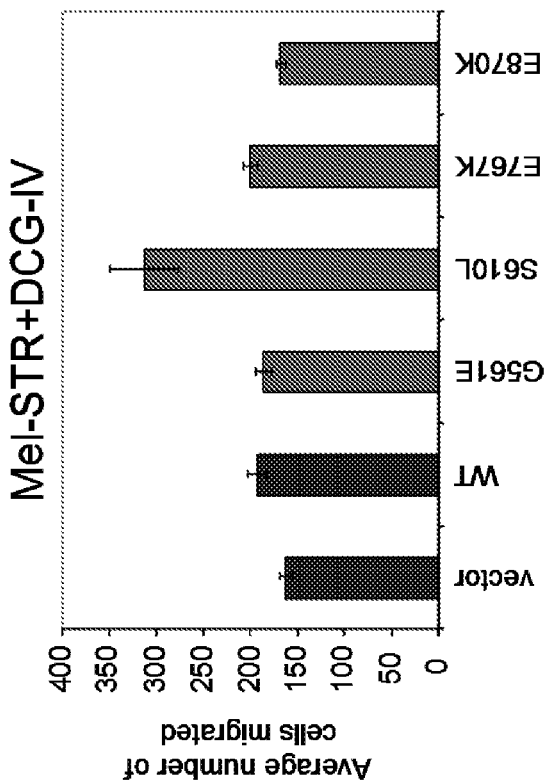
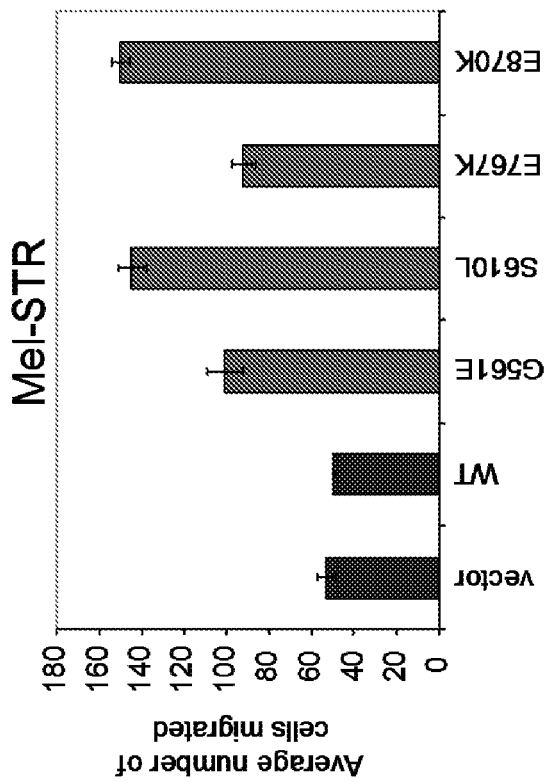

FIG. 4A
Ai
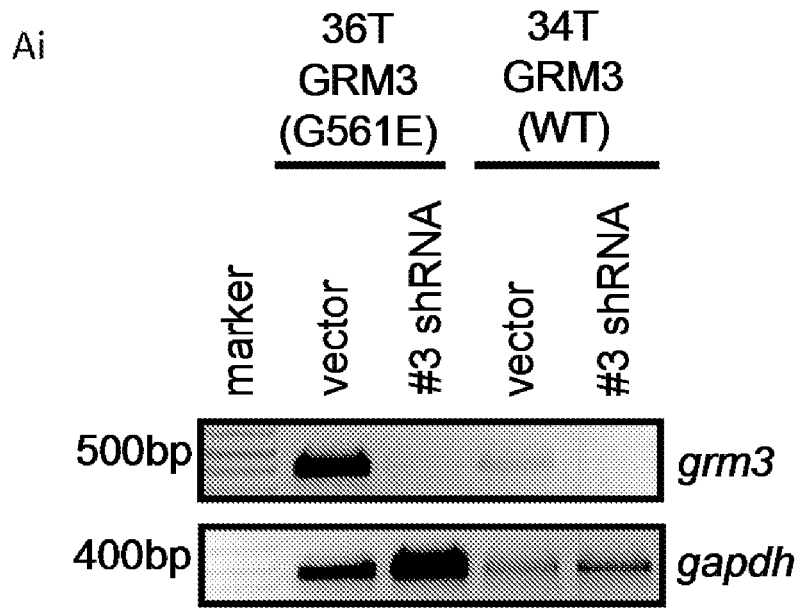
Aii
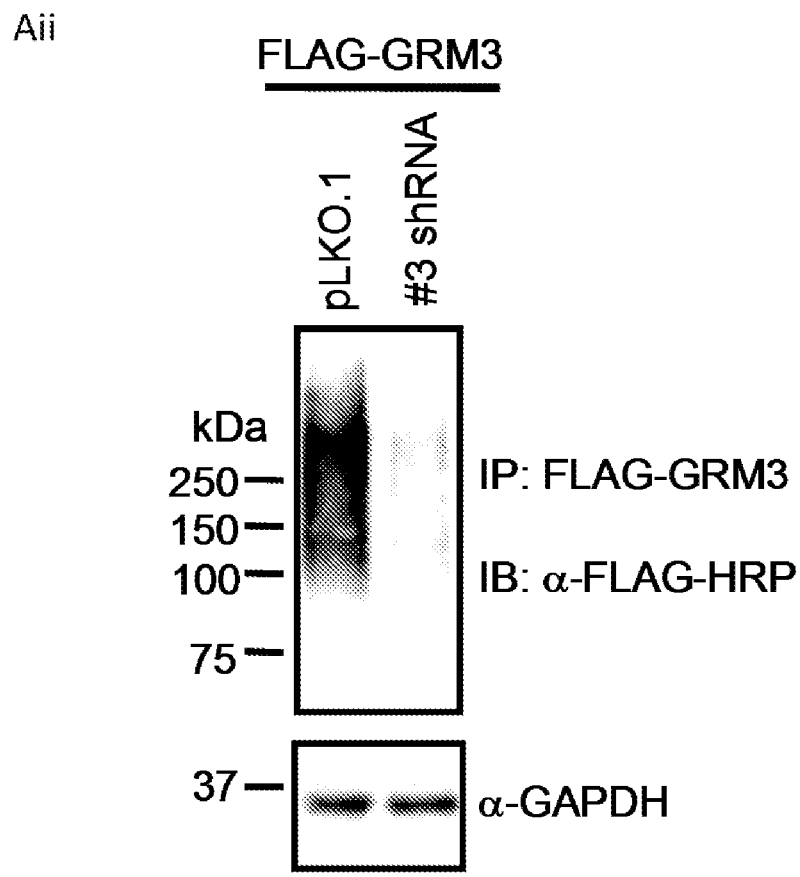

FIG. 4B
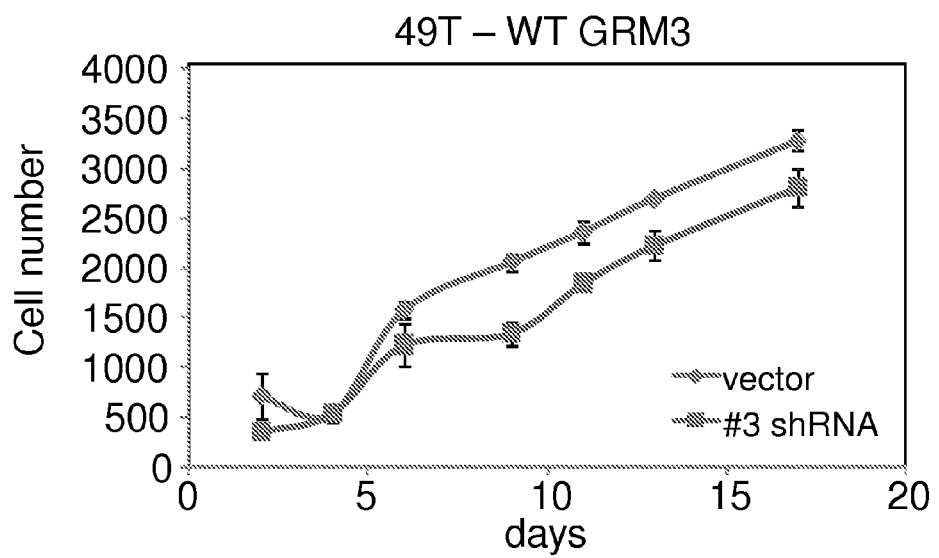
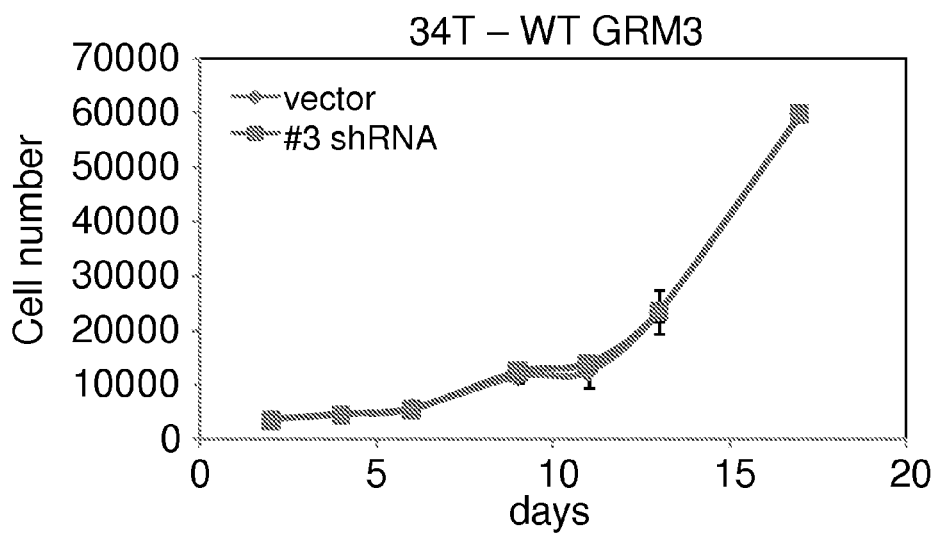

FIG. 4C (Page 1 of 2)
Biii
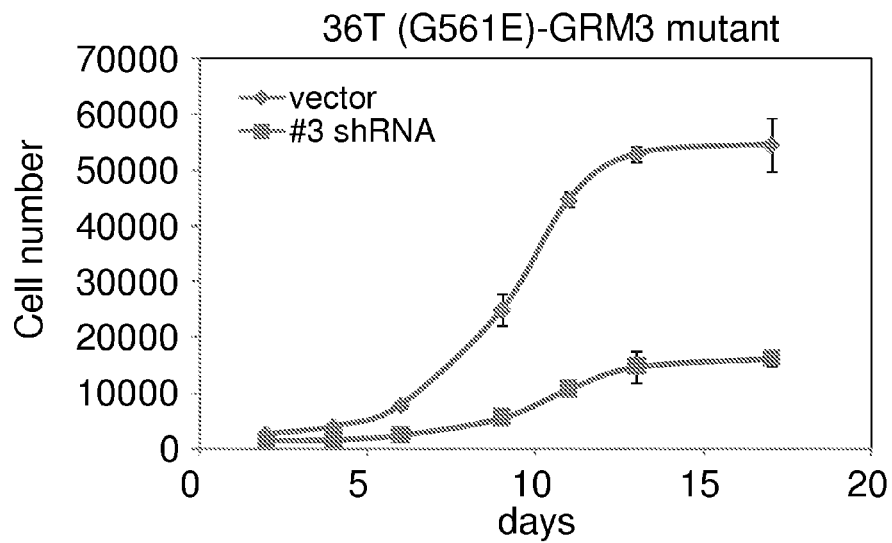
Biv
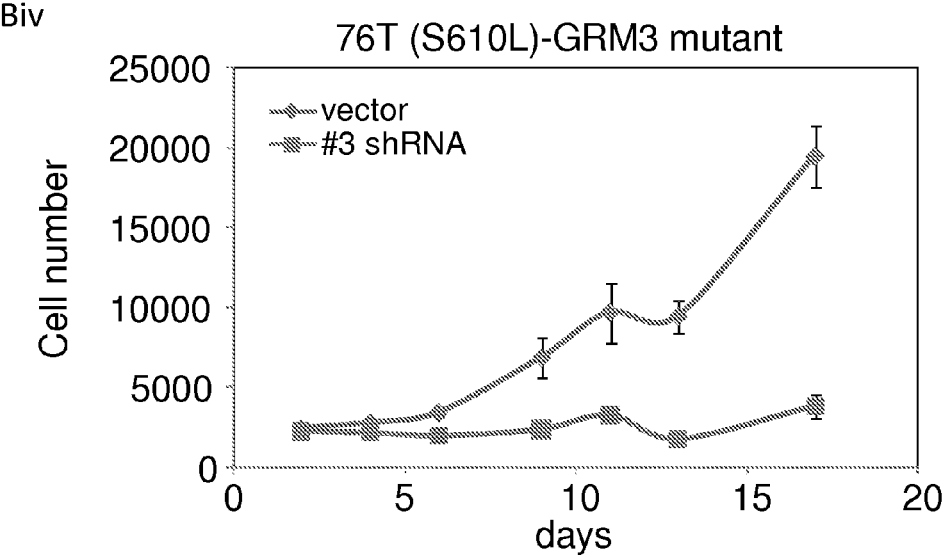

FIG. 4C (Page 2 of 2)
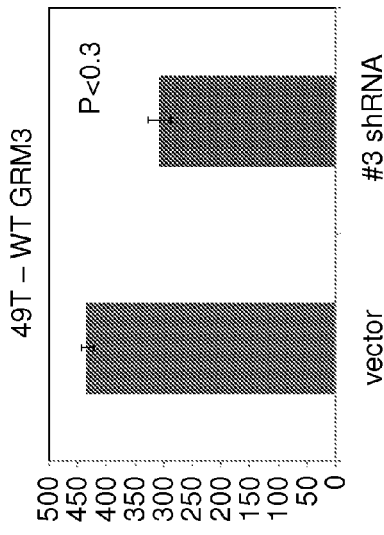
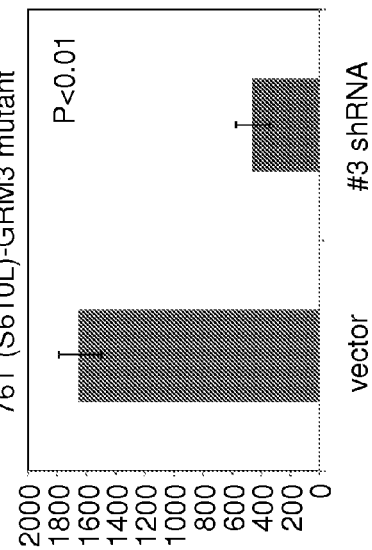
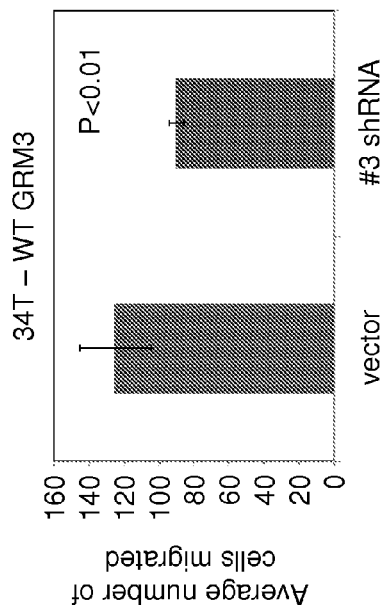
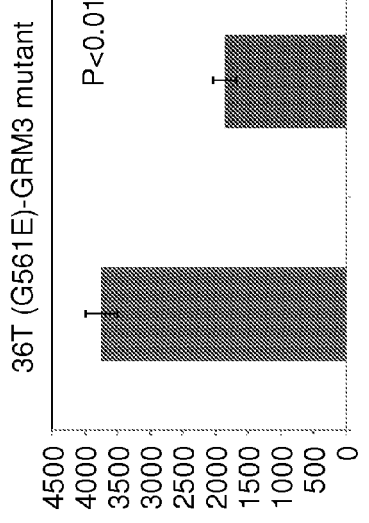

| Tumor line | EC50 (nM)* | sem |
| --- | --- | --- |
| 68T (Ser154Phe/Asp280Asn/Arg352Trp/Glu870Lys) | 128 | 131 |
| 63T (Glu573Lys) | 179 | 95 |
| 29T (Splice site) | 226 | 100 |
| 36T (Gly561Glu) | 1075 | 145 |
| 55T (WT) | 13,357 | 156 |
| 76T (Gly88Glu/Ser610Leu) | 15219 | 205 |
| 39T (Glu517Lys) | >30,000 | >500 |
| 71T (WT) | >30,000 | 478 |
| 49T (WT) | >30,001 | >500 |
| 13T (WT) | >30,000 | >500 |

*EC50 values for cell growth inhibition by AZD-6244 of melanoma cell lines harboring WT or mutant GRM3

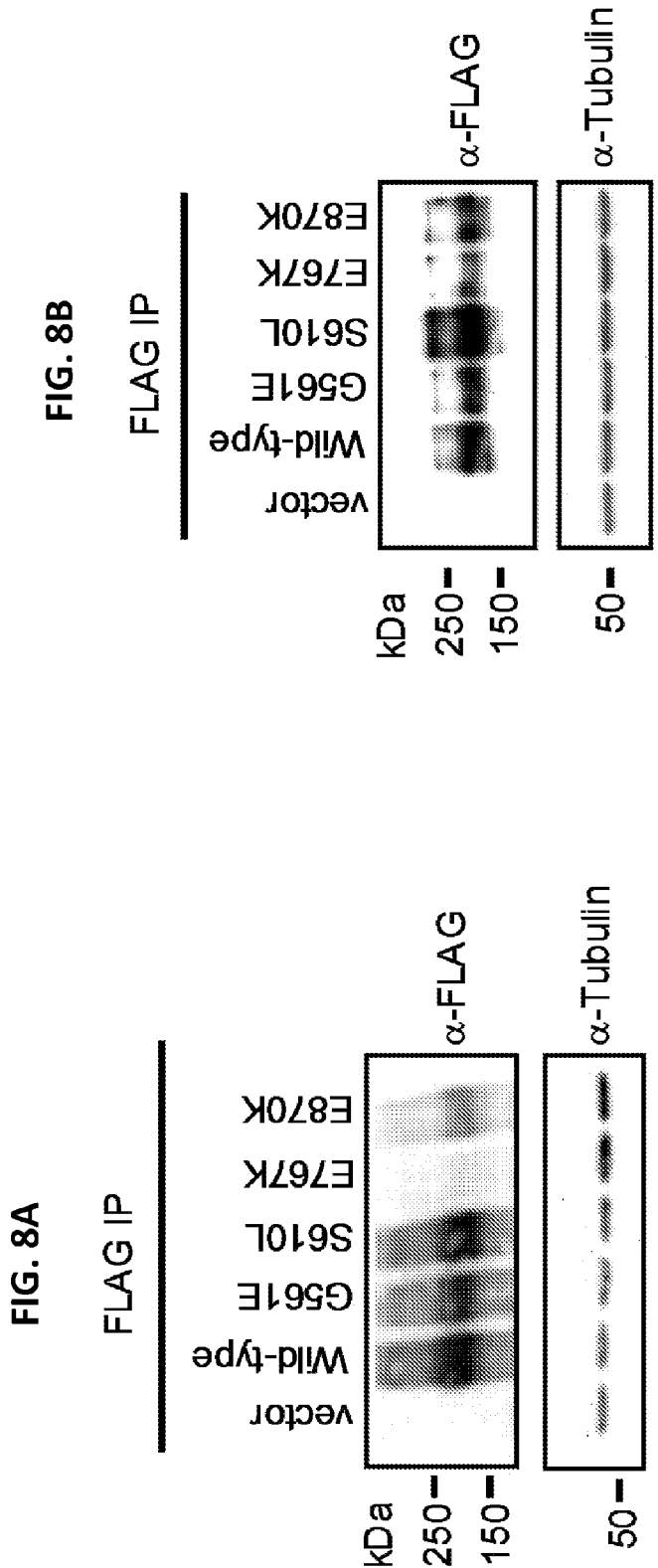

FIG. 12C

| Tumor cell line | EC50 (nM) | sem |
|---|---|---|
| 13T (WT) | >30,000 | 350 |
| 63T (Glu573Lys) + pLK0.1 | 109 | 10 |
| 63T (Glu573Lys) + WT GRM3 | 427 | 13 | ns entirety.

GRM3 MUTATIONS AND USE THEREOF FOR THE DIAGNOSIS AND TREATMENT OF MELANOMA

CROSS REFERENCE TO RELATED APPLICATIONS

This is the U.S. National Stage of International Application No. PCT/US2011/052032, filed Sep. 16, 2011, published in English under PCT Article 21(2), which claims the benefit of U.S. Provisional Application No. 61/385,925, filed Sep. 23, 2010, which is herein incorporated by reference in its entirety.

FIELD

This disclosure concerns diagnostic markers for melanoma. In particular, this disclosure concerns identification of mutations in glutamate receptor, metabotropic 3 (GRM3), and their use for the diagnosis and treatment of melanoma.

BACKGROUND

G-protein coupled receptors (GPCRs) are encoded by the largest superfamily of genes in the mammalian genome (Marinissen and Gutkind, *Trends Pharmacol Sci* 22:368-376, 2001). GPCRs play an integral part in regulating physiological functions such as neurotransmission, and release of hormones and enzymes involved in signaling and immune responses (Dorsam and Gutkind, *Nat Rev Cancer* 7:79-94, 2007; Lee et al., *Pigment Cell Melanoma Res* 21:415-428, 2008). These receptors are activated by a variety of ligands, such as hormones and growth factors. The important role these molecules play in many human diseases is evident by the fact that 50-60% of the current FDA approved therapeutics target GPCRs or their direct downstream signaling components (Flower, *Biochim Biophys Acta* 1422:207-234, 1999). As GPCRs are involved in the regulation of signal transduction pathways that are central to cell growth regulation, their genetic analysis in cancer is warranted.

Melanoma is the most common form of skin cancer. Despite years of research, metastatic melanoma disease has a dismal prognosis and is often fatal (Jemal et al., *CA Cancer J Clin* 59:225-249, 2009). There are few therapeutic options for melanoma patients, demonstrating a need for new clinically relevant targets. Thus, a systematic genetic analysis of genes involved in signal transduction such as the GPCRs that are important for cell survival, proliferation and migration is needed in order to identify novel therapeutic targets.

SUMMARY

It is disclosed herein that a number of GPCR genes are mutated in melanoma tumors. In particular, this disclosure identifies the GPCR gene GRM3 as a highly mutated gene in melanoma. It is demonstrated herein that mutations in GRM3 promote activation of MEK, increase anchorage-independent cell growth and migration, and promote metastasis.

Provided herein is a method of diagnosing a subject as having melanoma, or susceptible to developing melanoma, by detecting at least one mutation in the GRM3 gene. The presence of the at least one mutation indicates the subject has melanoma or is susceptible to developing melanoma. In some embodiments, the GRM3 mutation is selected from G1682A, C1829T, G2299A and G2608A (SEQ ID NO: 1). In other embodiments, the GRM3 mutation occurs in a portion of the GRM3 gene encoding the 7TM_3 domain (amino acid residues 580-833 of SEQ ID NO: 2). In particular examples, the GRM3 mutation is C1829T or G2299A (SEQ ID NO: 1).

In some embodiments, the method further includes providing an appropriate therapy to the subject.

Also provided is a method of selecting a subject diagnosed with melanoma as a candidate for treatment with a GRM3 inhibitor, an MEK inhibitor, or both, by detecting at least one mutation in the GRM3 gene of the subject. The presence of the at least one mutation in GRM3 identifies the subject as a candidate for treatment with a GRM3 inhibitor, an MEK inhibitor, or both. In some embodiments, the GRM3 mutation is selected from G1682A, C1829T, G2299A and G2608A (SEQ ID NO: 1). In other embodiments, the GRM3 mutation occurs in a portion of the GRM3 gene encoding the 7TM_3 domain (amino acid residues 580-833 of SEQ ID NO: 2). In particular examples, the GRM3 mutation is C1829T or G2299A (SEQ ID NO: 1).

The foregoing and other objects, features, and advantages of the invention will become more apparent from the following detailed description, which proceeds with reference to the accompanying figures.

BRIEF DESCRIPTION OF THE DRAWINGS

FIG. 1: Exome capture and next-generation sequencing analysis of the GPCR family identifies GRM3 mutations in melanoma. Shown is a schematic overview of the mutation identification approach of the GPCR gene family in a panel of tumor DNA samples from 11 melanoma patients using oligonucleotide sequence capture and next-generation sequencing with ILLUMINA™. After several analysis stages and validation in 80 melanoma samples, nine GPCR genes were found to be highly somatically mutated.

FIGS. 2A-2D: Effects of GRM3 mutations on cell growth and mitogen-activated protein kinase kinase (MEK) phosphorylation. (FIG. 2A) Somatic mutations in GRM3 cause increased proliferation in reduced serum. A375 pooled GRM3 clones expressing wild-type (WT), G561E, S610L, E767K or E870K GRM3, or vector alone, were seeded in 96-well plates in the presence of reduced serum (1% fetal bovine serum (FBS)). Plates were harvested and analyzed by SYBR™ Green I on a BMG Labtech Fluor Optima. (FIG. 2B) GRM3 mutants exhibit anchorage-independent growth. Mel-STR cells were seeded in a top plug of agar and allowed to incubate for 2 weeks prior to analysis by light microscopy and counting using ImageJ software. Student t-test for all showed a p<0.05 except for vector versus WT. (FIG. 2C) Mutant GRM3 activates MEK1/2 upon DCG-IV stimulation in A375. A375 pooled GRM3 clones seeded in 6-well dishes were serum starved for 4 hours prior to addition of either 2.5 µM DCG-IV or vehicle for 10 minutes. Upon lysis of cells, lysates were analyzed using SDS-PAGE gels and immunoblotting with corresponding antibodies. Ratios shown were generated by ImageJ/Microsoft Excel analysis of phosphoprotein/total protein blots. (FIG. 2D) Mutant GRM3 activates MEK1/2 upon DCG-IV stimulation in Mel-STR. Mel-STR pooled GRM3 clones were analyzed as described in FIG. 2C.

FIGS. 3A-3C: GRM3 mutations increase cell migration in vitro and in vivo. (FIG. 3A) A375 pooled GRM3 clones in the absence of stimulus (i) migrate as well as those stimulated with the group II metabotropic agonist DCG-IV (ii). A375 clones were seeded in Boyden chambers in either the absence of stimulus (i) or in the presence of 2.5 µM DCG-IV (ii) and assessed for their ability to migrate 16 hours later. (FIG. 3B) Mel-STR pooled GRM3 clones were analyzed for migration as described in (FIG. 3A). Stained wells were analyzed using a Zeiss microscope 10× lens and counted with NIH ImageJ software. (FIG. 3C) non-obese diabetic (NOD)/severe combined immunodeficiency (SCID) mice were intravenously injected with A375 pooled GRM3 clones expressing WT, G561E, S610L, E767K, or E870K GRM3, or vector alone, and examined after nine weeks. (i) Graph indicates the number of mice that had lung macrometastases. (ii) Representative images of lungs from mice injected with vector, WT or mutant expressing A375 clones.

FIGS. 4A-4C: Expression of mutant GRM3 provides cell proliferation and survival signals in melanoma. (FIG. 4A) RT-PCR and western blot analysis showed that expressing GRM3 short hairpin RNA (shRNA) decreases endogenous GRM3 compared with empty vector. (i) RT-PCR analysis of mutant GRM3 cell line (36T) and WT GRM3 cell line (34T) using GRM3 or gapdh specific primers. (ii) Immunoblots of melanoma cells transduced with shRNA targeting GRM3 and immunoprecipitated with anti-GRM3. For normalization, lysates were analyzed in parallel by anti-α-GAPDH immunoblotting. (FIG. 4B) Growth curves of representative melanoma cell lines transduced with shRNA control or shRNA targeting GRM3. (FIG. 4C) Stable knock-down of GRM3 in mutant GRM3 expressing cells causes decreased migration compared to WT expressing cells. Growth curves of representative melanoma cell lines transduced with shRNA control or shRNA targeting GRM3. WT GRM3 melanoma cell lines stably transduced (i-ii) with either empty vector of #3 shRNA (GRM3) or mutant GRM3 melanoma cell lines stably transduced (iii-iv) with either empty vector of #3 shRNA (GRM3) were seeded in Boyden chamber wells (triplicate) in serum-free medium (top chamber) and 10% serum (bottom chamber) and incubated for 16-72 hours prior to staining with HemaStat3 kit and analysis. Results were quantified using a Student's t-test (inset of graphs).

(FIG. 5A) Immunoblot analysis of representative melanoma cell lines harboring either WT or mutant GRM3. The cells were treated with the indicated concentration of AZD-6244 and analyzed for Erk1/2 expression and phosphorylation. Cells were treated for 1 hour with AZD-6244 or vehicle alone as control. Lysates were subjected to protein blot analysis with α-Eek, anti-P-Erk1/2 (α-P-Erk1/2) and anti-GAPDH as a loading control. (FIG. 5B) Representative dose-response curves showing efficacy of AZD-6244 against GRM3 mutant lines compared to WT GRM3 lines. Relative cell number after cells were treated for 72 hours with increasing concentrations (0.01-30 µM) of AZD-6244, as estimated by CellTiterGlo and plotted as percent survival, as compared to vehicle-treated control, versus log AZD-6244 concentration in nM (where 1 is 10 nM AZD-6244). Fitted lines were generated using four-parameter nonlinear regression. (FIG. 5C) $IC_{50}$ values for inhibition of cell growth by 72-hour treatment with AZD-6244 of a larger panel of lines harboring wild-type and mutant GRM3 (n=3). (FIG. 5D) fluorescence activated cells sorting (FACS) analysis of WT (2T) and A190V mutant (17T) cells showing cell cycle distribution (propidium iodide (PI) staining, x axis) versus cell counts (y axis). Shown are representative plots. (FIG. 5D) Quantification of FACS-sorted AZD-6244-treated cells. The percentage of apoptotic cells was determined based on the sub-G1 population for vehicle-treated cells or 1 AZD-6244 treated cells. (FIG. 5E) Immunoblot analysis of representative melanoma lines expressing WT or mutant GRM3 after AZD-6244 treatment using the indicated antibodies to assess poly-ADP ribose polymerase (PARP) cleavage.

(FIG. 6A) GPCR mutation spectrum. The number of each of the six classes of base substitutions resulting in nonsynonymous changes in the kinome screen is shown. (FIG. 6B) Mutation spectra of single base pair substitutions in GRM3. The number of each of the six classes of base substitutions resulting in nonsynonymous changes in GRM3 is shown.

(FIG. 7A) Representative examples of the hotspot mutation in GRM3. In each case, the top sequence chromatogram was obtained from normal tissue and the lower sequence chromatogram from the indicated tumors. Arrows indicate the location of missense mutations. The nucleotide and amino acid alterations are indicated below the chromatograms. (FIG. 7B) Black arrows indicate positions of nonsynonymous mutations and boxes represent functional domains (PBP1_mGluR_groupII: Receptor family ligand binding region; NCD3G: 9 cysteines domain of family 3 GPCR; 7TM_3: 7 transmembrane sweet-taste receptor of 3 GPCR).

FIGS. 8A-8B: Stable expression of mutant GRM3 in melanoma cell lines reduces cellular dependence on serum. Stable pooled GRM3 clones show equivalent expression in two different melanoma cell lines. A375 pooled GRM3 clones (FIG. 8A) or Mel-STR pooled GRM3 clones (FIG. 8B) were analyzed for FLAG-GRM3 expression by immunoprecipitation with FLAG-M2 beads and subsequently immunoblotted on SDS-PAGE gels with anti-FLAG-HRP. Lysates were immunoblotted using anti-tubulin as a loading control.

(FIG. 10A) The graph indicates the number of mice that had lung micrometastases. (FIG. 10B) Lung micrometastases volume measurements from mice injected with empty vector or mutant GRM3 show similar levels of metastatic tumor area.

(FIG. 11A) HEK293T cells were transfected with control or GRM3 shRNA #3 and either WT or non-targetable (NT) GRM3 and analyzed by immunoblotting of lysates with anti-FLAG-HRP. As a loading control, lysates were immunoblotted with α-GAPDH. (FIG. 11B) Melanoma cells expressing vector or the GRM3 shRNA #3 transduced with a vector (vec) or NT GRM3 were evaluated for cell migration in Boyden chamber wells. Wells were stained with HemaStat3 kit and results quantitated using a Student's t-test (* p<0.001 compared to vec/vec and vec/NT; **p<0.05 compared to shRNA #3/vec) with the Microsoft Excel program.

FIGS. 12A-12C: Expression of WT GRM3 in a mutant GRM3 background desensitizes cells to AZD-6244 inhibition. (FIG. 12A) Cell lysates from 63T cells transduced with empty vector or WT GRM3 were analyzed by western blotting using anti-FLAG-HRP and anti-GAPDH as a loading control. (FIG. 12B) Melanoma cells harboring WT (13T) or mutant GRM3 (63T-Glu573Lys) transduced with empty vector or WT GRM3 were tested for growth inhibition by AZD-6244. Cells were plated and treated with AZD-6244 concentrations ranging from 2 nM to 30 μM for 72 hours prior to analysis using CellTiterGlo and GraphPad Prism5. $EC_{50}$ dose-response curves were generated from GraphPad using four-parameter nonlinear regression. (FIG. 12C) $EC_{50}$ values for inhibition of cell growth by 72 h treatment with AZD-6244 of the indicated melanoma cell lines.

SEQUENCE LISTING

Figure 2B:
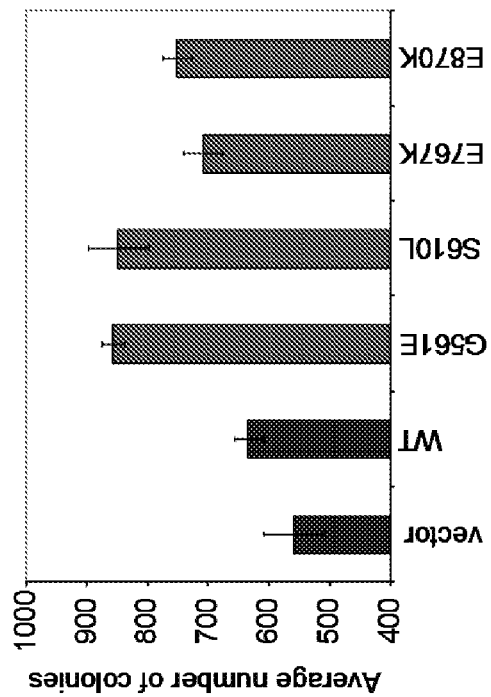

The nucleic acid and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Feb. 17, 2014, 25.5 KB, which is incorporated by reference herein. In the accompanying sequence listing:

SEQ ID NO: 1 is the nucleotide sequence of human GRM3 (CCDS Accession No. 5600.1).

SEQ ID NO: 2 is the amino acid sequence of human GRM3 (GenBank Accession No. NM_8000840, as it appears in the database on Sep. 14, 2010).

SEQ ID NOs: 3 and 4 are the nucleotide sequences of RT-PCR primers for amplification of GRM3.

SEQ ID NOs: 5 and 6 are the nucleotide sequences of RT-PCR primers for amplification of GAPDH.

SEQ ID NOs: 7-16 are the nucleotide sequences of primers used for the construction of the GRM3 gene.

SEQ ID NOs: 17-21 are the nucleotide sequences of GRM3 shRNAs.

SEQ ID NOs: 22-45 are the nucleotide sequences of PCR primers for amplification of the GRM3 gene.

SEQ ID NO: 46 is the nucleotide sequence of the GRM3 sh639 shRNA.

SEQ ID NO: 47 is the nucleotide sequence of the GRM3 sh742 shRNA.

SEQ ID NO: 48 is the nucleotide sequence of human GRM3 (GenBank Accession No. NM_000840, as it appears in the database on Sep. 14, 2010).

DETAILED DESCRIPTION

I. Abbreviations dbSNP single nucleotide polymorphism database
DNA deoxyribonucleic acid
ELISA enzyme-linked immunosorbent assay
FACS fluorescence activated cell sorting
FBS fetal bovine serum
GAPDH glyceraldehyde-3-phosphate dehydrogenase
GPCR G-protein coupled receptor
GRM3 glutamate receptor, metabotropic 3
H&E hematoxylin and eosin
HRP horseradish peroxidase
MEK mitogen-activated protein kinase kinase
MIP molecular inversion probes
mRNA messenger ribonucleic acid
NOD non-obese diabetic
NS non-synonymous
NT non-targetable
PARP poly-ADP ribose polymerase
PCR polymerase chain reaction
RNA ribonucleic acid
RT-PCR reverse transcriptase polymerase chain reaction
SCID severe combined immunodeficiency SDS-PAGE sodium dodecyl sulfate polyacrylamide gel electrophoresis
shRNA short hairpin RNA
WT wild-type II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least two, at least four, at least six, to at least 9, at least 10, at least 14, at least 15, at least 20, at least 30, at least 50, at least 75, at least 100, at least 150, at least 200, at least 300, at least 500, least 550, at least 600, at least 800, at least 1000, or more. In a particular example, an array includes 2-100 addressable locations, such as 4-20 addressable locations. In particular examples, an array consists essentially of oligonucleotide probes specific for the somatic mutations in GRM3 disclosed herein. In other examples, the array consists essentially of oligonucleotide probes specific for the somatic mutations in one or more the GPCR genes disclosed herein.

In particular examples, an array includes nucleic acid molecules, such as oligonucleotide sequences that are at least 15 nucleotides in length, such as about 15-40 nucleotides in length.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Clinical outcome: Refers to the health status of a patient following treatment for a disease or disorder (such as melanoma), or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Decrease in survival: As used herein, "decrease in survival" refers to a decrease in the length of time before death of a patient, or an increase in the risk of death for the patient. A decrease in survival also can refer to a decrease in the average time to death in a group, such as a group of patients diagnosed with melanoma.

Diagnosing: Refers to the process of identifying the nature or cause of a disease or disorder.

Genomic DNA: The DNA found within the nucleus and containing an organism's genome, which is passed on to its offspring as information for continued replication and/or propagation and/or survival of the organism. The term can be used to distinguish between other types of DNA, such as DNA found within plasmids or organelles.

Glutamate receptor, metabotropic 3 (GRM3): The metabotropic glutamate receptors are a family of G protein-coupled receptors that have been divided into 3 groups on the basis of sequence homology, putative signal transduction mechanisms, and pharmacologic properties. Group I includes GRM1 and GRM5 and these receptors have been shown to activate phospholipase C. Group II includes GRM2 and GRM3, and Group III includes GRM4, GRM6, GRM7 and GRM8. Group II and III receptors are linked to the inhibition of the cyclic AMP cascade but differ in their agonist selectivity. L-glutamate is the major excitatory neurotransmitter in the central nervous system and activates both ionotropic and metabotropic glutamate receptors. Glutamatergic neurotransmission is involved in most aspects of normal brain function and can be perturbed in many neuropathologic conditions. GRM3 is also known as GLUR3; mGlu3; GPRC1C; and MGLUR3.

Disclosed herein are somatic mutations in GRM3 identified in melanoma tissue samples. The disclosed somatic mutations are referred to by the location of the GRM3 mutation with reference to SEQ ID NO: 1 (nucleotide) and SEQ ID NO: 2 (amino acid). For example, the G1682A mutation refers to a guanine to adenine substitution at nucleotide 1682 (SEQ ID NO: 1), which results in a glycine (G) to glutamic acid (E) change at amino acid 561 (SEQ ID NO: 2). As another example, the T/C (−13) mutation refers to an thymidine to cytosine change in an intron, which results in mutation of a splice site. In some embodiments of the methods disclosed herein, the GRM3 mutation occurs in a portion of the GRM3 gene encoding the 7TM_3 domain. As defined herein, the 7TM_3 domain is encoded by nucleotides 2837-3598 of human GRM3 (SEQ ID NO: 21) and the amino acid sequence of the 7TM_3 domain is set forth herein as residues 580-833 of SEQ ID NO: 2.

Inhibitor: As used herein, an "inhibitor" refers to any compound that is capable of reducing or altering the expression or activity of a target molecule. In some embodiments, the inhibitor is an inhibitor GRM3. In some embodiments, the inhibitor is an MEK inhibitor. In particular examples, the MEK inhibitor is AZD-6244.

Label: An agent capable of detection, for example by enzyme-linked immunosorbent assay (ELISA), spectrophotometry, flow cytometry or microscopy. For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

In some embodiments, the label is a fluorophore ("fluorescent label"). Fluorophores are chemical compounds, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540λ. Red fluorophores, for example Texas Red, Cy5 and tetramethylrhodamine, are characterized by their emission at wavelengths generally in the range of 590-690λ.

Examples of fluorophores that may be used are provided in U.S. Pat. No. 5,866,366 to Nazarenko et al., and include for instance: 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other contemplated fluorophores include GFP (green fluorescent protein), Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

Melanoma: A form of cancer that originates in melanocytes (cells that make the pigment melanin). Melanocytes are found primarily in the skin, but are also present in the bowel and eye. As used herein, "melanoma" refers to any stage of melanoma, or any subtype of melanoma, such as superficial spreading melanoma, nodular melanoma, acral lentiginous melanoma, lentigo maligna, melanoma-in-situ, mucosal melanoma and uveal melanoma.

Metastasis: Refers to the spread of cancer cells from the original tumor to other sites in the body.

Mutation: Any change of the DNA sequence within a gene or chromosome. In some instances, a mutation will alter a characteristic or trait (phenotype), but this is not always the case. Types of mutations include base substitution point mutations (e.g., transitions or transversions), deletions and insertions. M is sense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells (such as cancer cells), but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with "polymorphism," as discussed below, but generally refers to the subset of constitutional alterations that have arisen within the past few generations in a kindred and that are not widely disseminated in a population group.

In some embodiments, a mutation in GRM3 refers to a nucleotide substitution in the GRM3 gene or cDNA, or an amino acid substitution in the GRM3 protein.

Oligonucleotide: A linear polynucleotide sequence of up to about 100 nucleotide bases in length. In some embodiments, the oligonucleotide is 15-40 nucleotides in length.

Patient: As used herein, the term "patient" includes human and non-human animals. The preferred patient for treatment is a human.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymorphism: Variant in a sequence of a gene, or any genomic sequence, usually carried from one generation to another in a population. Polymorphisms can be those variations (nucleotide sequence differences) that, while having a different nucleotide sequence, produce functionally equivalent gene products, such as those variations generally found between individuals, different ethnic groups, and geographic locations. The term polymorphism also encompasses variations that produce gene products with altered function, i.e., variants in the gene sequence that lead to gene products that are not functionally equivalent. This term also encompasses variations that produce no gene product, an inactive gene product, a truncated gene product, or increased or increased activity gene product.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (e.g., an alteration of a secondary structure such as a stem-loop, or an alteration of the binding affinity of the nucleic acid for associated molecules, such as polymerases, RNAses, a change in the availability of a site for cleavage by a restriction endonuclease, either the formation of a new site, or lose of a site, and so forth).

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown in the following table.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |

-continued

| Original Residue | Conservative Substitutions |
| --- | --- |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease (such as metastatic melanoma) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Probes and primers: A probe comprises an isolated nucleic acid capable of hybridizing to a target nucleic acid. A detectable label or reporter molecule can be attached to a probe or primer. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example in Sambrook et al. (In *Molecular Cloning: A Laboratory Manual*, CSHL, New York, 1989) and Ausubel et al. (In *Current Protocols in Molecular Biology*, John Wiley & Sons, New York, 1998). In some embodiments, an "oligonucleotide" is a probe or primer.

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 15 nucleotides in length, such as at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, or more contiguous nucleotides complementary to the target nucleic acid molecule, such as 15-70 nucleotides, 15-60 nucleotides, 15-50 nucleotides, 15-40 nucleotides, or 15-30 nucleotides.

Primers are short nucleic acid molecules, for instance DNA oligonucleotides 15 nucleotides or more in length, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50, 55, 60, 65, 70 or more consecutive nucleotides. In particular examples, a primer is at least 15 nucleotides in length, such as at least 15 contiguous nucleotides complementary to a target nucleic acid molecule. Particular lengths of primers that can be used to practice the methods of the present disclosure include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, or more contiguous nucleotides complementary to the target nucleic acid molecule to be amplified, such as a primer of 15-70 nucleotides, 15-60 nucleotides, 15-50 nucleotides, 15-40 nucleotides or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and primers can be readily prepared based on the nucleic acid molecules provided herein. It is also appropriate to generate probes and primers based on fragments or portions of these disclosed nucleic acid molecules, for instance regions that encompass the identified mutations of interest. PCR primer pairs can be derived from a known sequence by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Prognosis: The likelihood of the clinical outcome for a subject afflicted with a specific disease or disorder. With regard to cancer, the prognosis is a representation of the likelihood (probability) that the subject will survive (such as for one, two, three, four or five years) and/or the likelihood (probability) that the tumor will metastasize. A "poor prognosis" indicates a greater than 50% chance that the subject will not survive to a specified time point (such as one, two, three, four or five years), and/or a greater than 50% chance that the tumor will metastasize. In several examples, a poor prognosis indicates that there is a greater than 60%, 70%, 80%, or 90% chance that the subject will not survive and/or a greater than 60%, 70%, 80% or 90% chance that the tumor will metastasize. Conversely, a "good prognosis" indicates a greater than 50% chance that the subject will survive to a specified time point (such as one, two, three, four or five years), and/or a greater than 50% chance that the tumor will not metastasize. In several examples, a good prognosis indicates that there is a greater than 60%, 70%, 80%, or 90% chance that the subject will survive and/or a greater than 60%, 70%, 80% or 90% chance that the tumor will not metastasize.

Sample: A biological specimen containing genomic DNA, RNA, protein, or combinations thereof, obtained from a subject. Examples include, but are not limited to, peripheral blood, urine, saliva, tissue biopsy (such as skin tissue), surgical specimen, and autopsy material. In one example, a sample includes a biopsy of a melanoma tumor or a sample of normal tissue, such as skin tissue (from a subject not afflicted with a known disease or disorder, such as a cancer-free subject).

Specific hybridization: Specific hybridization refers to the binding, duplexing, or hybridizing of a molecule only or substantially only to a particular nucleotide sequence when that sequence is present in a complex mixture (e.g. total cellular DNA or RNA). Specific hybridization may also occur under conditions of varying stringency.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (In: *Molecular Cloning: A Laboratory Manual*, Cold Spring Harbor, N.Y., 1989 ch. 9 and 11). By way of illustration only, a hybridization experiment may be performed by hybridization of a DNA molecule to a target DNA molecule which has been electrophoresed in an agarose gel and transferred to a nitrocellulose membrane by Southern blotting (Southern, *J. Mol. Biol.* 98:503, 1975), a technique well known in the art and described in Sambrook et al. (*Molecular Cloning: A Laboratory Manual*, Cold Spring Harbor, N.Y., 1989).

Stringent conditions may be defined as those under which DNA molecules with more than 25%, 15%, 10%, 6% or 2% sequence variation (also termed "mismatch") will not hybridize. Stringent conditions are sequence dependent and are different in different circumstances. Longer sequences hybridize specifically at higher temperatures. Generally, stringent conditions are selected to be about 5° C. lower than the thermal melting point $T_m$ for the specific sequence at a defined ionic strength and pH. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na Phosphate, 5 mM EDTA, pH 7.4) and a temperature of 25-30° C. are suitable for allele-specific probe hybridizations.

The following is an exemplary set of hybridization conditions and is not meant to be limiting:

Very High Stringency (Detects Sequences that Share 90% Identity)
 Hybridization: 5×SSC at 65° C. for 16 hours
 Wash twice: 2×SSC at room temperature (RT) for 15 minutes each
 Wash twice: 0.5×SSC at 65° C. for 20 minutes each High Stringency (Detects Sequences that Share 80% Identity or Greater)
 Hybridization: 5×-6×SSC at 65° C.-70° C. for 16-20 hours
 Wash twice: 2×SSC at RT for 5-20 minutes each
 Wash twice: 1×SSC at 55° C.-70° C. for 30 minutes each Low Stringency (Detects Sequences that Share Greater than 50% Identity)
 Hybridization: 6×SSC at RT to 55° C. for 16-20 hours
 Wash at least twice: 2×-3×SSC at RT to 55° C. for 20-30 minutes each.

A perfectly matched probe has a sequence perfectly complementary to a particular target sequence. The test probe is typically perfectly complementary to a portion (subsequence) of the target sequence. The term "mismatch probe" refers to probes whose sequence is deliberately selected not to be perfectly complementary to a particular target sequence.

Somatic mutation: An acquired mutation that occurs in a somatic cell (as opposed to a germ cell).

Subject: Living multi-cellular vertebrate organisms, a category that includes both human and non-human mammals. In some embodiments, the subject is a human subject.

Therapeutic agent: A chemical compound, small molecule, or other composition, such as an antisense compound, antibody, peptide or nucleic acid molecule capable of inducing a desired therapeutic or prophylactic effect when properly administered to a subject. For example, therapeutic agents for melanoma include agents that prevent or inhibit development or metastasis of melanoma. In some embodiments, the therapeutic agent is an inhibitor of GRM3 or an inhibitor of MEK.

Therapy: The mode of treatment or care of a patient. In some cases, therapy refers to administration of a therapeutic agent. In some embodiments herein, therapy includes administration of an MEK inhibitor or a GRM3 inhibitor. In other examples, therapy includes surgery, such as surgical resection of a melanoma tumor, chemotherapy, radiation therapy, or any combination thereof.

Tumor, neoplasia, malignancy or cancer: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

G protein-coupled receptors (GPCRs), the largest human gene family, are known to be important regulators of signaling pathways. However, knowledge of their genetic alterations is limited. In the studies disclosed herein, exome capture and ILLUMINA™ sequencing methods were used to analyze the mutational status of all GPCRs in melanoma. This investigation revealed that one GPCR family member, GRM3, is frequently mutated in melanoma and that one nucleotide position of GRM3 is a mutational hotspot. Biochemical analysis of GRM3 alterations revealed that mutant GRM3 selectively regulated the phosphorylation of MEK leading to increased anchorage-independent growth and migration. Melanoma cells expressing mutant GRM3 exhibit reduced cell growth and cellular migration after shRNA-mediated knockdown of GRM3 or treatment with a selective MEK inhibitor, AZD-6244, which is currently being used in phase II clinical trials. The present disclosure provides a comprehensive map of genetic alterations in the GPCR gene family and identifies GRM3 as a potential target for therapy for melanoma patients.

IV. Overview of Several Embodiments

It is disclosed herein that a number of GPCR genes are mutated in melanoma tumors. In particular, this disclosure identifies GRM3 as highly mutated in melanoma. Functional characterization of the GRM3 mutations disclosed herein demonstrated that GRM3 mutations promote activation of MEK, increase anchorage-independent cell growth and migration, and promote metastasis.

Thus, provided herein is a method of diagnosing a subject as having melanoma, or susceptible to developing melanoma, by detecting at least one mutation in the GRM3 gene. The presence of the at least one mutation indicates the subject has melanoma or is susceptible to developing melanoma.

In some embodiments of the methods disclosed herein, the at least one mutation is selected from G1682A, C1829T, G2299A and G2608A (SEQ ID NO: 1). In other embodiments, the at least one mutation occurs in a portion of the GRM3 gene encoding the 7TM_3 domain (amino acid residues 580-833 of SEQ ID NO: 2). For example, the mutation in the region encoding the 7TM_3 domain can be C1829T or G2299A (SEQ ID NO: 1).

In one alternative embodiment, the at least one mutation in the GRM3 gene is a mutation in exon 3 or exon 5 of the GRM3 gene, such as G1402T, G1531A, G1549A, G1642A, G1682A, G1717A, C1829T, G2299A or G2608A (SEQ ID NO: 1; see Table 1). In particular examples, the mutation in exon 3 is G1682A, C1829T or G2299A. In a specific example, the mutation in exon 5 is G2608A. In another alternative embodiment, the mutation in the GRM3 gene occurs in a portion of the GRM3 gene encoding the PBP1_mGluRgroupII domain (amino acid residues 37 to 494 of SEQ ID NO: 2). In specific examples, the mutation that occurs in the PBP1_mGluRgroupII domain is selected from G176A, G263A, C461T, C575T, G838A, C1054T, T/C (−13) and G1402T (SEQ ID NO: 1). In another alternative embodiment, the mutation in the GRM3 gene occurs in a portion of the GRM3 gene encoding the NCD3G domain (amino acid residues 504-555 of SEQ ID NO: 2). In particular examples, the mutation that occurs in the NCD3G domain is selected from G1531A, G1549A and G1642A (SEQ ID NO: 1).

In some embodiments of the methods, detecting the presence or absence of the at least one mutation in GRM3 includes detecting the presence or absence of the mutation in a skin sample obtained from the subject.

In some embodiments, the method further includes providing a test output (i.e., the result of the test to detect mutations in GRM3) to a user (such as a physician or health care worker, the patient or laboratory personnel). In particular examples, the output includes the presence or absence of the at least one mutation, a diagnosis, a treatment recommendation, or any combination thereof.

In some embodiments, the method further includes administering an appropriate therapy to the subject. For example, the appropriate therapy can include surgery, radiation therapy, chemotherapy, administration of a GRM3 inhibitor, administration of an MEK inhibitor, or any combination of two or more thereof. In specific examples, the MEK inhibitor is AZD-6244.

Further provided herein is a method of selecting a subject diagnosed with melanoma as a candidate for treatment with a GRM3 inhibitor, an MEK inhibitor, or both, by detecting the presence or absence of at least one mutation in the GRM3 gene. The presence of the at least one mutation identifies the subject as a candidate for treatment with a GRM3 inhibitor, an MEK inhibitor, or both. In some embodiments, the at least one mutation is selected from G1682A, C1829T, G2299A and G2608A (SEQ ID NO: 1). In other embodiments, the at least one mutation occurs in a portion of the GRM3 gene encoding the 7TM_3 domain (amino acid residues 580-833 of SEQ ID NO: 2). In particular examples, the at least one mutation that occurs in a portion of the GRM3 gene encoding the 7TM_3 domain is C1829T or G2299A (SEQ ID NO: 1). In specific examples, the MEK inhibitor is AZD-6244.

In some embodiments, the method further includes providing a test output (i.e., the result of the test to detect mutations in GRM3) to a user (such as a physician or health care worker, the patient or laboratory personnel). In particular examples, the output includes the presence or absence of the at least one mutation, a diagnosis, a treatment recommendation, or any combination thereof.

Also provided herein is a method of treating a subject with melanoma by detecting at least one mutation in the GRM3 gene and administering an appropriate therapy to the subject. In some embodiments of the methods disclosed herein, the at least one mutation is selected from G1682A, C1829T, G2299A and G2608A (SEQ ID NO: 1). In other embodiments, the at least one mutation occurs in a portion of the GRM3 gene encoding the 7TM_3 domain (amino acid residues 580-833 of SEQ ID NO: 2). For example, the mutation in the region encoding the 7TM_3 domain can be C1829T or G2299A (SEQ ID NO: 1). In some embodiments, the appropriate therapy is administration of a GRM3 inhibitor, an MEK inhibitor, or both. In some examples, the therapy further includes surgery, chemotherapy, radiation therapy or any combination thereof.

Also provided herein is a method of predicting the prognosis of a subject diagnosed with melanoma by detecting the presence or absence of at least one mutation in the GRM3 gene. The presence of the at least one mutation indicates the subject has a poor prognosis. In some embodiments, the at least one mutation is selected from G1682A, C1829T, G2299A and G2608A (SEQ ID NO: 1). In other embodiments, the at least one mutation occurs in a portion of the GRM3 gene encoding the 7TM_3 domain (amino acid residues 580-833 of SEQ ID NO: 2). In particular examples, the at least one mutation that occurs in a portion of the GRM3 gene encoding the 7TM_3 domain is C1829T or G2299A (SEQ ID NO: 1).

A poor prognosis refers to any negative clinical outcome. For example, in some embodiments, a poor prognosis is an increase in the likelihood of death. In some embodiments, a poor prognosis is an increase in the likelihood of metastasis of the melanoma. The sample can be any appropriate sample from the patient, such as a tissue sample or bodily fluid sample. In particular examples, the sample is a melanoma tumor sample from the subject.

Further provided is a method of selecting a therapy for a subject diagnosed with melanoma by detecting the presence or absence of at least one mutation in the GRM3 gene. A GRM3 inhibitor or an MEK inhibitor is selected for therapy if the at least one mutation in GRM3 is present. In some embodiments, the at least one mutation is selected from G1682A, C1829T, G2299A and G2608A (SEQ ID NO: 1). In other embodiments, the at least one mutation occurs in a portion of the GRM3 gene encoding the 7TM_3 domain (amino acid residues 580-833 of SEQ ID NO: 2). In particular examples, the at least one mutation that occurs in a portion of the GRM3 gene encoding the 7TM_3 domain is C1829T or G2299A (SEQ ID NO: 1). In one non-limiting example, the MEK inhibitor is AZD-6244. In some embodiments, the therapy selected further includes surgery, chemotherapy, radiation therapy or any combination thereof. In some embodiments, the method of selecting an appropriate therapy for a subject further includes treating the subject with the appropriate therapy.

Although mutations in GRM3 for the diagnosis, prognosis and treatment of melanoma are exemplified herein, the present disclosure contemplates the use of mutations in any of the GPCR genes identified herein as mutated in melanoma (see Table 1 and Table 2 for a list of genes) in the provided methods. Thus, in some embodiments of the methods disclosed herein, the method includes detecting at least one mutation selected from any one of the mutations listed in Table 1 or Table 2.

For detection of GRM3 mutations (or mutations in any other GPCR gene), nucleic acid (such as DNA or RNA) can be isolated from a biological sample according to well-known methods. In some embodiments, the biological sample is a tissue sample, such as a skin sample or a tumor tissue sample. In other embodiments, the biological sample is a fluid sample, such as blood. For example, nucleic acid can be isolated from cells obtained from a blood sample. In some embodiments, the biological sample is obtained from a patient diagnosed with melanoma or at risk for developing melanoma. In some embodiments, the biological sample is obtained from a control subject.

Methods of detecting mutations in a gene are well known in the art. Detection of one or more mutations in the GRM3 gene (or any other GPCR gene) can be accomplished using any suitable technique, such as those described in detail below. For example, GRM3-specific primers can be used to amplify GRM3 nucleic acid from a biological sample (such as a skin sample, tumor tissue sample or blood sample). The amplified molecule can then be sequenced and compared to a reference GRM3 sequence (such as SEQ ID NO: 1). Alternatively, the sequence of the amplified molecule can be compared with GRM3 from a control sample such as a non-cancerous tissue sample. GRM3 amplification primers and sequencing primers can be designed according to well-known methods. Examples of GRM3 primers are shown in Table 6. Other suitable primers can be designed using publically available GRM3 nucleic acid sequences (including SEQ ID NO: 1), according to well-known procedures.

Mutations in GRM3 can also be detected using oligonucleotides that specifically hybridize with a particular mutation. Hybridization of such oligonucleotides can be detected by labeling the oligonucleotide with a detectable marker, such as a fluorescent marker, enzymatic marker or radioisotope. Appropriate output devices for obtaining nucleic acid sequence information or for detecting the presence of a fluorescent or radioactive signal are well known in the art.

Thus, provided herein is an oligonucleotide that specifically hybridizes with a mutant GRM3 nucleic acid molecule. In some embodiments, the GRM3 nucleic acid molecule comprises a mutation selected from G1682A, C1829T, G2299A and G2608A (SEQ ID NO: 1). The oligonucleotide can be any suitable length to allow for specific hybridization to a target nucleic acid molecule. In some embodiments, the oligonucleotide is about 12 to about 50, about 15 to about 40, about 18 to about 30 or about 20 to about 25 nucleotides in length. In particular examples, the oligonucleotide is about 15 to about 40 nucleotides in length. In some embodiments, the oligonucleotide includes a label, such as a fluorescent label, an enzymatic label or a radioisotope.

Further provided is an array including an oligonucleotide that specifically hybridizes with a mutant GRM3 nucleic acid molecule disclosed herein. In some embodiments, the array includes two or more oligonucleotides that specifically hybridize with a GRM3 nucleic acid comprising a mutation selected from G1682A, C1829T, G2299A and G2608A (SEQ ID NO: 1). In particular examples, the array is a microarray.

V. Methods of Detecting GRM3 Mutations

Methods of detecting mutations in GPCRs are known in the art and exemplary methods are described below. Although detection of GRM3 is exemplified herein, the techniques described can be applied to other genes and proteins, including other GPCRs disclosed herein (such as those listed in Table 1 and Table 2).

Detecting mutations in GRM3 can be accomplished using any technique known in the art. For example, the presence or absence of a GRM3 mutation can be determined by conventional methods such as gene or RNA detection methods (for example, DNA sequencing, oligonucleotide hybridization, polymerase chain reaction (PCR) amplification with primers specific to the mutation), or protein detection methods (for example, immunoassays or biochemical assays to identify a mutated GRM3 protein. Generally, the nucleic acid sequence of the GRM3 gene or RNA in a sample can be detected by any suitable method or technique of detecting gene sequence. Such methods include, but are not limited to, PCR, reverse transcriptase-PCR (RT-PCR), in situ PCR, in situ hybridization, Southern blot, Northern blot, sequence analysis, microarray analysis, or other DNA/RNA hybridization platforms.

Detection of point mutations in target nucleic acids can be accomplished by molecular cloning of the target nucleic acid molecules and sequencing the nucleic acid molecules using techniques well known in the art. Alternatively, amplification techniques such as PCR can be used to amplify target nucleic acid sequences directly from a genomic DNA preparation from a tumor tissue or cell sample. The nucleic acid sequence of the amplified molecules can then be determined to identify mutations. Representative primer pairs that can be used to amplify GRM3 nucleic acid from a biological sample are listed in Table 6. However, design and selection of appropriate primers is well within the abilities of one of ordinary skill in the art.

Ligase chain reaction (Wu et al., *Genomics* 4:560-569, 1989) and allele-specific PCR (Ruano and Kidd, *Nucleic Acids Res.* 17:8392, 1989) can also be used to amplify target nucleic acid sequences. Amplification by allele-specific PCR uses primers that hybridize at their 3' ends to a particular target nucleic acid mutation. If the particular mutation is not present, an amplification product is not observed. Amplification Refractory Mutation System can also be used to detect mutations in nucleic acid sequences (U.S. Pat. No. 5,595,890; Newton et al., *Nucleic Acids Res.* 17:2503-2516, 1989). Insertions and deletions of genes can also be detected by cloning, sequencing and amplification. In addition, restriction fragment length polymorphism probes for the gene or surrounding marker genes can be used to score alteration of an allele or an insertion in a polymorphic fragment. Single stranded conformation polymorphism analysis can also be used to detect base change variants of an allele (Orita et al., *Proc. Natl. Acad. Sci. USA* 86:2766-2770, 1989). Other known techniques for detecting insertions and deletions can also be used with the claimed methods.

Mismatch detection can be used to detect point mutations in a target nucleic acid molecule, such as GRM3. Mismatches are hybridized nucleic acid duplexes which are not 100% complementary. The lack of total complementarity can be due to deletions, insertions, inversions, substitutions or frameshift mutations. An example of a mismatch cleavage technique is the RNase protection method, which is described in detail in Winter et al. (*Proc. Natl. Acad. Sci. USA* 82:7575-7579, 1985) and Myers et al. (*Science* 230:1242-1246, 1985). For example, detection of mutations in GRM3 can involve the use of a labeled riboprobe that is complementary to wild-type GRM3. The riboprobe and nucleic acid molecule to be tested (for example, obtained from a tumor sample) are annealed (hybridized) together and subsequently digested with the enzyme RNase A, which is able to detect mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the target nucleic acid mRNA or gene, but can a portion of the target nucleic acid, provided it encompasses the position suspected of being mutated. If the riboprobe comprises only a segment of the target nucleic acid mRNA or gene, it may be desirable to use a number of these probes to screen the whole target nucleic acid sequence for mismatches if desired.

In a similar manner, DNA probes can be used to detect mismatches, for example through enzymatic or chemical cleavage (Cotton et al., *Proc. Natl. Acad. Sci. USA* 85: 4397, 1988; Shenk et al., *Proc. Natl. Acad. Sci. USA* 72:989, 1975). Alternatively, mismatches can be detected by shifts in the electrophoretic mobility of mismatched duplexes relative to matched duplexes (Cariello, *Human Genetics* 42:726, 1988). With riboprobes or DNA probes, the target nucleic acid mRNA or DNA which may contain a mutation can be amplified before hybridization. Changes in target nucleic acid DNA can also be detected using Southern hybridization, especially if the changes are gross rearrangements, such as deletions and insertions.

Amplified nucleic acid sequences can also be screened using allele-specific probes. These probes are nucleic acid oligomers, each of which contains a region of the target nucleic acid gene harboring a known mutation. For example, one oligomer may be about 30 nucleotides in length, corresponding to a portion of the target gene sequence. By use of a battery of such allele-specific probes, target nucleic acid amplification products can be screened to identify the presence of a previously identified mutation in the target gene. Hybridization of allele-specific probes with amplified target nucleic acid sequences can be performed, for example, on a nylon filter. Hybridization to a particular probe under stringent hybridization conditions indicates the presence of the same mutation in the tumor tissue as in the allele-specific probe.

GRM3 primers are useful for determination of the nucleotide sequence of a target nucleic acid molecule using nucleic acid amplification techniques such as the polymerase chain reaction. Pairs of single stranded DNA primers can be annealed to sequences within or surrounding the target nucleic acid sequence in order to prime amplification of the target sequence. Allele-specific primers can also be used. Such primers anneal only to particular mutant target sequence, and thus will only amplify a product in the presence of the mutant target sequence as a template. In order to facilitate subsequent cloning of amplified sequences, primers may have restriction enzyme site sequences appended to their ends. Such enzymes and sites are well known in the art. The primers themselves can be synthesized using techniques which are well known in the art. Generally, the primers can be made using oligonucleotide synthesizing machines which are commercially available. Design of particular primers is well within the skill of the art. In addition, exemplary GRM3 primers are provided in Table 6.

Nucleic acid probes that hybridize with a GRM3 nucleic acid molecule, such as a wild-type GRM3 nucleic acid molecule or a mutant GRM3 nucleic acid molecule described herein, are useful for a number of purposes. They can be used in Southern hybridization to genomic DNA and in RNase protection assays for detecting point mutations. The probes can also be used to detect target nucleic acid amplification products. GRM3 probes can also be used to detect mismatches with the wild type gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids (Novack et al., *Proc. Natl. Acad. Sci. USA* 83:586, 1986).

Mutations in nucleic acid molecules can also be detected by screening for alterations of the corresponding protein. For example, monoclonal antibodies immunoreactive with a target gene product can be used to screen a tissue, for example an antibody that is known to bind to a particular mutated position of the gene product (protein). For example, a suitable antibody may be one that binds to a deleted exon or that binds to a conformational epitope comprising a deleted portion of the target protein. Lack of cognate antigen would indicate a mutation. Such immunological assays can be accomplished using any convenient format known in the art, such as Western blot, immunohistochemical assay and ELISA. In some embodiments, the GRM3 amino acid mutation is selected from G561E, S610L, E767K and E870K (SEQ ID NO: 2).

Mutations in a gene or encoded protein can be evaluated using any technique described above, or any other method known in the art. For example, mutations in a gene or corresponding mRNA can be detecting by direct sequencing of a nucleic acid molecule, detection of an amplification product, microarray analysis or any other DNA/RNA hybridization platform. For detection of mutant proteins, an immunoassay, biochemical assay or microarray can be used.

Any suitable output device or format can be used to transmit the information obtained from the technique used to detect gene or protein mutations. For example, the output device can be a visual output device, such as a computer screen, a printed piece of paper or a written piece of paper. In other examples, the output device can be an auditory output device, such as a speaker. In other examples, the output device is a printer. In some cases, the data is recorded in a patient's electronic medical record. In some embodiments, the results of the test used to identify a mutation are provided to a user (such as a clinician or other health care worker, laboratory personnel, or patient) in a perceivable output that provides information about the results of the test. In some examples, the output is communicated to the user, for example by providing an output via physical, audible or electronic means (for example, by mail, telephone, facsimile transmission, e-mail or communication to an electronic medical record).

In some examples, the output is accompanied by guidelines for interpreting the data, for example, an indication of the likelihood of diagnosis of melanoma. The guidelines need not specify whether melanoma is present or absent, although it may include such a diagnosis. In other examples, the output can provide a recommended therapeutic regimen. For instance, based on the presence of a mutation in the GRM3 gene, the output can recommend treatment with a GRM3 and/or MEK inhibitor alone or in combination with other standard cancer treatments, such as surgery, radiation therapy, chemotherapy, or any combination thereof. In some examples, the test may include determination of other clinical information (such as determining the presence or absence of mutations in other genes).

VI. Arrays

In particular embodiments provided herein, arrays can be used to evaluate the presence or absence of mutations in GRM3 (or other GPCR(s)). In some examples, the array comprises an oligonucleotide that specifically hybridizes with a GRM3 nucleic acid molecule comprising a mutation selection from G1682A, C1829T, G2299A and G2608A of the GRM3 gene (SEQ ID NO: 1). In particular examples, the array comprises (or further comprises) oligonucleotides that specifically hybridize with additional mutations in GRM3, such as those listed in Table 1. In further examples, the array comprises oligonucleotides that specifically hybridize with mutations in other GPCR genes, including those listed in Tables 1 and 2. In particular examples, the array contains oligonucleotides that specifically hybridize with at least one mutation from each GPCR gene listed in Tables 1 and 2, and may contain oligonucleotides that specifically hybridize with each mutation listed in Tables 1 and 2.

Oligonucleotides that specifically hybridize with a GRM3 nucleic acid comprising a mutation do not hybridize to WT GRM3, or hybridization of the oligonucleotide to WT GRM3 is significantly weaker than hybridization to the mutant GRM3. In some embodiments the array comprises two or more oligonucleotides that specifically hybridize with a GRM3 nucleic acid comprising a mutation selected from G1682A, C1829T, G2299A and G2608A of the GRM3 gene (SEQ ID NO: 1). In other embodiments, the array comprises oligonucleotides that specifically hybridize with GRM3 nucleic acid molecules comprising each mutation of G1682A, C1829T, G2299A and G2608A of the GRM3 gene (SEQ ID NO: 1). In some examples, the array further comprises other oligonucleotides, such as control oligonucleotides or oligonucleotides that specifically hybridize with WT GRM3 or other mutant GRM3 nucleic acid molecules. Exemplary control oligonucleotide probes include GAPDH, actin, and YWHAZ.

The oligonucleotide probes can further include one or more detectable labels, to permit detection of hybridization signals between the probe and target sequence (such as one of the mutant GRM3 nucleic acid molecules).

Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, ethyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that the areas on the support not occupied by the oligonucleotides are not amenable to non-specific binding, or when non-specific binding occurs, such materials can be readily removed from the surface without removing the oligonucleotides.

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit a low background fluorescence.

The array formats of the present disclosure can be included in a variety of different types of formats. A "format" includes any format to which the solid support can be affixed, such as microtiter plates (e.g. multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides to a solid support and for directly synthesizing the oligonucleotides onto the support are known to those working in the field; a summary of suitable methods can be found in Matson et al. (*Anal. Biochem.* 217:306-10, 1994). In one example, the oligonucleotides are synthesized onto the support using conventional chemical techniques for preparing oligonucleotides on solid supports (such as see PCT publications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

VII. Use of GRM3 for Diagnosis, Prognosis and Treatment of Melanoma

It is disclosed herein that a number of GPCR genes are mutated in melanoma tumors. In particular, this disclosure identifies the GRM3 gene as a GPCR that is highly mutated in melanoma.

Using a GPCR-targeted mutational analysis of tumor DNA derived from 11 melanoma samples (as described in Example 1 and 2 below), 106 somatic mutations were identified in 97 different GPCR genes, nine of which contained at least two somatic mutations. The coding regions of these 9 genes were sequenced using DNA obtained from 80 melanoma samples. Sequence analysis revealed 110 non-synonymous (NS) somatic mutations in 47 of the 80 tumor samples.

GRM3 was the most highly mutated GPCR gene found in this initial screen, having a 17.5% mutation rate with 19 NS mutations found in 14 tumors. Thus, GRM3 was further evaluated in an additional melanoma tumor panel consisting of 47 tumor specimens. This second screen identified 5 NS mutations and revealed a mutational hotspot (E87K; SEQ ID NO: 2), which was found in three different melanoma samples.

Figure 2A:
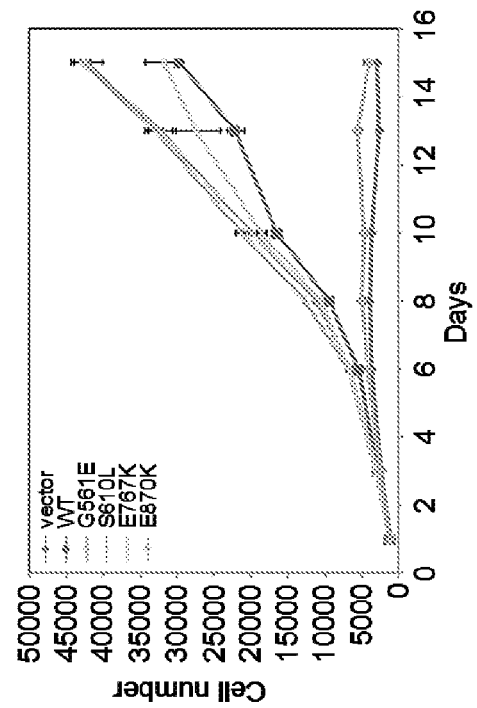
Figure 3A:
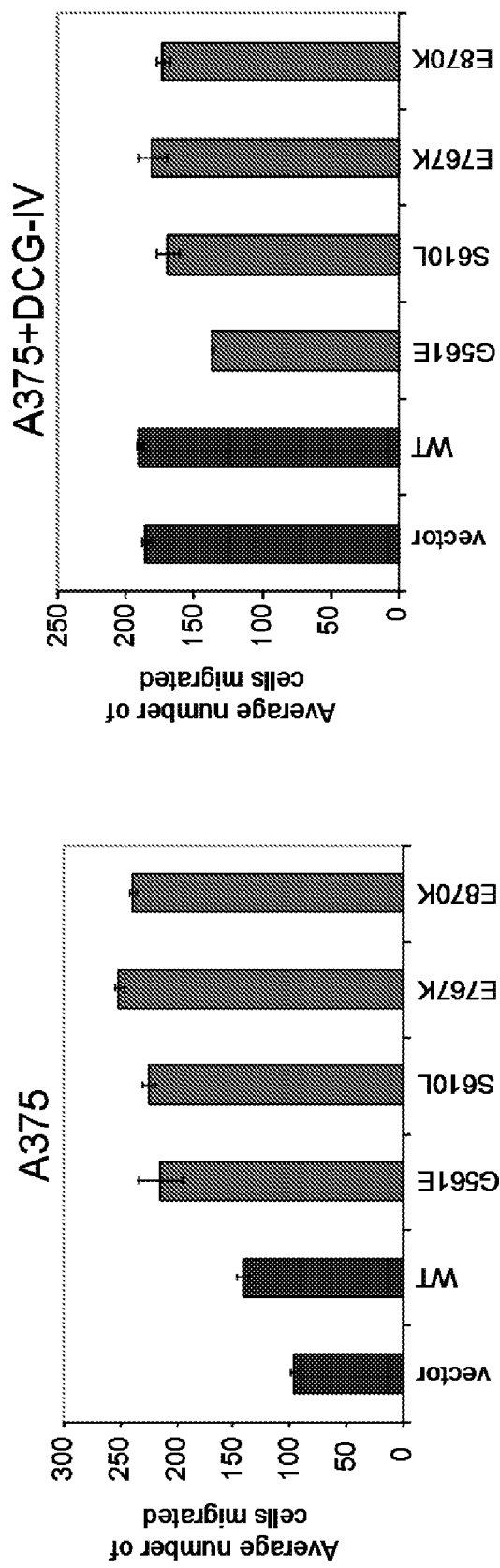

Four somatic mutations identified in GRM3 (G1682A, C1829T, G2299A and G2608A (SEQ ID NO: 1), corresponding to G561E, S610L, E767K and E870K (SEQ ID NO: 2), respectively) were functionally characterized by establishing stable cell lines expressing either WT GRM3 or one of the four mutant GRM3 genes. The results of these functional studies demonstrated that under low serum conditions, cells expressing G561E, S610L or E767K GRM3 grow slower than cells expressing WT GRM3 (FIG. 2A). In addition, all four GRM3 mutants exhibit greater anchorage independent cell growth relative to WT GRM3 expressing cells (FIG. 2B). Further studies demonstrated that expression of mutant GRM3 leads to increased activation of the MEK pathway (as demonstrated by an increase in phosphorylation of MEK1/2; FIG. 2C and FIG. 2D) and increased migration ability in vitro (FIG. 3A and FIG. 3B). The four GRM3 mutations were further evaluated for the ability to promote migratory phenotypes in vivo. Cells expressing mutant GRM3 were administered to NOD/SCID mice and evaluated for lung colonization after 9 weeks. The results demonstrated that mutant GRM3 (S610L, E767K and E870K) promotes growth in vivo and lung colonization.

In light of these findings, disclosed herein is a method of diagnosing melanoma in a subject by detecting one or more mutations in the GRM3 gene. In some examples, the subject is further treated with an appropriate therapy, such as with a GRM3 or MEK inhibitor. Also provided is a method of treating a subject with melanoma harboring a mutation in the GRM3 gene by administering an inhibitor of GRM3 or an inhibitor of MEK. Further provided is a method of selecting a patient with melanoma as a candidate for treatment with a GRM3 inhibitor or an MEK inhibitor by detecting at least one GRM3 mutation in the patient. A method of predicting the prognosis of a subject with melanoma by detecting one or more mutations in GRM3 is also provided.

In some embodiments disclosed herein, the detection of one or more GRM3 mutations selected from G1682A, C1829T, G2299A and G2608A (SEQ ID NO: 1) can be used as a clinical tool to diagnose a patient that has already developed melanoma, or who has an increased risk of developing melanoma. Detection of one or more of the above-listed mutations can also be used to determine the prognosis of a patient previously diagnosed with melanoma. Since these mutations result in an increase in tumor growth and metastasis, a poor prognosis is indicated when one or more of the mutations is detected in a sample from a subject diagnosed with melanoma. Similarly, the presence of one or more of the disclosed mutations indicates a subject has already developed melanoma or is susceptible to developing melanoma.

Detection of one or more of the disclosed mutations in GRM3 can also be used as a tool for determining an appropriate therapy for a subject with melanoma. The presence of one or mutations in GRM3 indicates the subject is a candidate for treatment with a GRM3 inhibitor. In addition, since the functionally characterized mutations in GRM3 result in enhanced activity of MEK, the presence of one or more of these mutations indicates the subject is a candidate for treatment with an inhibitor of MEK. For example, AZD-6244 (AstraZeneca) is a specific MEK inhibitor that is currently being tested in clinical trials for melanoma and other types of cancer. Other known MEK inhibitors include, for example, GSK1120212 (GlaxoSmithKline) and PD0325901 (Pfizer).

The following examples are provided to illustrate certain particular features and/or embodiments. These examples should not be construed to limit the disclosure to the particular features or embodiments described.

EXAMPLES

Example 1

Materials and Methods

This example describes the experimental procedures used for the studies described in Example 2.

Tumor Tissues

Tissue and melanoma cell lines used for the discovery and first validation in this study were described previously (Palavalli et al., *Nat Genet.* 41:518-520, 2009). For the melanoma second validation set, optimum cutting temperature (OCT)-embedded frozen clinical specimens were obtained from the Melanoma Informatics, Tissue Resource, and Pathology Core, and the Central Nervous System Tissue Bank at The University of Texas M. D. Anderson Cancer Center. H&E-guided dissection and isolation of DNA from the tumor-enriched isolates has been described previously (Davies et al., *Clin Cancer Res* 15:7538-7546, 2009).

GPCR Exome Capture and Analysis

Primer Design. Molecular inversion probes (MIPs) were designed using PrimerTile (Chines et al., *American Society of Human Genetics Annual Meeting*, A1257, 2005), a program for automated large-scale design and in-silico testing of PCR primer pairs. This program achieves high target coverage by tiling primer pairs across a given region. This software has been adapted for MIP capture by changing various parameters to construct probe sequence as described in Porreca et al. (*Nat Methods* 4:931-936, 2007). The following general criteria were used to design 7059 probes against 1.6 Mb: (1) Probe targeting arms were designed to capture regions between 160 and 360 bases long; (2) GC content of probe targeting arms was between 30% and 60% (most between 35% and 55%); (3) probe targeting arms did not overlap known dbSNP positions; and (4) probe targeting arms did not include Nt.AlwI or Nb.BsrDI restriction sites. Several rounds of design were run to increase coverage. Redundant targeting pairs were removed. The targeting arm pairs were then correctly oriented into a 100-mer probe. The probes were separated into two non-overlapping sets, and ordered separately from Agilent Technologies, Inc. (Santa Clara, Calif.). Subsequent captures and sequencing were performed separately for each tube of probes. Sequence data for each tube was filtered to only include positions that were captured in that set, and joined during genotype calling.

Probe Preparation

MIP probes were prepared as described in Porreca et al. (*Nat Methods* 4:931-936, 2007) with the following modifications: 10 fmol of synthesized oligo library was amplified in a 1 mL PCR reaction (split into 20 tubes) using 10 µL AMPLI-TAQ GOLD™ (Applied Biosystems/Life Technologies Carlsbad, Calif.), 100 µM of each primer, and 200 µM of each dNTP. Cycling conditions were 5 minutes at 95° C., 20 cycles of 30 seconds at 95° C., 1 minute at 54° C., 2 minutes at 72° C., and 5 minutes at 72° C.

PCR products were purified by phenol/chloroform extraction and ethanol precipitation with $\frac{1}{10}^{th}$ volume 7.5M ammonium acetate. The precipitate was resuspended in 85 µL elution buffer (Qiagen Inc., Valencia, Calif.). The purified product was then digested as described, but with each enzyme incubation extended to 2 hours. The digested product was again purified by phenol/chloroform extraction and ethanol precipitation. The purified digested product was then purified on a 6% denaturing acrylamide gel. Processed, purified probes were quantitated by running a sample against known amounts of a similarly sized DNA fragments on a denaturing acrylamide gel.

Capture

For each tube of probes, 975 ng of genomic DNA was combined with capture probes (3 pM each probe) in 13 µL 1× AMPLIGASE™ buffer (Epicentre Biotechnologies, Madison, Wis.). The reactions were incubated for 4 minutes at 20° C., 5 minutes at 95° C., and 24 hours at 60° C. One µL of extension and ligation mix was added (200 µM dNTPs, 2 U/µL Taq Stoffel fragment (Applied Biosystems/Life Technologies, Carlsbad, Calif.), and 5 U/µL AMPLIGASE™ in 1× AMPLIGASE™ buffer (Epicentre Biotechnologies)). The reaction was allowed to proceed for 24 hours. Linear genomic DNA was degraded with exonuclease.

Amplification of Capture

Amplification was performed using normal PCR with PCR primers CP-2-FA and CP-2-RA (Porreca et al., *Nat Methods* 4:931-936, 2007). PCR was carried out with 1-2 µL capture template, 2× iTaq with SYBR™ Green and Rox (Bio-Rad Laboratories, Hercules, Calif.), and 200 mM of each primer. Conditions used were 5 minutes at 95° C., 23 cycles of 30 seconds at 94° C., 2 minutes at 54° C., and 2 minutes at 72° C. Samples were then end-repaired using the End-It End Repair Kit (Epicentre Biotechnologies, Madison, Wis.). Finally, samples were concatenated overnight at 16° C. using 2000 U T4 DNA/Ligase (New England Biolabs, Ipswich, Mass.), 18% PEG-3350 (Sigma-Aldrich Corp., St. Louis, Mo.) in 1× T4 ligase buffer. After confirmation of efficient concatenation, samples were prepared for shotgun sequencing on the ILLUMINA™ GA-2 platform (Illumina Inc., San Diego, Calif.) with the ILLUMINA™ Library Preparation kit, using Covaris sonication to fragment the samples.

Data Analysis

Initial analysis was performed with the ILLUMINA™ supplied analysis software. Sensitivity, specificity, and coverage were calculated with custom Perl scripts. Genotypes were called using a Bayesian based probability algorithm that takes into account all possible genotypes and assigns a score based on difference between log-likelihoods of first and second most probable genotypes. Empirical testing against HapMap genotypes and Sanger-based sequencing was used to set a score cutoff of 10. Non-reference bases were prioritized by location and classification (i.e., coding, non-synonymous) using methods described in Biesecker et al. (*Genome Res* 19:1665-1674, 2009).

PCR, Sequencing and Mutational Analysis of Melanoma Samples

PCR and sequencing was performed as previously described (Palavalli et al., *Nat Genet.* 41:518-520, 2009; Viloria et al., *Cancer Res* 69:4926-4934, 2009; Prickett et al., *Nat Genet.* 41:1127-1132, 2009). PCR primer sequences are shown in Table 6. The primary phase mutation screen was analyzed using Consed. Variants were called using Polyphred 6.11 and DIPDetector, an indel detector for improved sensitivity in finding insertions and deletions. Sequence traces of the secondary screen were analyzed using the Mutation Surveyor software package (SoftGenetics, State College, Pa.).

Construction of Wild-Type, Mutant and Non-Targetable GRM3 Expression Vectors

Human GMR3 (GenBank Accession No. NM_000840; SEQ ID NO: 1) was cloned by PCR using a clone (cat #MHS1010-9203778) purchased from Open Biosystems and the primers shown in Table 7.

The PCR product was cloned into the mammalian expression vector pCDF-MCS2-EF1-Puro™ (Systems Biosciences, Inc., Mountain View, Calif.) or pcDNA3.1(−) (Invitrogen, Carlsbad, Calif.) via the XbaI and NotI restriction sites. The G561E, S610L, E767K, and E870K point mutants were made using Phusion PCR for site-directed mutagenesis. The nucleotide and amino acid sequences of human GRM3 are set forth herein as SEQ ID NO: 1 and SEQ ID NO: 2, respectively.

GRM3 cDNA fragments were amplified using the primers in Table 7 as previously described (Palavalli et al., *Nat Genet.* 41:518-520, 2009; Prickett et al., *Nat Genet.* 41:1127-1132, 2009) and subsequently used for amplification of a non-targetable (NT) insert. The NT-GRM3 insert was then cloned into pCDF-MCS2-EF1-Neo™ (Systems Biosciences, Inc., Mountain View, Calif.) via the XbaI and NotI restriction sites.

Cell Culture and Transient Expression

Metastatic melanoma tumor lines were maintained according to standard procedures. HEK 293T cells were purchased from the ATCC (Manassas, Va.) and maintained in complete Dulbecco's modified Eagles medium (DMEM) supplemented with 10% FBS, 1× non-essential amino acids, 2 mM L-glutamine, and 0.75% sodium bicarbonate. A375 cells were purchased from the National Cancer Institute, Division of Cancer Treatment, Developmental Therapeutics Program (Frederick, Md.) and maintained in RPMI-1640 supplemented with 10% FBS. Mel-STR cells were described previously. HEK 293T cells were transfected with LIPOFECTAMINE™ 2000 reagent (Invitrogen, Carlsbad, Calif.) at a 6:1 ratio with DNA (μλ:μg) using 3-5 μg of plasmid DNA.

Immunoprecipitation and Western Blotting

Transfected cells or stable pooled clones were gently washed 3× in PBS and then lysed using 0.5-1.0 ml 1% NP-40 lysis buffer (1% NP-40, 50 mM Tris-HCl pH 7.5, 150 mM NaCl, complete protease inhibitor tablet, EDTA-free (Roche, Indianapolis, Ind.), 1 μM sodium orthovanadate, 1 mM sodium fluoride, and 0.1% β-mercaptoethanol) per T75 flask for 20 minutes on ice. Lysed cells were scraped and transferred into a 1.5 mL microcentrifuge tube. Extracts were centrifuged for 10 minutes at 14,000 rpm at 4° C. Supernatant (500 μl) was immunoprecipitated overnight using 20 μl of anti-FLAG (M2) beads (Sigma-Aldrich). The immunoprecipitates were washed and subjected to SDS-PAGE and western blotting according to standard procedures. Cell lysates were generated by gently washing plates with PBS followed by addition of 2×SDS sample buffer. Primary antibodies used in this analysis included horseradish peroxidase conjugated anti-FLAG (Sigma-Aldrich) and anti-alpha-tubulin (Calbiochem-EMD Biosciences, Gibbstown, N.J.).

Pooled Stable Expression

To make lentivirus, GRM3 constructs were co-transfected into HEK 293T cells seeded at $1.5 \times 10^6$ per T75 flask with pVSV-G and pFIV-34N helper plasmids using LIPOFECTAMINE™ 2000 as described by the manufacturer. Virus-containing media was harvested 48-60 hours after transfection, filtered, aliquoted and stored at −80° C. A375 cells were seeded at $1.5 \times 10^6$ cells per T75 flask 24 hours prior to infection. Lentivirus for GRM3 (WT, G561E, S610L, E767K, and E870K) or empty vector control were used to infect A375 cells as previously described (Solomon et al., *Cancer Res* 68:10300-10306, 2008). Stable expression of GRM3 proteins (WT and mutants) was determined by SDS-PAGE analysis followed by immunoprecipitation and immunoblotting with anti-FLAG and anti-alpha-tubulin to show equivalent expression among pools.

Mel-STR cells were seeded at $1.5 \times 10^6$ per T75 flask 24 hours prior to transfection with GRM3 (WT, G561E, S610L, E767K, or E870K) or empty vector control in pcDNA3.1(−) using EFFECTENE™ (Qiagen) according to the manufacturer's protocol. Cells were selected using normal complete growth medium supplemented with 300 μg/ml G418 and pooled for future experiments. Stable expression of GRM3 proteins (WT and mutants) was determined by SDS-PAGE analysis followed by immunoprecipitation and immunoblotting with anti-FLAG and anti-alpha-tubulin to show equivalent expression among pools.

Signaling Pathway Stimulation

HEK 239T cells transfected with GRM3 (WT, G561E, S610L, E767K, or E870K) or empty vector control, or A375 or Mel-STR pooled GRM3 clones, were seeded in 6-well plates at $1-2 \times 10^5$ cells/well the day before transfection. Cells were serum-starved for 16 hours prior to stimulation with 2.5 μM DCG-IV (Tocris Biosciences, Ellisville, Mo.) for 10 minutes. Cell lysates were generated by direct lysis into 2×SDS samples buffer and then subsequently analyzed by western blotting using anti-phospho-Erk1/2 (cat#4370), anti-Erk1/2 (cat#4695), anti-phopho-MEK1/2 (cat#9154), anti-MEK1/2 (cat#9126), anti-phospho-Akt (S473) (cat#9271), anti-Akt (cat#9272) (Cell Signaling, Danvers, Mass.), anti-GAPDH (cat# CB 1001) (Millipore-Billerica, Mass.) or anti-alpha-tubulin (cat# CP06) (EMD-Calbiochem-Gibbstown, N.J.) as a loading control.

Proliferation Assays

To examine growth potential, pooled A375 and Mel-STR GRM3 clones were seeded into 96-well plates at 250 cells per well in either 1%, 2.5% or 10% serum-containing medium and incubated for 13-17 days. Samples were analyzed every 48 hours by lysing cells in 50 μl 0.2% SDS/well and incubating for 2 hours at 37° C. prior to addition of 150 μl/well of SYBR™ Green I solution (1:750 SYBR™ Green I (Invitrogen, Carlsbad, Calif.) diluted in dH₂O). Plates were analyzed using a BMG Labtech FLOUstar Optima.

Soft Agar Assay

Mel-STR pooled GRM3 clones were plated in triplicate at 1000 cells/well and in top plugs consisting of sterile 0.33% Bacto-Agar (BD, Sparks, Md.) and 10% fetal bovine serum (HyClone, Logan, Utah) in a 24-well plate. The lower plug contained sterile 0.5% Bacto-Agar and 10% fetal bovine serum. After two weeks, the colonies were photographed and quantitated using ImageJ (NIH software).

Migration Assays

Mel-STR pooled clones were seeded into pre-conditioned migration wells (8.0 μm—BD Biocoat, BD Biosciences) at 30,000 cells per well in serum-free medium or serum-free medium plus 2.5 μM DCG-IV in the top chamber. Cells were incubated for 16-18 hours with medium containing complete serum in the bottom chamber prior to harvesting. A375 pooled clones were seeded into pre-conditioned migration wells (8.0 μm—BD Biocoat, BD Biosciences) at 30,000 cells per well in serum-free medium or serum-free medium plus 2.5 μM DCG-IV in the top chamber. Cells were incubated for 12-14 hours with medium containing complete serum in the bottom chamber prior to harvesting. Inserts were fixed and stained using Hema 3 Stat Pack according to the manufacturer's protocol. Inserts were analyzed and the number of cells migrated per field view was quantitated using ImageJ (NIH software).

Lentiviral shRNA

Constructs for stable depletion of GRM3 (cat# RHS4533-NM_000840) were obtained from Open Biosystems (Huntsville, Ala.) and were confirmed to efficiently knockdown GRM3 at the protein level. Lentiviral stocks were prepared as previously described (Palavalli et al., Nat Genet. 41:518-520, 2009). Melanoma cell lines (34T, 36T, 49T, and 76T) were infected with shRNA lentiviruses for each condition (vector and a GRM3 specific shRNA). Selection and growth were carried out as described above. Stably infected pooled clones were tested in functional assays.

For the shRNA inducible system, constructs for stable depletion of GRM3 (cat# RHS4740-NM_000840) were obtained from Open Biosystems (Huntsville, Ala.) and were confirmed to efficiently knockdown GRM3 at the message level. Lentiviral stocks were prepared as previously described (Palavalli et al., Nat Genet. 41:518-520, 2009). Melanoma cell lines (31T or 36T) were infected with shRNA lentiviruses for each condition (vector and two different GRM3 specific shRNAs). Selection and growth were performed as described above. Stably infected pooled clones were tested in functional assays. Doxycycline inducible shRNA knock-down clones were grown in the presence of 0.2 μg/ml of doxycycline for 7 days prior to any functional assays. The clones were kept in the presence of 0.2 μg/ml doxycycline throughout the experiment.

Sequences of stable shRNA knock-down plasmids for GRM3 are shown below (sense-loop-antisense).

```
GRM3 shRNA#1 (NM_000840) (TRCN0000009015)-
                                    SEQ ID NO: 17
CCGGCAGAACATGGAAATAACCATTCTCGAGAATGGTTATTTCCATGT

TCTGTTTTT

GRM3 shRNA#2 (NM_000840) (TRCN0000009016)-
                                    SEQ ID NO: 18
CCGGCGAAGCTAAGTTCATAGGTTTCTCGAGAAACCTATGAACTTAGC

TTCGTTTTT

GRM3 shRNA#3 (NM_000840) (TRCN0000009017)-
                                    SEQ ID NO: 19
CCGGGCCTGTTTCCTATTAACGAAACTCGAGTTTCGTTAATAGGAAAC

AGGCTTTTT

GRM3 shRNA#4 (NM_000840) (TRCN0000009018)-
                                    SEQ ID NO: 20
CCGGGCAGATAGCATAGTCAAGTTTCTCGAGAAACTTGACTATGCTAT

CTGCTTTTT

GRM3 shRNA#5 (NM_000840) (TRCN0000011672)-
                                    SEQ ID NO: 21
CCGGCCTGTCATACTGCATGACATTCTCGAGAATGTCATGCAGTATGA

CAGGTTTTT

GRM3 sh639 (NM_000840) (V2THS_236639)-
                                    SEQ ID NO: 46
TGCTGTTGACAGTGAGCGCCGGCTCCATTCAACCCAAATATAGTGAAG

CCACAGATGTATATTTGGGTTGAATGGAGCCGTTGCCTACTGCCTCGGA

GRM3 sh742 (NM_000840) (V3THS_395742)-
                                    SEQ ID NO: 47
TGCTGTTGACAGTGAGCGCCCGCTTCTTCAACTGGACCTATAGTGAAGC

CACAGATGTATAGGTCCAGTTGAAGAAGCGGATGCCTACTGCCTCGGA
```

Reverse Transcription PCR

Total RNA was extracted from pooled clones of melanoma cells 36T and 34T stably knocked-down for endogenous GRM3 following the manufacturer's protocol for RNeasy™ Mini Kit (Qiagen #74101). Total RNA was eluted in 30 μl DEPC-treated $dH_2O$. A total of 1 μg of total RNA was used for single strand cDNA synthesis using a SUPERSCRIPT™ III First Strand kit (Invitrogen #18080-051). cDNA was amplified using the oligo $dT_{20}$ primer supplied in the kit. To test for loss of GRM3 message, 2 μl of cDNA was used in the PCR reaction with either GRM3 primers (forward primer: ttgggtgttcacattttgga (SEQ ID NO: 3) and reverse primer: tcacgctgtcgtaggacttg (SEQ ID NO: 4)) or GAPDH primers (forward primer: tggaaggactcatgaccaca (SEQ ID NO: 5) and reverse primer: tgctgtagccaaattcgttg (SEQ ID NO: 6)). The product was then analyzed on a 1% agarose gel.

Tail Vein Injection Studies in Mice

NOD/SCID mice were purchased from The Jackson Laboratory (Barn Harbor, Me.). All mice were housed in a pathogen-free facility and were given autoclaved food and water. A375 pooled clones with empty vector or with wild-type or mutant GRM3 were grown up in T175 flasks to 70-80% confluency. Cells ($1 \times 10^6$) were resuspended in 100 μL of sterile PBS and injected intravenously (tail) into 7-10 week old SCID mice. Mice were monitored bi-weekly and lungs were examined and quantified for tumor formation by excision from euthanized mice at day 60 post-injection.

Subcutaneous Injection Studies in Mice

Nu/Nu mice were purchased from Charles River Labs. All mice were housed in a pathogen-free facility and were given autoclaved food and water. 31T (pLKO.1, #1 shRNA or #3 shRNA) or 36T (pLKO.1, #1 shRNA or #3 shRNA) cell lines were grown up in 4-6 T-175 flasks each to 90% confluency. Cells ($2.5 \times 10^6$) were resuspended in 200 μl of sterile 1×PBS:matrigel solution (1:1 v/v) (BD Biosciences #354234) and injected subcutaneously into 6-8 week old female Nu/Nu mice. Mice were monitored bi-weekly and tumor diameters were measured using precision calipers for 17-20 days. For the shRNA inducible system, all mice were given sterile doxycycline food (5 g/mouse/day) and water. 31T (TRIPz-NC, sh639, or sh742) or 63T (TRIPz-NC, sh639, or sh742) cell lines were grown up in 4-6 T-175 flasks each to 90% confluency. Cells ($2.5 \times 10^6$) were resuspended in 200 μl of sterile 1×PBS:matrigel solution (1:1 v/v) (BD Biosciences #354234) and injected subcutaneously into 6-8 week old female Nu/Nu mice. Mice were monitored bi-weekly and tumor diameters measured using precision calipers for 17-20 days.

Growth Inhibition Analysis

To test AZD-6244 (cat #S 1008; Selleck Chemicals LLC-Houston, Tex.) inhibition on melanoma cell lines, 96-well plates were seeded at 5,000 cells per well and incubated 24 hours prior to addition of inhibitor at concentrations from 10 nM to 30 μM. Once the inhibitor was added, cells were incubated for 72 hours at 37° C. Cells were then analyzed using CellTiterGlo according to the manufacturer's protocol (cat# G7571) (Promega-Madison, Wis.). Plates were read on a Luminoskan Ascent reader (Thermo Scientific) plate reader and analyzed using Microsoft Excel GraphPad Prism™ v5.

To test AZD-6244 inhibition of cells that had been stimulated with DCG-IV to activate MEK1/2, melanoma cells were plated in 96-well plates at 2,000 cells per well in either RPMI-1640/0.5% FBS/2.5 µM DCG-IV or RPMI-1640/10% FBS and incubated for 24 hours prior to addition of inhibitor at concentrations from 2 nM to 30 µM. Once the inhibitor was added, cells were incubated for 72 hours at 37° C. Plates were then analyzed as described above.

Flow Cytometry Analysis

Melanoma cells were seeded into T25 flasks at a density of $3 \times 10^5$ cells per flask in normal complete T2 medium and incubated at 37° C. for 24 hours prior to addition of AZD-6244 (cat #S1008) (Selleck Chemicals LLC-Houston, Tex.). AZD-6244 or vehicle was added for 72 hours at a concentration of 2 µM. Cells were then harvested for FACS analysis by first removing the medium into a new conical tube followed by trypsinizing of attached cells in T25 flasks. Trypsinized cells and those from the medium were combined and washed in ice-cold PBS. Cells were collected by centrifugation at 1,000 rpm at 4° C. Ice-cold 70% ethanol was added to cell pellets and allowed to fix overnight at 4° C., followed by washing in ice-cold PBS. DNase-free RNase (Roche) was added to cells resuspended in 0.5-1 ml PBS and incubated at 37° C. for 30 minutes before adding 50-100 µl of propidium iodide (PI-0.5 mg/ml) (Roche). Cellular DNA content was analyzed on Becton Dickinson FACSCalibur™ using CellQuest software.

Statistical Analysis

Statistical analyses were performed using Microsoft Excel to generate p-values to determine significance (two-tailed t-test).

Accession Codes

GRM3, CCDS5600.1; CHRM3, CCDS1616.1; LPHN2, CCDS1616.1; RXFP1, CCDS43276.1; GRM8, CCDS5794.1; CNR1, CCDS5015.1; OR1J2, CCDS35121.1; OR8B8, CCDS8446.1; OPN5, CCDS4923.1; OR8K1, CCDS31528.1; GPR98, CCDS47246.1; MEK, CCDS10216.1; NRAS, CCDS877.1; BRAF, CCDS5863.1; ERK, CCDS10672.1, each of which is herein incorporated by reference.

Data Access

Somatic variants are listed in Table 3, and are deposited to the SRA (available online trace.ncbi.nlm.nih.gov/Traces/sra/). Accession number: SRA024490, Study number: SRP003752, which is herein incorporated by reference.

Example 2

GRM3 Mutations in Melanoma

To identify possible GPCR somatic mutations in melanoma, a GPCR-targeted mutational analysis was performed in tumor DNA derived from 11 melanoma samples. For each sample, in-solution DNA capture of 7059 regions encompassing 1,566,947 nucleotides corresponding to 2400 GPCR exons was performed using MIP (Porreca et al., *Nat Methods* 4:931-936, 2007). DNA samples enriched for GPCR exons were then analyzed by next generation sequencing using the ILLUMINA™ platform. This analysis identified 755 potential non-synonymous mutations when comparing the MIP results to the known HapMap sequence. To determine which of these alterations was somatic (i.e. tumor-specific), the sequence of the gene in genomic DNA derived from matched normal tissue was examined. From these alterations, 106 were confirmed to be somatic in 97 different genes (Table 2). Nine of these genes harbored at least two somatic mutations (Table 3). The coding exons of these nine genes were analyzed for somatic mutations in a total of 80 melanoma samples using specific primers and dye-terminator chemistry sequencing methods. FIG. 1 depicts the various genetic stages described above.

Figure 6A:
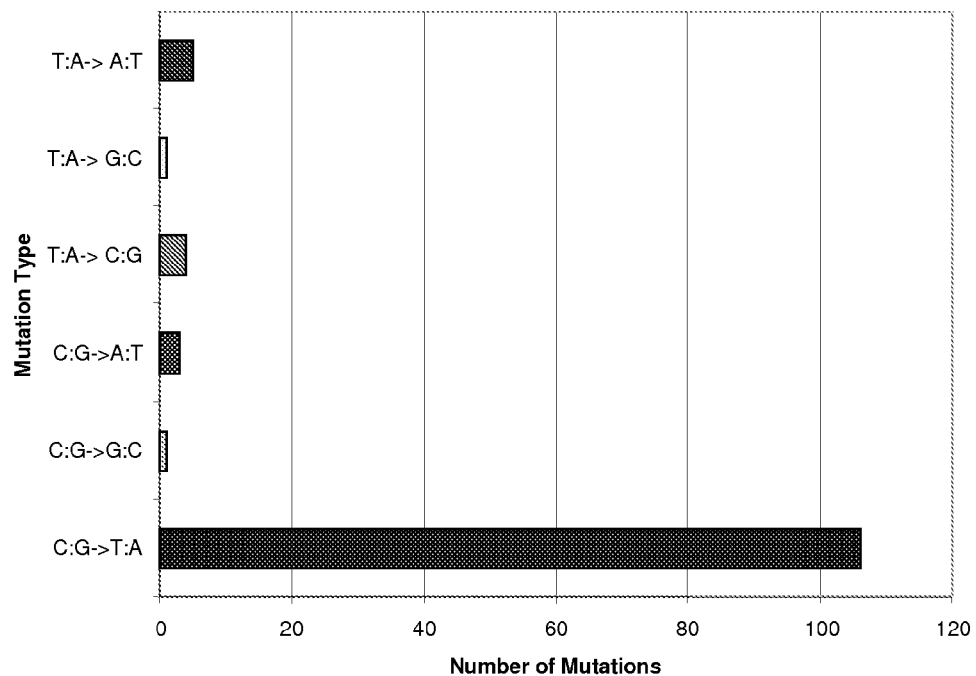
FIGS. 6A-6B: Mutation spectra of single base pair substitutions.
Figure 6B:
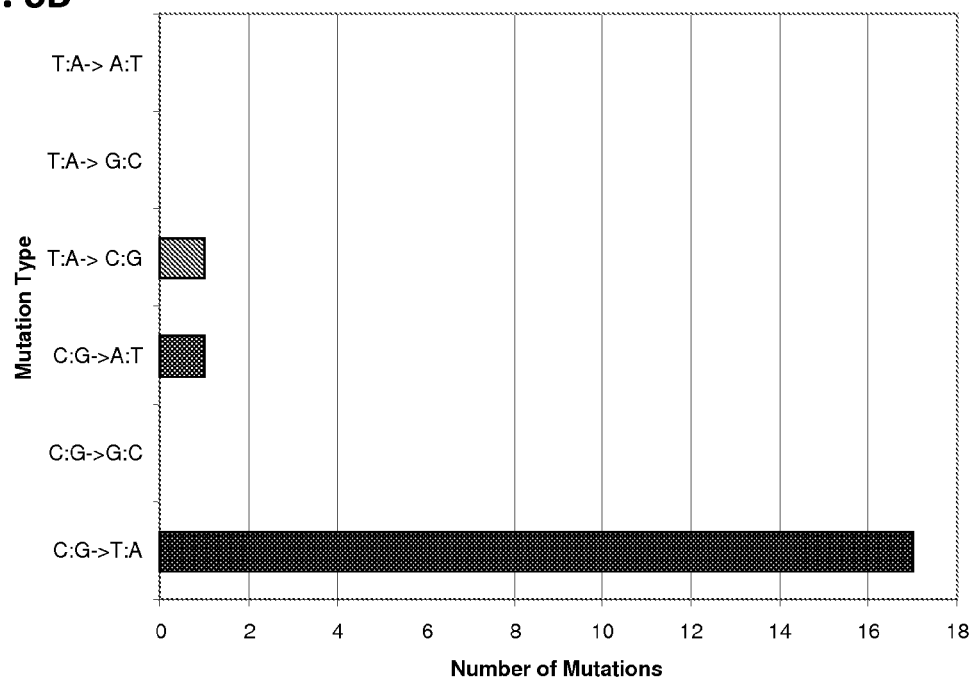

From the ~3.4 Mb of sequencing information from these nine genes, 110 non-synonymous, somatic mutations were identified in 47 of the 80 tumors (Table 1). The number of C>T mutations was significantly greater than the number of other nucleotide substitutions, resulting in a high prevalence of C:G>T:A transitions ($P<1\times10^{-6}$) (FIG. 6), consistent with known melanoma mutation signatures (Greenman et al., *Nature* 446:153-158, 2007). Both alleles of the gene were affected in 11 tumors spanning 6 genes. A total of 5 nonsense mutations and 2 splice site alterations were found, potentially resulting in aberrant or truncated proteins for 5 of the genes. Intriguingly, recurring mutations were identified in CHRM3, RXFP1 and OR1J2, which harbored the P421L/P421S; S269F and D109N mutations, respectively in two individual melanoma cases.

Figure 7A:
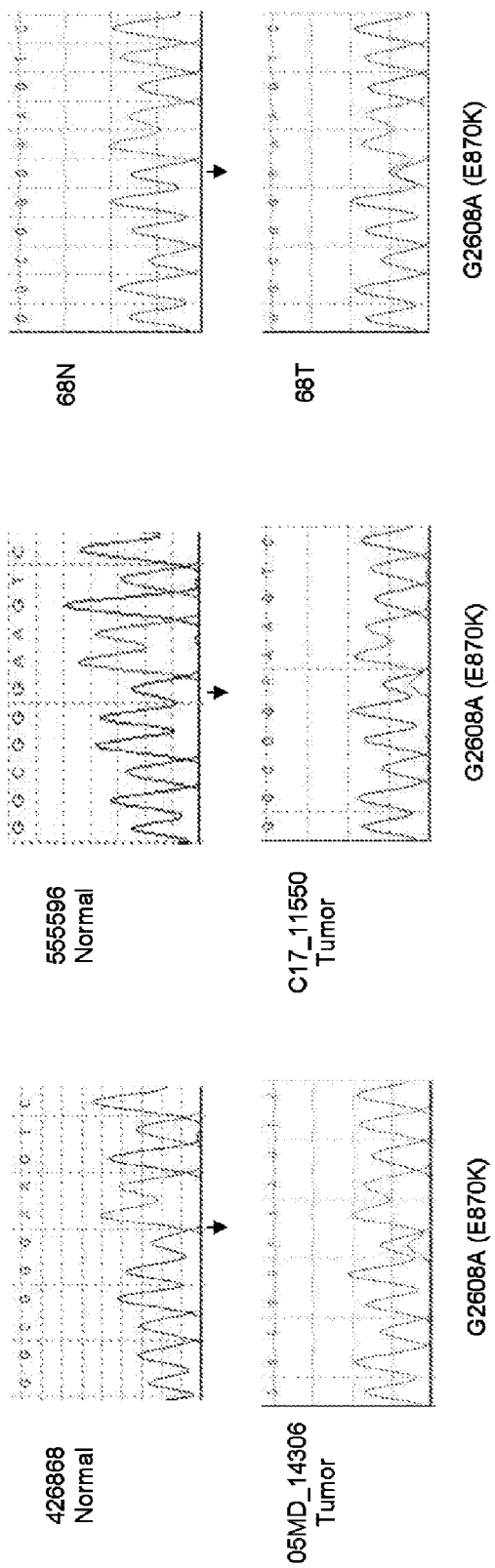
FIGS. 7A-7B: Detection and distribution of mutations in GRM3.
Figure 7B:
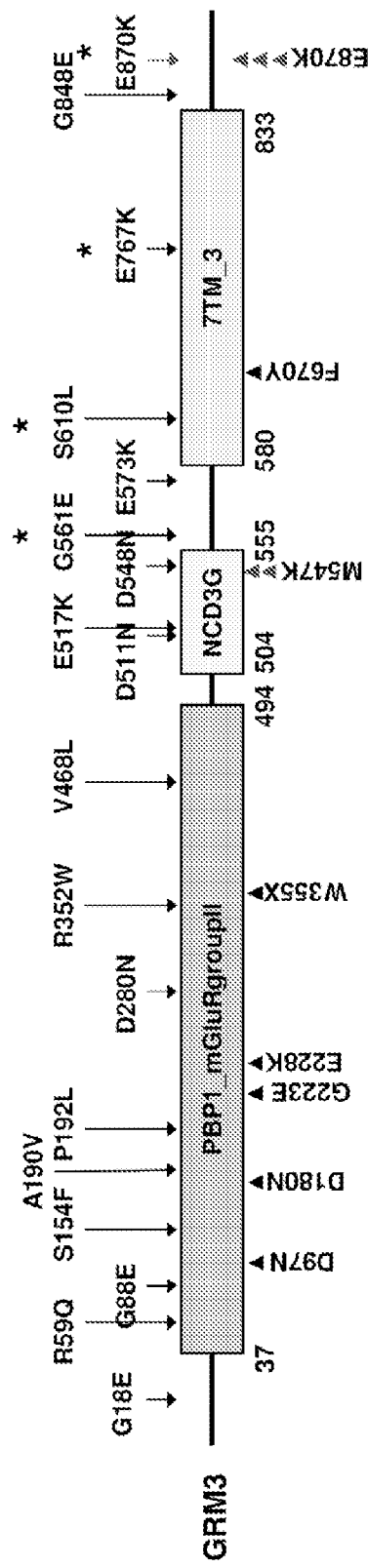

GRM3 and GPR98 were the most frequently mutated GPCR genes found in this screen. GRM3 had a 17.5% mutation rate, with 19 non-synonymous (NS) mutations found in 14 tumors. GPR98 had a total of 43 NS mutations in 30 out of 80 tumors (37.5%). As GPR98 has a coding sequence of ~600 kb, when taking into account coding sequence length, its distribution of somatic mutations does not differ from that expected by chance; this was not the case for GRM3. GRM3 was found to harbor the highest number of NS mutations per base pair sequenced, therefore it was further evaluated genetically in an additional melanoma tumor panel consisting of 47 melanoma specimens (Davies et al., *Clin Cancer Res* 15:7538-7546, 2009). In this screen, 5 NS alterations were discovered, affecting 8.5% of the cases analyzed. Importantly, this investigation allowed the identification of a mutational hotspot in GRM3 (E870K) which was found in 3 different melanoma cases (one in the original melanoma panel and two in the second melanoma panel) (Table 4 and FIG. 7). Clinical information for all melanoma tumors is described in Table 5.

To evaluate the effect of some of the identified mutations on GPCR function, further studies focused on the group II metabotropic glutamate receptor-3 gene (GRM3 or mGluR3) as two genetic observations suggested that these mutations may be functionally significant for melanoma tumorigenesis: (1) it was found to be one of the most highly mutated genes in the GPCR screen; and (2) it contained a mini-hotspot (E870K).

Four somatic mutations (G561E, S610L, E767K, and E870K) discovered in GRM3 were chosen for further characterization based on their species and family member sequence conservation, as well as their location within particular functional domains. Missense mutants S610L and E767K are both located within the 7-transmembrane domain common to most if not all GPCR protein molecules (Dorsam and Gutkind, *Nat Rev Cancer* 7:79-94, 2007) as seen in the schematic in FIG. 7B. The two other mutations fall just proximal to either end of the transmembrane region with the hotspot mutant E870K falling within the cytoplasmic tail of the receptor.

To examine the biological and tumorigenic effects of GRM3 mutations, stable pooled clones were established in which either vector control, WT, or mutant (G561E, S610L, E767K, E870K) GRM3 was expressed. The melanoma cell line A375 and Mel-STR cell line were selected as they express WT GRM3. Similar levels of expression of GRM3 protein were observed in both the A375 and Mel-STR stable clone cell lines, except for mutants E767K and E870K, which exhibited lower total expression levels (FIG. 8).

Figure 9A:
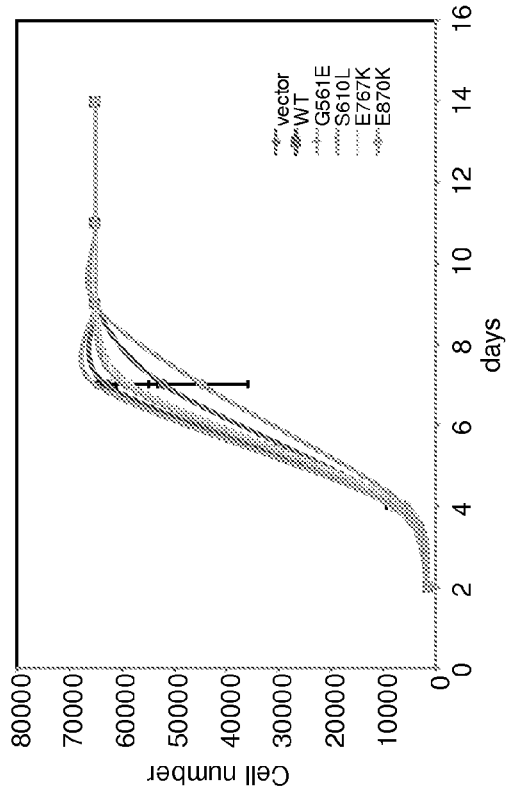
FIGS. 9A-9B: Somatic mutations in GRM3 have no effect on cell growth in 10% serum. A375 (FIG. 9A) and Mel-STR (FIG. 9B) pooled GRM3 clones were seeded in complete normal medium (10% FBS) in 96-well plates and incubated over a 14 day period. Plates were harvested and analyzed by SYBR™ Green I on a BMG Labtech Fluor Optima reader.
Figure 9B:
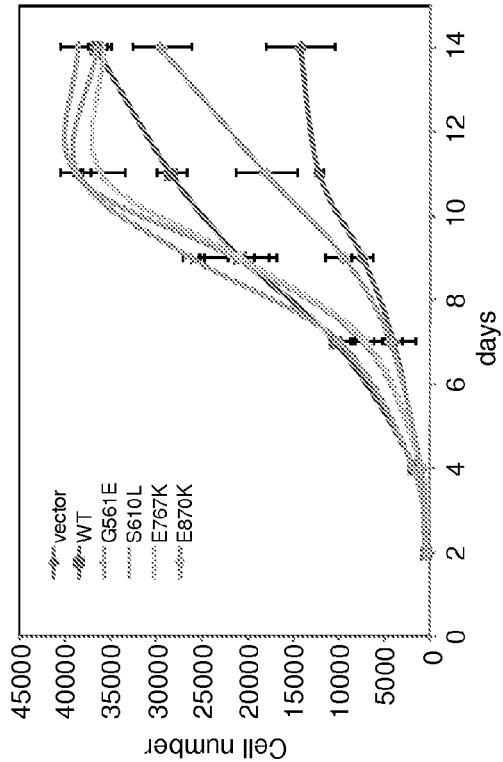

Mutations in genes such as GRM3 might confer some growth advantage on melanoma cells, thus facilitating clonal expansion. To examine the effects of GRM3 mutations on cell growth, growth rate was investigated on plastic tissue culture plates and in soft agar (FIGS. 2A and 2B). In the presence of media containing 10% serum, all clones grew similarly on plastic, except mutant E870K, which grew slower than the other GRM3 mutations in A375 cells (FIG. 9). However, if the serum concentration was reduced to 1%, WT clones grew at a lower rate than mutant clones on plastic, except the clone expressing the E870K mutation (FIG. 2A). The difference in cell growth was also observed when the cells were assessed for anchorage independence, where cells expressing mutant GRM3 formed a significantly higher number of colonies compared to WT or empty vector (FIG. 2B; $p<0.05$ t-test).

The cytoplasmic tail of GPCR proteins is important for binding signaling molecules involved in pathways such as the RAS-RAF-MEK pathway (Dorsam and Gutkind, *Nat Rev Cancer* 7:79-94, 2007; Lee et al., *Pigment Cell Melanoma Res* 21:415-428, 2008). Mutations in the cytoplasmic tail of GRM3 may therefore increase signal transduction leading to increased cell proliferation, thus providing the biochemical basis for the growth differences described above. As previous reports demonstrated group II metabotropic glutamate receptors can be activated by certain agonists such as DCG-IV leading to increased activation of signaling pathways (Aronica et al., *Eur J Neurosci* 17:2106-2118, 2003; Brabet et al., *Neuropharmacology* 37:1043-1051, 1998; Nishi et al., *Br J Pharmacol* 130:1664-1670, 2000), the biochemical effects of GRM3 mutations were tested in the presence and absence of the DCG-IV agonist. The most striking differences were observed in MEK1/2 phosphorylation. When A375 clones were stimulated with DCG-IV, there was 4- to 10-fold increased phosphorylation of MEK1/2 compared to WT GRM3 expressing cells (FIG. 2C, right panel). Similar results were observed in the Mel-STR clones, which upon stimulation of cells with DCG-W, a 7- to 10-fold increase in MEK1/2 phosphorylation was observed compared to clones expressing WT GRM3 (FIG. 2D, right panel). Notably, A375 cells harbor mutant BRAF and Mel-STR cells harbor mutant Ras, both of which are known to activate MEK (Solit et al., *Nature* 439:358-362, 2006), mutant GRM3 thus allowed further activation of the MEK pathway.

Previous studies reported that activation of the MEK pathway increases cell migration (Bian et al., *Cancer Res* 64:4209-4217, 2004; Yu et al., *Proc Natl Acad Sci USA* 106:2635-2640, 2009). As GRM3 variants activate the MEK pathway, additional studies were performed to determine whether they cause increased migration. To test this, A375 or Mel-STR pooled clones were seeded in serum-free medium in the presence or absence of the agonist DCG-IV and subsequently examined for migration (FIGS. 3A-B). Mutant GRM3 expression in either A375 or Mel-STR cells significantly increased migration compared to WT GRM3 or empty vector containing cells in the absence of agonist (FIGS. 3Ai and 3Bi, $p<0.05$ t-test). Upon stimulation with DCG-IV, both the vector and WT expressing cells migrated to a similar extent as mutant GRM3 expressing cells in the absence of stimuli (FIGS. 3Aii and 3Bii). These results suggest that cells harboring mutant forms of GRM3 have increased migration ability in the absence of growth factors or receptor agonists.

Figure 3C:
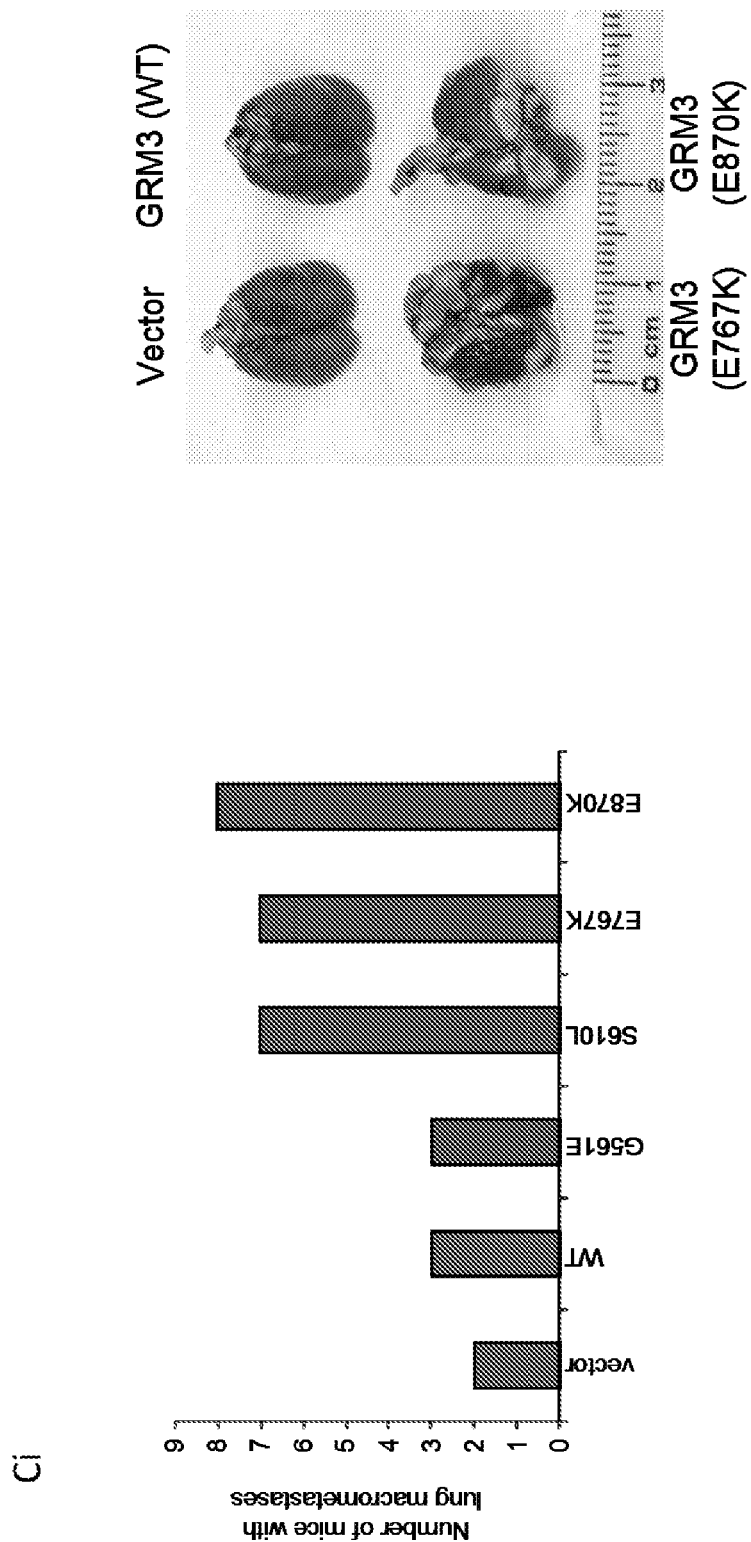
Figure 10B:
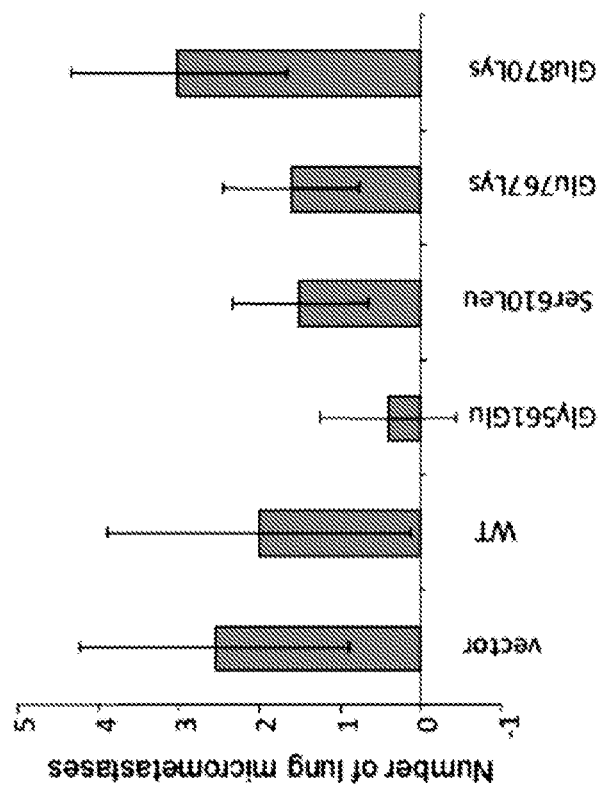
FIGS. 10A-10B: Expression of mutant GRM3 in mice results in similar lung micro-metastases formation. NOD/SCID mice were intravenously injected with A375 pooled GRM3 clones expressing WT, G561E (Gly561Glu), S 610L (Ser610Leu), E767K (Glu767Lys), E870K (Glu870Lys), or vector alone and examined after nine weeks for lung micrometastases size (volume) (FIG. 10A) or number (FIG. 10B).
Figure 10A:
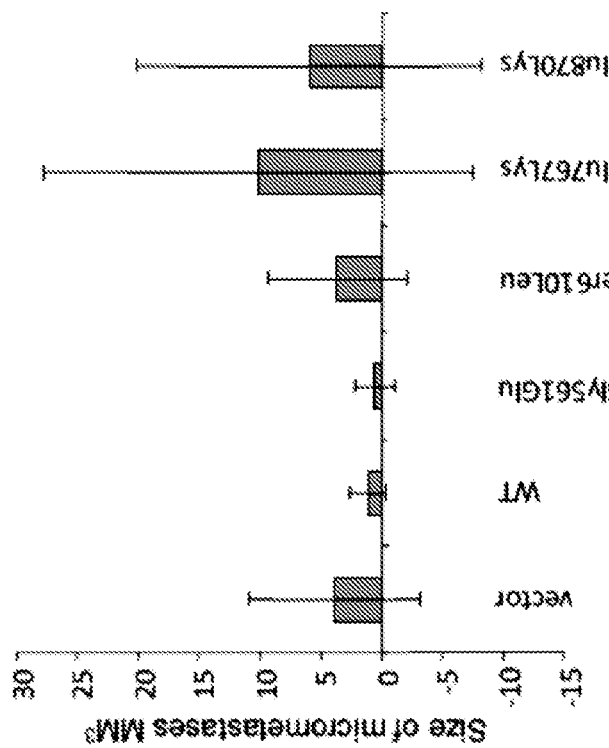

To determine whether these phenotypes occur in vivo, A375 pooled clones expressing vector, WT or mutant GRM3 were administered to NOD/SCID mice by tail vein injection. Nine weeks after injection, macroscopic assessment of lung colonization showed that groups of mice injected with cells expressing vector, WT or mutant G561E, had 2-3 mice with gross lung tumors. In contrast, most of the mice injected with cells expressing the S610L, E767K, or E870K GRM3 mutations had pulmonary macrometastases (FIG. 3C). Microscopic examination allowed the detection of micrometastases, with no significant difference in number or size of the micrometastases (FIGS. 10A and 10B). These results demonstrate that expression of mutant forms of GRM3 in melanoma cells affects growth in vivo and lung colonization.

To assess if melanoma cells harboring endogenous GRM3 mutations are dependent on GRM3 signaling for proliferation and migration, shRNA was used to stably knock-down GRM3 protein levels in melanoma cells harboring either WT GRM3 (34T and 49T) or mutant GRM3 (36T-G561E and 76T-S610L). Specific targeting of GRM3 was confirmed by RT-PCR analysis, using GRM3 specific primers and gapdh as a loading control, or by transient transfection in HEK293T cells and immunoblotting (FIG. 4Ai-ii). The GRM3 shRNA had little to no effect on cells harboring WT GRM3, but significantly reduced the growth of cells harboring mutant forms of GRM3 (FIG. 4Bi-iv). Depletion of GRM3 by shRNA in mutant GRM3 expressing cells reduced their ability to migrate significantly compared to WT GRM3 cells targeted with GRM3 shRNA (FIG. 4Ci-iv).

Figure 11A:
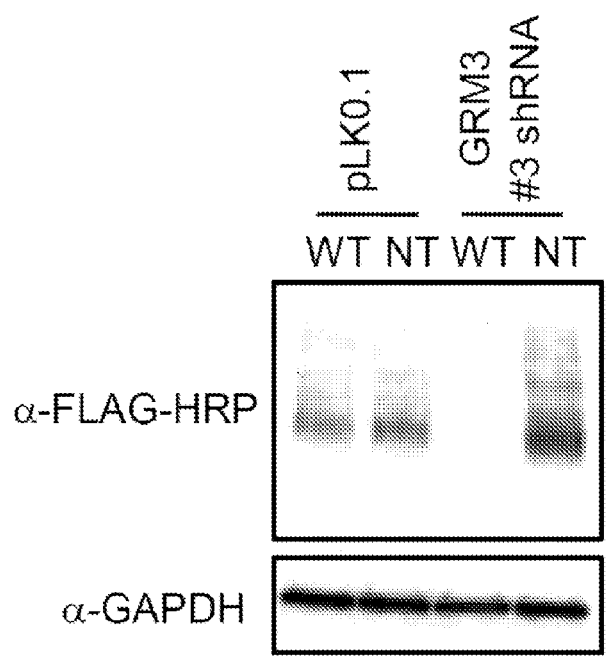
FIGS. 11A-11B: Rescue of GRM3 migratory dependence by exogenous non-targetable GRM3.
Figure 11B:
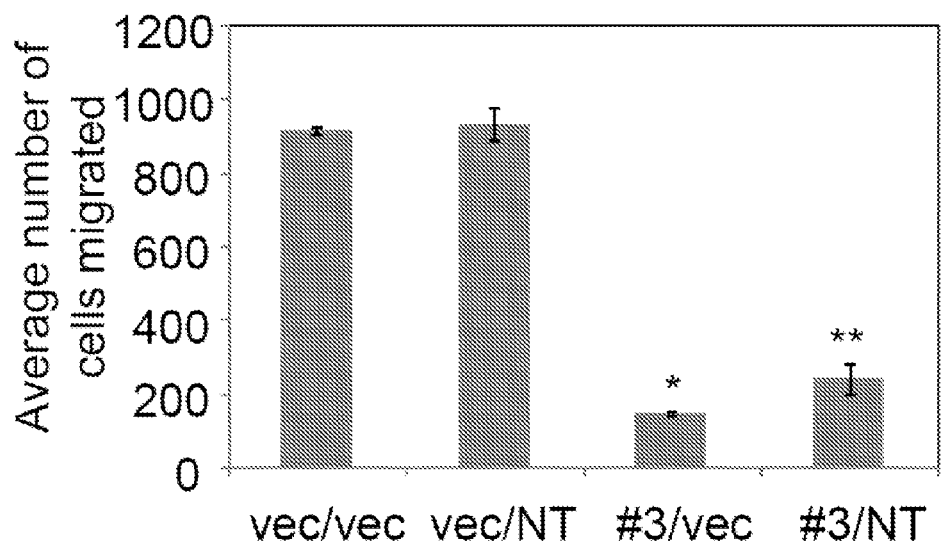

To determine whether similar results occur in vivo, melanoma cells harboring either WT or mutant GRM3 targeted with GRM3 or control shRNA were administered into Nu/Nu mice by subcutaneous injection. Nineteen days post-injection, depletion of GRM3 had little effect on in vivo growth of cells harboring WT GRM3. In contrast, GRM3 knockdown significantly reduced the tumor growth induced by cells harboring mutant GRM3. As the shRNA-mediated phenotypes could be due to specific or nonspecific effects, an exogenous, non-targetable WT GRM3 construct that harbors silent mutations in the region of GRM3 targeted by shRNA #3 was engineered to rescue the effects of knockdown of endogenous GRM3. Melanoma cells harboring the E573K (Glu573Lys) mutations stably expressing either control or GRM3 shRNA #3 construct were transduced either with the lentiviral non-targetable GRM3 construct or with the empty vector as control. To demonstrate that the non-targetable GRM3 is not knocked-down in the presence of GRM3 shRNA #3, HEK293T cells were transiently transfected and immunoblotted for FLAG-GRM3 and GAPDH as a loading control (FIG. 11A). Non-targetable GRM3 reconstituted cells showed significantly more migration (#3/NT) than cells infected with the control vector (#3/Vec) (FIG. 11B). These results suggest that certain GRM3 mutations are essential for cellular proliferation as well as cell migration in melanoma cells.

Figure 5A:
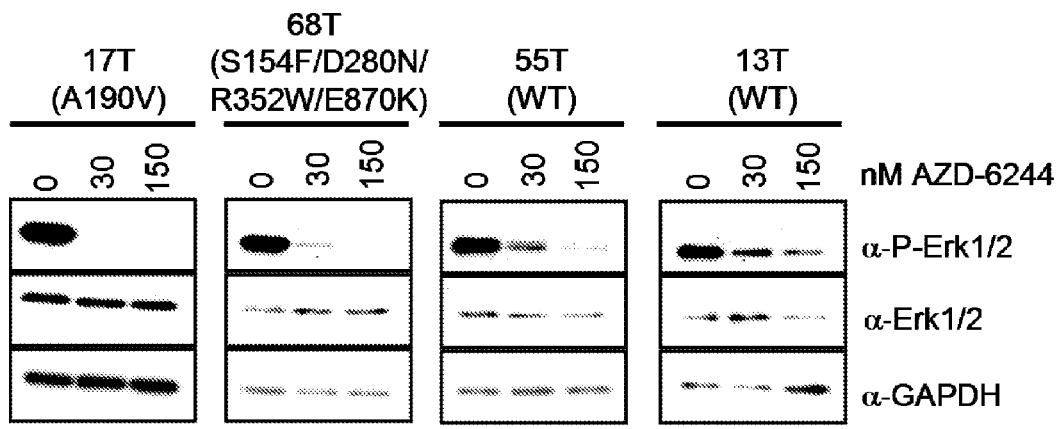
FIGS. 5A-5E: Melanoma lines expressing GRM3 mutants show increased sensitivity to inhibition of MEK by AZD-6244.
Figure 5B:
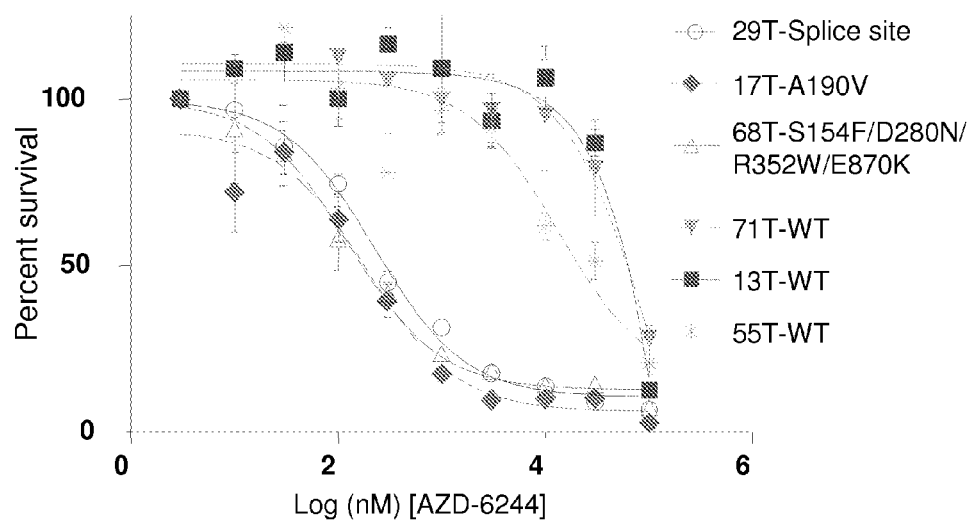
Figures 5C, 5E:
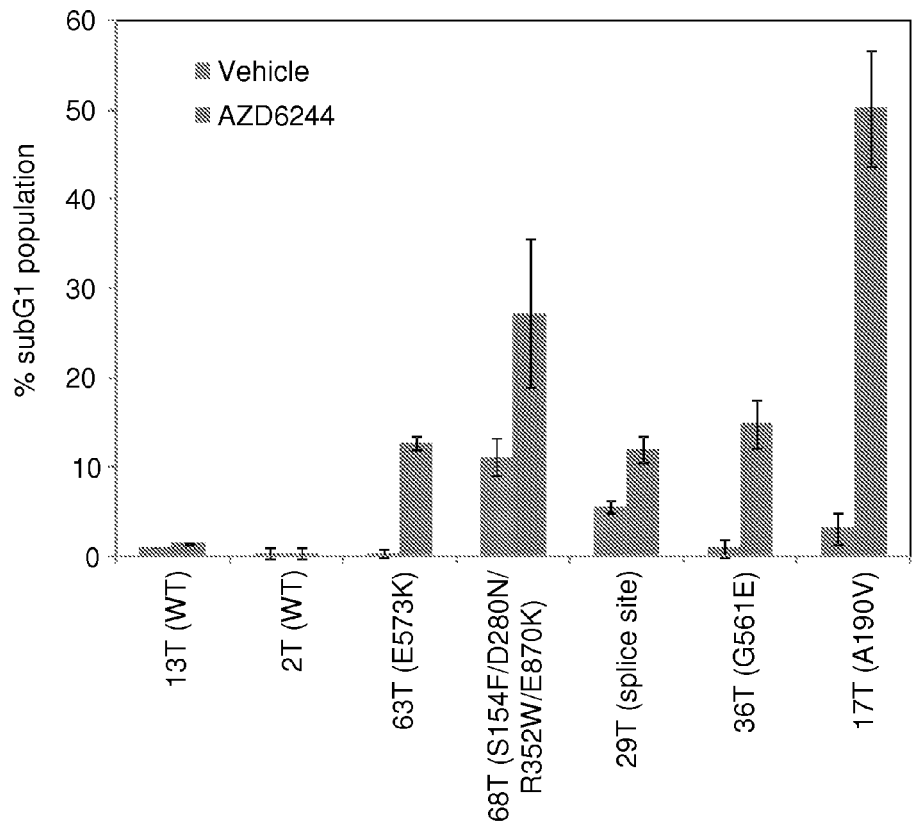

To evaluate whether inhibition of GRM3 signaling would result in a similar phenotype to depletion of endogenous GRM3, melanoma cells harboring either WT GRM3 or mutant GRM3 were exposed to AZD-6244 (Selumetinib, ARRY-142886), which is a selective, non-ATP-competitive small molecule inhibitor of MEK-1/2 that is now being tested in phase II clinical trials. Exposure of melanoma cells to AZD-6244 inhibited MEK (as measured by phosphorylated ERK (p-ERK) levels) in mutant as well as WT cells (FIG. 5A). However, the relative degree of inhibition was greater for the mutant cells than for the WT cells. This suggested that mutant cells would be more sensitive to growth inhibition by AZD-2688 than WT cells. Indeed, exposure of melanoma cells expressing mutant forms of GRM3 were 10- to 200-fold more sensitive to AZD-6244 compared with WT GRM3 cells (FIGS. 5B and 5C).

Figure 12A:
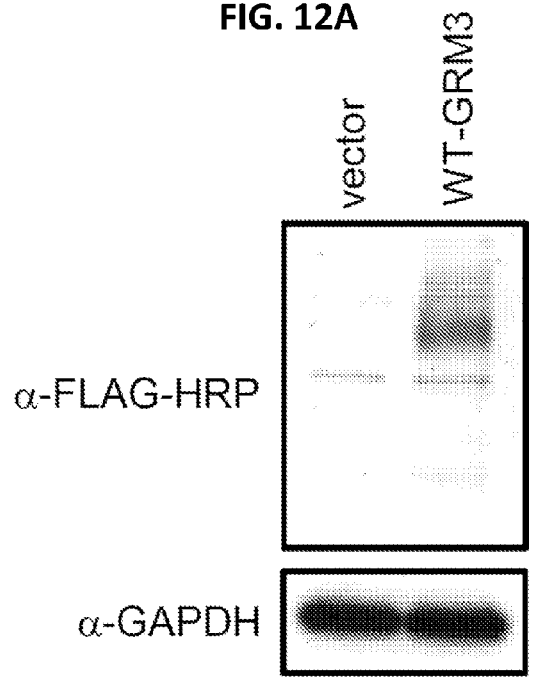
Figure 12B:
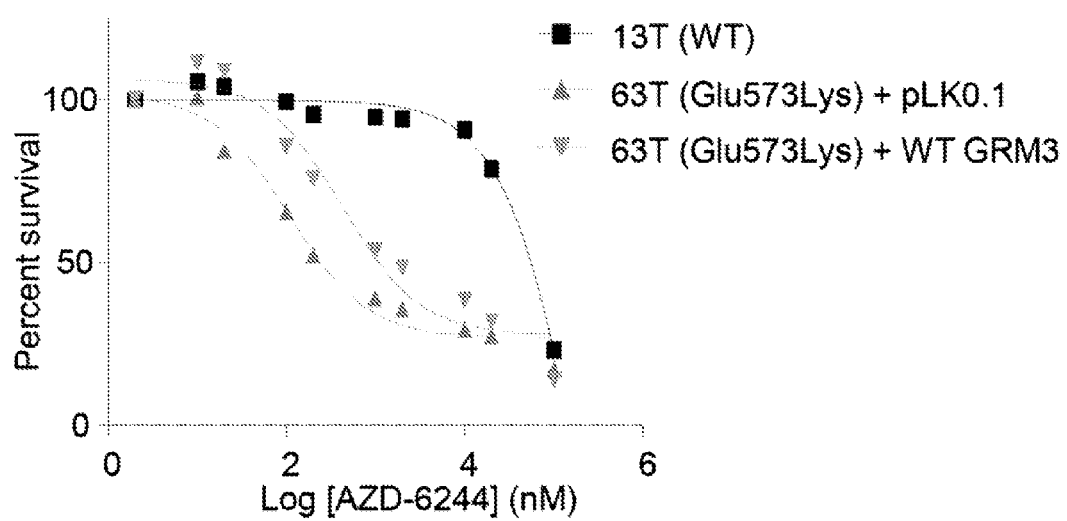

The GRM3 mutations may be dependent on MEK signaling via BRAF as seen by the genotypes of the investigated cells (Table 8). To further investigate the relevance of mutant GRM3 to AZD-6244 sensitivity, whether the sensitivity to MEK inhibition can be altered by modulating GRM3 was investigated. To do this, a stable cell line overexpressing WT GRM3 in a mutant GRM3 background was established (FIG. 12A). Exposure of these stable pools to AZD-6244 resulted in reduced cell proliferation with a four-fold increased resistance in cells overexpressing WT GRM3 compared to control infected cells (FIGS. 12B-12C). These results further suggest that AZD-6244 preferentially inhibits the signaling of cells expressing mutant GRM3.

Figure 5D:
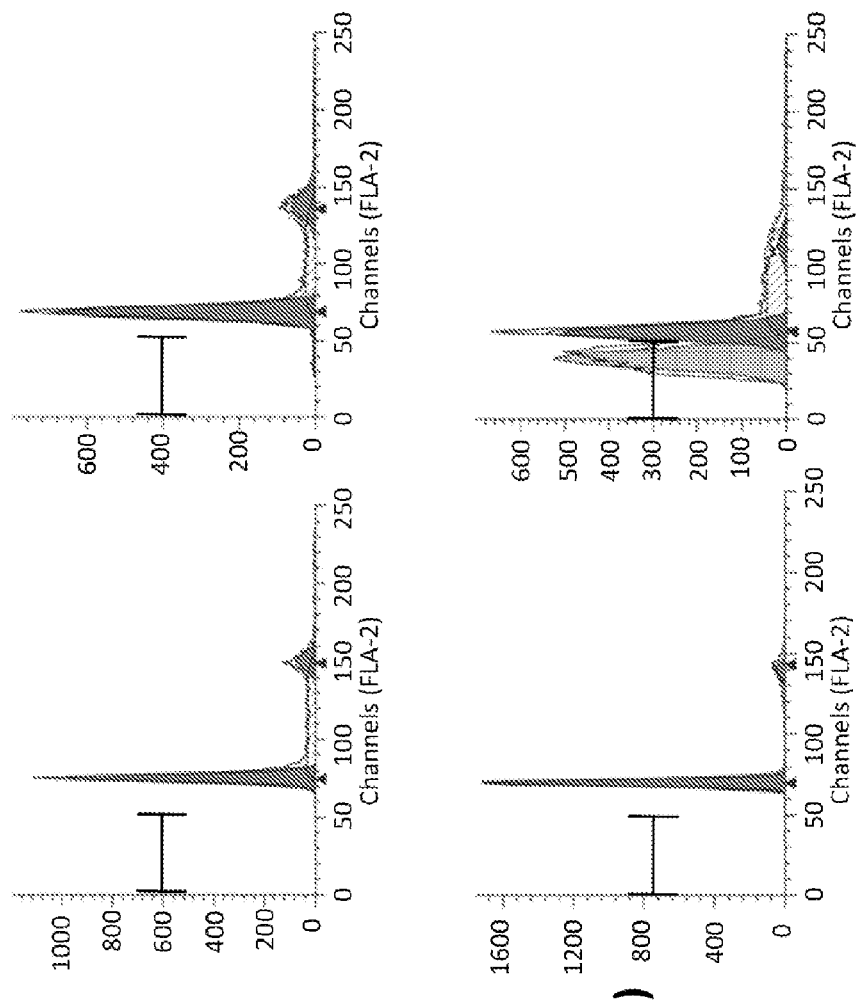

The decreased growth of the mutant cells in the presence of AZD-6244 could have arisen either through alterations to the cell cycle or through increased cell death. To establish which mechanism was underlying this phenotype, cell cycle was assessed through FACS analysis. It was found that cells harboring mutant GRM3 exhibited a significant increase in the levels of subG1 population (apoptotic cells) compared to WT cells (FIG. 5D). Similar results were observed when the experiment was performed on a larger panel of mutant GRM3 cell lines (FIG. 5E, t-test $p<0.05$). Inhibition of MEK1/2 by AZD-6244 clearly triggered apoptotic events, as a western blot analysis of cell lysates from FACS analyzed cells showed increased levels of cleaved PARP in mutant lines compared to WT cells (FIG. 5F). Collectively, these results demonstrate that melanoma cell lines harboring mutant forms of GRM3 are significantly more sensitive to MEK1/2 inhibition by AZD-6244 leading to increased cell death or apoptosis.

The high frequency of mutations found in GRM3, the finding of a mutational hotspot as well as the functional assays, suggest GRM3 to be an important driver in melanoma. Taken together, the data described above highlights a model for melanoma pathogenesis in which activation of MEK by GRM3 mutations promotes the survival and migration of melanoma cells. In addition, it is contemplated herein that the presence of GRM3 mutations is an indicator of patient subpopulations whose tumors are dependent on MEK signaling. The prior failure of MEK inhibitors to obtain significant tumor responses in many $BRAF^{V600E}$ melanomas (McDermott et al., *J Clin Oncol* 26:2178-2185, 2008; Rinehart et al., *J Clin Oncol* 22:4456-4462, 2004) may have resulted at least in part from the presence of additional mutations that activate the MEK pathway, such as GRM3. Therefore, targeting MEK signaling in the presence of GRM3 mutations can be used for the treatment of melanoma.

TABLE 1

Mutations Identified in GPCRs (4 pages)

| Gene | Other names | CCDS accession* | Ref Seq accession* | No. of mutations (% tumors affected)# | Tumor | Exon | Nucleo-tide† | Amino Acid† | Functional domain‡ |
|---|---|---|---|---|---|---|---|---|---|
| GRM3 | GLUR3 | 5600.1 | NM_000840 | 18 (16.3%) | 85T | 1 | G53A | G18E | N/A |
| | GPRC1C | | | | 21T | 1 | G176A | R59Q | PBP1_mGluRgroupII |
| | MGLUR3 | | | | 76T | 1 | G263A | G88E | PBP1_mGluRgroupII |
| | mGlu3 | | | | 68T | 1 | C461T | S154F | PBP1_mGluRgroupII |
| | | | | | 85T | 2 | C575T | P192L | PBP1_mGluRgroupII |
| | | | | | 68T | 2 | G838A | D280N | PBP1_mGluRgroupII |
| | | | | | 68T | 2 | C1054T | R352W | PBP1_mGluRgroupII |
| | | | | | 29T | 3 | T/C (−13) | Splice Site | PBP1_mGluRgroupII |
| | | | | | 6T | 3 | G1402T | V468L | PBP1_mGluRgroupII |
| | | | | | 98T | 3 | G1531A | D511N | NCD3G |
| | | | | | 39T | 3 | G1549A | E517K | NCD3G |
| | | | | | 7T | 3 | G1642A | D548N | NCD3G |
| | | | | | 36T | 3 | G1682A | G561E | N/A |
| | | | | | 63T | 3 | G1717A | E573K | N/A |
| | | | | | 76T | 3 | C1829T | S610L | 7TM_3 |
| | | | | | 32T | 3 | G2299A | E767K | 7TM_3 |
| | | | | | 22T | 4 | G2543A | G848E | N/A |
| | | | | | 68T | 5 | G2608A | E870K | N/A |
| CHRM3 | HM3 | 1616.1 | NM_000740 | 8 (10.0%) | 34T | 1 | C74T | S25F | N/A |
| | | | | | 39T | 1 | G94A | G32R | N/A |
| | | | | | 7T | 1 | G599A | W200X | 7TM_1 |
| | | | | | 21T | 1 | C1261T | P421S | 7TM_1 |
| | | | | | 91T | 1 | C1262T | P421L | 7TM_1 |
| | | | | | 12T | 1 | C1282T | P428S | 7TM_1 |
| | | | | | 100T | 1 | A1330C | N444H | 7TM_1 |
| | | | | | 19T | 1 | T1741A | F581I | N/A |
| LPHN2 | CIRL2 | 689.1 | NM_012302 | 10 (8.8%) | 85T | 4 | C529T | P177S | OLF |
| | CL2 | | | | 48T | 4 | C563T | S188F | OLF |
| | LEC1 | | | | 80T | 4 | T1057C | Y353H (LOH) | OLF |
| | LPHH1 | | | | 76T | 7 | G1609A | E537K | N/A |
| | | | | | 39T | 10 | C2225T | S742L | N/A |
| | | | | | 76T | 13 | G2896A | E966K (LOH) | 7TM_2 |
| | | | | | 63T | 16 | C3116T | S1039F | 7TM_2 |
| | | | | | 13T | 18 | C3422T | S1141L | Latrophilin |
| | | | | | 76T | 19 | G3618A | M1206I | Latrophilin |
| | | | | | 63T | 19 | G3992A | S1331N | Latrophilin |
| RXFP1 | LGR7 | 43276.1 | NM_021634 | 8 (7.5%) | 104T | 4 | C365T | P122L | N/A |
| | LGR7.1 | | | | 7T | 4 | C368T | S123L | N/A |
| | LGR7.10 | | | | 76T | 10 | C806T | S269F | N/A |
| | LGR7.2 | | | | 104T | 10 | C806T | S269F | N/A |
| | MGC138347 | | | | 55T | 16 | C1405T | R469C | 7TM_1 |

TABLE 1-continued

Mutations Identified in GPCRs (4 pages)

| Gene | Other names | CCDS accession* | Ref Seq accession* | No. of mutations (% tumors affected)# | Tumor | Exon | Nucleo-tide† | Amino Acid† | Functional domain‡ |
|---|---|---|---|---|---|---|---|---|---|
| | MGC142177 | | | | 55T | 16 | G1525A | E509K | 7TM_1 |
| | RXFPR1 | | | | 13T | 16 | C1636T | P546S | 7TM_1 |
| | | | | | 85T | 17 | G1837A | A613T (LOH) | 7TM_1 |
| GRM8 | FLJ41058 | 5794.1 | NM_000845 | 8 (8.8%) | 76T | 1 | C/T (−11) | Splice Site | N/A |
| | GLUR8 | | | | 55T | 1 | T143A | L48X | N/A |
| | GPRC1H | | | | 34T | 3 | C776T | P259L | ANF_R |
| | MGC126724 | | | | 95T | 7 | G1387A | E463K | ANF_R |
| | MGLUR8 | | | | 29T | 7 | G1394A | G465E | ANF_R |
| | mGlu8 | | | | 17T | 8 | C1946T | S649F | 7TM_3 |
| | | | | | 76T | 8 | T2318A | V773D (LOH) | 7TM_3 |
| | | | | | 85T | 10 | C2681T | S894F | N/A |
| CNR1 | RP1-23D17.1 | 5015.1 | NM_016083 | 6 (6.3%) | 104T | 1 | G28C | D10H | N/A |
| | CANN6 | | | | 19T | 1 | C145T | P49S | N/A |
| | CB-R | | | | 71T | 1 | G659A | R220K | 7TM_1 |
| | CB1 | | | | 76T | 1 | G765A | W255X | 7TM_1 |
| | CB1A | | | | 64T | 1 | A905C | H302P (LOH) | 7TM_1 |
| | CB1K5 | | | | 64T | 1 | C919T | R307C (LOH) | 7TM_1 |
| | CB1R | | | | | | | | |
| | CNR | | | | | | | | |
| OR1J2 | RP11-542K23.4 | 35121.1 | NM_054107 | 4 (5.0%) | 85T | 1 | G325A | D109N (LOH) | 7TM_1 |
| | FLJ16828 | | | | 36T | 1 | G325A | D109N | 7TM_1 |
| | HG152 | | | | 72T | 1 | C467T | S156F | 7TM_1 |
| | HSA5 | | | | 23T | 1 | C730T | H244Y (LOH) | 7TM_1 |
| | OR1J6 | | | | | | | | |
| | OR1J5 | | | | | | | | |
| | OR9-19 | | | | | | | | |
| | OST044 | | | | | | | | |
| OR8B8 | TPCR85 | 8446.1 | NM_012378 | 6 (5.0%) | 55T | 1 | C221T | S74F(LOH) | 7TM_1 |
| | | | | | 76T | 1 | C221T | S74F(LOH) | 7TM_1 |
| | | | | | 74T | 1 | G361A | D121N | 7TM_1 |
| | | | | | 76T | 1 | C412T | P138S | 7TM_1 |
| | | | | | 1T | 1 | G885T | K295N | N/A |
| | | | | | 1T | 1 | G925T | A309S | N/A |
| OPN5 | NEUROPSIN | 4923.1 | NM_181744 | 3 (3.8%) | 90T | 3 | C278A | S93Y | 7TM_1 |
| | PGR12 | | | | 85T | 4 | C545T | S182L | 7TM_1 |
| | TMEM13 | | | | 64T | 6 | C1007T | T336I | N/A |
| OR8K1 | OR11-182 | 31528.1 | NM_001002907 | 2 (2.5%) | 36T | 1 | C409A | L137M | 7TM_1 |
| | OR8N1P | | | | 13T | 1 | T770C | F257L | 7TM_1 |
| GPR98 | DKFZp761P0710 | 47246.1 | NM_032119 | 43 (27.5%) | 85T | 7 | C853T | R285C | N/A |
| | FEB4 | | | | 76T | 14 | G2570A | W857X | N/A |
| | KIAA0686 | | | | 104T | 20 | C3925T | P1309S | 1309 |
| | MASS1 | | | | 37T | 24 | C5282T | S1761F | Calx-beta |
| | USH2B | | | | 76T | 26 | C5515T | H1839Y | N/A |
| | USH2C | | | | 1T | 28 | G5815A | E1939K | Calx-beta |
| | VLGR1 | | | | 55T | 28 | G6229A | E2077K | Calx-beta |
| | VLGR1b | | | | 77T | 31 | C6901T | Q2301X | N/A |
| | | | | | 92T | 31 | C6905T | T2302I | N/A |
| | | | | | 39T | 33 | C7330T | L2444F (LOH) | N/A |
| | | | | | 58T | 34 | A8093T | N2698I | N/A |
| | | | | | 45T | 35 | G8201A | G2734E | N/A |
| | | | | | 76T | 37 | G8461A | E2821K | N/A |
| | | | | | 76T | 42 | C9049T | H3017Y | Calx-beta |
| | | | | | 4T | 42 | C9109T | P3037S | N/A |
| | | | | | 21T | 44 | C9524T | T3175I | N/A |
| | | | | | 81T | 45 | C9679T | R3227X (LOH) | N/A |
| | | | | | 17T | 46 | G9826A | E3276K | N/A |
| | | | | | 63T | 50 | C10472T | S3491F | N/A |
| | | | | | 76T | 52 | G10789A | E3597K | Calx-beta |
| | | | | | 85T | 52 | G10852A | E3618K | Calx-beta |
| | | | | | 85T | 52 | G10888A | G3630R | N/A |
| | | | | | 55T | 53 | G11087A | E3696E | N/A |
| | | | | | 17T | 53 | C11107T | P3703S | N/A |
| | | | | | 18T | 55 | G11563A | E3855K | N/A |
| | | | | | 37T | 57 | G11869A | A3957T | N/A |
| | | | | | 44T | 61 | G12425A | R4142Q | N/A |
| | | | | | 44T | 61 | G12426A | R4142Q | N/A |
| | | | | | 17T | 62 | G12595A | G4199R | N/A |
| | | | | | 1T | 65 | C13151T | S4384F | N/A |
| | | | | | 55T | 69 | G14032A | G4678R | N/A |
| | | | | | 71T | 73 | G14837A | G4946E | N/A |
| | | | | | 44T | 73 | C14846T | S4949L | N/A |
| | | | | | 76T | 74 | G15106A | D5036N (LOH) | N/A |
| | | | | | 21T | 74 | G15376A | D5126N | N/A |

TABLE 1-continued

Mutations Identified in GPCRs (4 pages)

| Gene | Other names | CCDS accession* | Ref Seq accession* | No. of mutations (% tumors affected)# | Tumor | Exon | Nucleotide† | Amino Acid† | Functional domain‡ |
|---|---|---|---|---|---|---|---|---|---|
| | | | | | 76T | 74 | T15398A | M5133K | N/A |
| | | | | | 76T | 74 | C15407T | S5136F | N/A |
| | | | | | 34T | 74 | C15644T | S5215F | N/A |
| | | | | | 76T | 74 | G15688A | E5230K | N/A |
| | | | | | 33T | 74 | G15832A | G5278S | N/A |
| | | | | | 76T | 79 | C17041T | Q5681X | N/A |
| | | | | | 74T | 78 | G16825A | D5609N | N/A |
| | | | | | 21T | 84 | C17965T | L5989F | 7TM_2 |

*Accession numbers for mutated GPCR in Santa Cruz and GenBank.
Number of non-synonymous and splice site mutations observed and percent of tumors affected for each of the 11 genes in the panel of 80 melanoma cancers.
†Nucleotide and amino acid change resulting from mutation.
"X" refers to stop codon. "LOH" refers to cases wherein the wild-type allele was lost and only the mutant allele remained.
"Splice site" refers to a case wherein the alteration affected fifteen bases spanning the exon.
**Mutations previously observed in NRAS, BRAF.
"None" refers to mutation observed.
PBP1_mGluR_groupII: Receptor family ligand binding region; HRM: hormone receptor domain; Gal_Lectin: galactose binding lectin domain; GPS: latrophilin/CL-1-like GPS domain.
Latrophilin: latrophilin cytoplasmic C-terminal region; Ldl_R_a: low-density lipoprotein receptor domain class A; LRR_1: leucine rich repeat; NCD3G: 9 cysteines domain of family 3 GPCR
OLF: olfactomedin-like domain; Calx-beta: Calx-beta domain; EPTP: EPTP domain; GPS: latrophilin/CL-1-like GPS domain

TABLE 2

Somatic Mutations Identified in GPCR genes

| Gene | CCDS accession* | Ref Seq accession* | Gene Name | Tumor | Nucleotide† | Amino Acid† |
|---|---|---|---|---|---|---|
| ADCYAP1R1 | NM_00118 | CCDS5433.1 | adenylate cyclase activating polypeptide 1 | 85T | C934T | P312S |
| CCR3 | NM_001837 | CCDS2738.1 | chemokine receptor 3 | 13T | G358A | E120K |
| CHRM3 | NM_000740 | CCDS1616.1 | cholinergic receptor, muscarinic 3 | 34T | C74T | S25F |
| CHRM3 | NM_000740 | CCDS1616.1 | cholinergic receptor, muscarinic 3 | 7T | G599A | W200X |
| CNR1 | NM_033181 | CCDS5016.1 | central cannabinoid receptor | 19T | C145T | P49S |
| CNR1 | NM_033181 | CCDS5016.1 | central cannabinoid receptor | 64T | C919T | R307C (LOH) |
| CNR2 | NM_001841 | CCDS245.1 | cannabinoid receptor 2 (macrophage) | 1T | G43A | D15N |
| FSHR | NM_181446 | CCDS1844.1 | follicle stimulating hormone receptor | 13T | C856T | P348S |
| FZD3 | NM_017412 | CCDS6069.1 | frizzled 3 | 34T | C497T | P166L |
| GHSR | NM_198407 | CCDS3216.1 | growth hormone secretagogue receptor | 13T | G847A | R283Q (LOH) |
| GPR112 | NM_153834 | CCDS35409.1 | G-protein coupled receptor 112 | 64T | C8102T | S2701F |
| GPR116 | NM_001098518 | CCDS4919.1 | G-protein coupled receptor 116 | 17T | C799T | Q267X |
| GPR174 | NM_032553 | CCDS14443.1 | putative purinergic receptor FKSG79 | 64T | C953T | S318F |
| GPR98 | NM_032119 | n/a | G-protein-coupled receptor 98 precursor | 85T | C853T | R285C |
| GPR98 | NM_032119 | n/a | G-protein-coupled receptor 98 precursor | 1T | G5815A | E1939K |
| GPRC5A | NM_003979 | CCDS8657.1 | G-protein-coupled receptor, family C, group 5, member A | 13T | C514T | R172C |
| GPRC6A | NM_148963 | CCDS5112.1 | G-protein-coupled receptor, family C, group 6, member A | 17T | G292A | E98K |
| GRM3 | NM_000840 | CCDS5600.1 | glutamate receptor, metabotropic 3 precursor | 85T | G53A | G18E |
| GRM3 | NM_000840 | CCDS5600.1 | glutamate receptor, metabotropic 3 precursor | 7T | G1642A | D548N |
| GRM7 | NM_181874 | CCDS2567.1 | glutamate receptor, metabotropic 7 | 7T | A2028T | K676N |
| GRM8 | NM_000845 | CCDS5794.1 | glutamate receptor, metabotropic 8 isoform a | 34T | C776T | P259L |
| GRM8 | NM_000845 | CCDS5794.1 | glutamate receptor, metabotropic 8 | 85T | C2681T | S894F |
| HTR1E | NM_000865 | CCDS5006.1 | 5-hydroxytryptamine (serotonin) receptor 1E | 1T | C799T | P267S |
| HTR2C | NM_000868 | CCDS14564.1 | 5-hydroxytryptamine (serotonin) receptor 2C | 95T | G239A | M80I |
| IL8RB | NM_001557 | CCDS2408.1 | interleukin 8 receptor beta | 36T | G271T | A91S (LOH) |
| LGR4 | NM_018490 | CCDS31449.1 | leucine-rich repeat-containing G protein-coupled receptor 4 | 13T | G409A | D137N |
| LGR5 | NM_003667 | CCDS9000.1 | leucine-rich repeat-containing G protein-coupled receptor 5 | 64T | C1534T | L512F |
| LPHN2 | NM_012302 | CCDS689.1 | latrophilin 2 | 85T | C529T | P177S |
| LPHN2 | NM_012302 | CCDS689.1 | latrophilin 2 | 13T | C3422T | S1141L |
| LPHN3 | NM_015236 | n/a | latrophilin 3 | 1T | C1229T | S410F |
| MC2R | NM_000529 | CCDS11869.1 | melanocortin 2 receptor | 85T | C518T | P173L (LOH) |
| MC2R | NM_000529 | CCDS11869.1 | melanocortin 2 receptor | 85T | G958A | G320R |
| NMUR2 | NM_020167 | CCDS4321.1 | neuromedin U receptor 2 | 64T | C893T | S298F |
| NPFFR2 | NM_004885 | CCDS3551.1 | neuropeptide FF receptor 2 isoform 1 | 13T | A1480G | T494A |

TABLE 2-continued

Somatic Mutations Identified in GPCR genes

| Gene | CCDS accession* | Ref Seq accession* | Gene Name | Tumor | Nucleotide† | Amino Acid† |
|---|---|---|---|---|---|---|
| OPN3 | NM_014322 | CCDS31072.1 | opsin 3 | 7T | C1398T | R400C |
| OPN5 | NM_181744 | CCDS4923.1 | opsin 5 | 85T | C545T | S182L |
| OPN5 | NM_181744 | CCDS4923.1 | opsin 6 | 64T | C1007T | T336I |
| OR10A3 | NM_001003745 | CCDS31421.1 | olfactory receptor, family 10, subfamily A, member 3 | 34T | G517A | E173K |
| OR10A6 | NM_001004461 | CCDS31420.1 | olfactory receptor, family 10, subfamily A, member 6 | 13T | G906A | M302I |
| OR10AG1 | NM_001005491 | CCDS31514.1 | olfactory receptor, family 10, subfamily AG, member 1 | 13T | C797T | S266F |
| OR10J1 | NM_012351 | CCDS1185.1 | olfactory receptor, family 10, subfamily J, member 1 | 85T | G388A | G130R (LOH) |
| OR10W1 | NM_207374 | CCDS7968.1 | olfactory receptor, family 10, subfamily W, member 1 | 13T | G176A | G59E |
| OR13C2 | NM_001004481 | CCDS35092.1 | olfactory receptor, family 13, subfamily C, member 2 | 17T | C569T | A190V |
| OR13C3 | NM_001001961 | CCDS35089.1 | olfactory receptor, family 13, subfamily C, member 3 | 36T | G160A | E54K |
| OR13C8 | NM_001004483 | CCDS35090.1 | olfactory receptor, family 13, subfamily C, member 8 | 1T | G698A | G233E |
| OR13C9 | NM_001001956 | CCDS35093.1 | olfactory receptor, family 13, subfamily C, member 9 | 13T | C378T | S93F |
| OR13G1 | NM_001005487 | CCDS31094.1 | olfactory receptor, family 13, subfamily G, member 1 | 13T | G65A | G22E |
| OR14A16 | NM_001001966 | CCDS31097.1 | olfactory receptor, family 14, subfamily A, member 16 | 85T | C749T | S250F (LOH) |
| OR1E2 | NM_003554 | CCDS11026.1 | olfactory receptor, family 1, subfamily E, member 2 | 95T | C386T | P129L (LOH) |
| OR1J2 | NM_054107 | CCDS35121.1 | olfactory receptor, family 1, subfamily J, member 2 | 85T | G325A | D109N (LOH) |
| OR1J2 | NM_054107 | CCDS35121.1 | olfactory receptor, family 1, subfamily J, member 2 | 36T | G325A | D109N |
| OR1L1 | NM_001005236 | CCDS35127.1 | olfactory receptor, family 1, subfamily L, member 1 | 1T | C220T | Q74X |
| OR1L3 | NM_001005234 | CCDS35128.1 | olfactory receptor, family 1, subfamily L, member 3 | 17T | G812A | R271Q |
| OR1L6 | NM_001004453 | CCDS35130.1 | olfactory receptor, family 1, subfamily L, member 6 | 85T | G442A | D148N |
| OR1N1 | NM_012363 | CCDS6844.1 | olfactory receptor, family 1, subfamily N, member 1 | 7T | A871G | R291G (LOH) |
| OR2A25 | NM_001004488 | CCDS43669.1 | olfactory receptor, family 2, subfamily A, member 25 | 13T | T634G | S212A |
| OR2A5 | NM_012365 | CCDS43668.1 | olfactory receptor, family 2, subfamily A, member 5 | 13T | C859T | P287S |
| OR2AT4 | NM_001005285 | CCDS31639.1 | olfactory receptor, family 2, subfamily AT, member 4 | 7T | C694T | R232C |
| OR2B2 | NM_033057 | CCDS4641.1 | olfactory receptor, family 2, subfamily B, member 2 | 85T | C101T | S34F |
| OR2G3 | NM_001001914 | CCDS31093.1 | olfactory receptor, family 2, subfamily G, member 3 | 34T | G891A | M297I |
| OR2G6 | NM_001013355 | CCDS31119.1 | olfactory receptor, family 2, subfamily G, member 6 | 13T | G794A | R265K |
| OR2T1 | NM_030904 | CCDS31115.1 | olfactory receptor, family 2, subfamily T, member 1 | 85T | A1007G | N336S |
| OR2T3 | NM_001005495 | CCDS31117.1 | olfactory receptor, family 2, subfamily T, member 3 | 7T | G942A | M314I |
| OR4A47 | NM_001005512 | CCDS31490.1 | olfactory receptor, family 4, subfamily A, member 47 | 1T | C5156T | I305T |
| OR4C15 | NM_001001920 | CCDS31501.1 | olfactory receptor, family 4, subfamily C, member 15 | 7T | C523T | R175C |
| OR4K13 | NM_001004714 | CCDS32028.1 | olfactory receptor, family 4, subfamily K, member 13 | 36T | T772C | Y258H |
| OR4K17 | NM_001004715 | CCDS32030.1 | olfactory receptor, family 4, subfamily K, member 17 | 16T | C277T | L93F |
| OR4K2 | NM_001005501 | CCDS32023.1 | olfactory receptor, family 4, subfamily K, member 2 | 7T | C170T | S57F |
| OR4N5 | NM_001004724 | CCDS32031.1 | olfactory receptor, family 4, subfamily N, member 5 | 17T | G704A | W235X |
| OR4X2 | NM_001004727 | CCDS31486.1 | olfactory receptor, family 4, subfamily X, member 2 | 13T | A300G | Y267C |
| OR51B2 | NM_033180 | CCDS31377.1 | olfactory receptor, family 51, subfamily B, member 2 | 85T | C160T | H54Y (LOH) |
| OR51B4 | NM_033179 | CCDS7757.1 | olfactory receptor, family 51, subfamily B, member 4 | 17T | G760A | G254R |
| OR51F1 | NM_001004752 | CCDS31359.1 | olfactory receptor, family 51, subfamily F, member 1 | 85T | C422T (LOH) | S141F (LOH) |

TABLE 2-continued

Somatic Mutations Identified in GPCR genes

| Gene | CCDS accession* | Ref Seq accession* | Gene Name | Tumor | Nucleotide† | Amino Acid† |
|---|---|---|---|---|---|---|
| OR51L1 | NM_001004755 | CCDS31369.1 | olfactory receptor, family 51, subfamily L, member 1 | 13T | C793T | R265C |
| OR52A1 | NM_012375 | CCDS31374.1 | olfactory receptor, family 52, subfamily A, member 1 | 13T | G503A | R168Q |
| OR52H1 | NM_001005289 | CCDS31386.1 | olfactory receptor, family 52, subfamily H, member 1 | 64T | G265A | A89T (LOH) |
| OR52N4 | NM_001005175 | n/a | olfactory receptor, family 52, subfamily N, member 4 | 1T | T221A | V74D |
| OR5AC2 | NM_054106 | CCDS33796.1 | olfactory receptor, family 5, subfamily AC, member 2 | 16T | G160A | D54N |
| OR5B12 | NM_001004733 | CCDS31551.1 | olfactory receptor, family 5, subfamily B, member 12 | 1T | C553T | L185F (LOH) |
| OR5B21 | NM_001005218 | CCDS31552.1 | olfactory receptor, family 5, subfamily B, member 21 | 85T | G277A | D93N |
| OR5B3 | NM_001005469 | CCDS31549.1 | olfactory receptor, family 5, subfamily B, member 3 | 19T | G805A | D269N (LOH) |
| OR5L2 | NM_001004739 | CCDS31511.1 | olfactory receptor, family 5, subfamily L, member 2 | 7T | C719T | T240I |
| OR5M3 | NM_001004742 | CCDS31532.1 | olfactory receptor, family 5, subfamily M, member 3 | 13T | C379T | P127S |
| OR5V1 | NM_030876 | CCDS4657.1 | olfactory receptor, family 5, subfamily V, member 1 | 36T | G886A | D296N |
| OR6C3 | NM_054104 | CCDS31819.1 | olfactory receptor, family 6, subfamily C, member 3 | 17T | G692A | R231K |
| OR6C4 | NM_001005494 | CCDS31827.1 | olfactory receptor, family 6, subfamily C, member 4 | 95T | C167T | P56L (LOH) |
| OR6C74 | NM_001005490 | CCDS31816.1 | olfactory receptor, family 6, subfamily C, member 74 | 16T | C542T | P181L |
| OR6C75 | NM_001005497 | CCDS31820.1 | olfactory receptor, family 6, subfamily C, member 75 | 17T | G493A | D165N |
| OR6N2 | NM_001005278 | CCDS30906.1 | olfactory receptor, family 6, subfamily N, member 2 | 85T | G323A | G108E |
| OR7A17 | NM_030901 | CCDS12319.1 | olfactory receptor, family 7, subfamily A, member 17 | 13T | C387T | P129L |
| OR7G1 | NM_001005192 | CCDS32898.1 | olfactory receptor, family 7, subfamily G, member 1 | 85T | C569T | S190F |
| OR8B8 | NM_012378 | CCDS8446.1 | olfactory receptor, family 8, subfamily B, member 8 | 1T | G885T | K295N |
| OR8B8 | NM_012378 | CCDS8446.1 | olfactory receptor, family 8, subfamily B, member 8 | 1T | G925T | A309S |
| OR8K1 | NM_001002907 | CCDS31528.1 | olfactory receptor, family 8, subfamily K, member 1 | 36T | C411A | L137M |
| OR8K1 | NM_001002907 | CCDS31528.1 | olfactory receptor, family 8, subfamily K, member 1 | 13T | T769C | F257L |
| OR9G4 | NM_001005284 | CCDS31537.1 | olfactory receptor, family 9, subfamily G, member 4 | 16T | C695T | S232F (LOH) |
| OR9K2 | NM_001005243 | CCDS31814.1 | olfactory receptor, family 9, subfamily K, member 2 | 34T | C928T | P310S |
| PTGFR | NM_000959 | CCDS686.1 | prostaglandin F receptor isoform a precursor | 1T | C86T | S29F |
| RXFP1 | NM_021634 | CCDS43276.1 | relaxin/insulin-like family peptide receptor 1 | 7T | C368T | S123L |
| RXFP1 | NM_021634 | CCDS43276.1 | relaxin/insulin-like family peptide receptor 1 | 13T | C1636T | P546S |
| RXFP1 | NM_021634 | CCDS43276.1 | relaxin/insulin-like family peptide receptor 1 | 85T | G1837A | A613T |
| SCTR | NM_002980 | CCDS2127.1 | secretin receptor precursor | 85T | G97A | D33N (LOH) |
| TAAR5 | NM_003967 | CCDS5156.1 | trace amine associated receptor 5 | 7T | C937T | R313W |
| TACR3 | NM_001059 | CCDS3664.1 | tachykinin receptor 3 | 85T | C775T | P259S (LOH) |
| TAS2R20 | NM_176889 | CCDS8639.1 | taste receptor, type 2, member 20 | 34T | G106A | V36I |
| TAS2R60 | NM_177437 | CCDS5885.1 | taste receptor, type 2, member 60 | 85T | C230T | T77I |
| TAS2R7 | NM_023919 | CCDS8631.1 | taste receptor, type 2, member 7 | 64T | C913T | R305C |

*Accession numbers for mutated GPCR in Santa Cruz and GenBank.
†Nucleotide and amino acid change resulting from mutation.
"X" refers to stop codon. "LOH" refers to cases wherein the wild-type allele was lost and only the mutant allele remained.

TABLE 3

GPCR genes harboring two or more somatic mutations

| Gene | CCDS accession* | Ref Seq accession* | Gene Name | Tumor | Nucleotide† | Amino Acid† |
|---|---|---|---|---|---|---|
| CHRM3 | NM_000740 | CCDS1616.1 | cholinergic receptor, muscarinic 3 | 34T | C74T | S25F |
| CHRM3 | NM_000740 | CCDS1616.1 | cholinergic receptor, muscarinic 3 | 7T | G599A | W200X |

TABLE 3-continued

GPCR genes harboring two or more somatic mutations

| Gene | CCDS accession* | Ref Seq accession* | Gene Name | Tumor | Nucleotide† | Amino Acid† |
|---|---|---|---|---|---|---|
| CNR1 | NM_033181 | CCDS5016.1 | central cannabinoid receptor | 19T | C145T | P49S |
| CNR1 | NM_033181 | CCDS5016.1 | central cannabinoid receptor | 64T | C919T | R307C (LOH) |
| GPR98 | NM_032119 | n/a | G protein-coupled receptor 98 precursor | 85T | C853T | R285C |
| GPR98 | NM_032119 | n/a | G protein-coupled receptor 98 precursor | 1T | G5815A | E1939K |
| GRM3 | NM_000840 | CCDS5600.1 | glutamate receptor, metabotropic 3 precursor | 85T | G53A | G18E |
| GRM3 | NM_000840 | CCDS5600.1 | glutamate receptor, metabotropic 3 precursor | 7T | G1642A | D548N |
| GRM8 | NM_000845 | CCDS5794.1 | glutamate receptor, metabotropic 8 isoform a | 34T | C776T | P259L |
| GRM8 | NM_000845 | CCDS5794.1 | glutamate receptor, metabotropic 8 | 85T | C2681T | S894F |
| LPHN2 | NM_012302 | CCDS689.1 | latrophilin 2 | 85T | C529T | P177S |
| LPHN2 | NM_012302 | CCDS689.1 | latrophilin 2 | 13T | C3422T | S1141L |
| OPN5 | NM_181744 | CCDS4923.1 | opsin 5 | 85T | C545T | S182L |
| OPN5 | NM_181744 | CCDS4923.1 | opsin 5 | 64T | C1007T | T336I |
| OR1J2 | NM_054107 | CCDS35121.1 | olfactory receptor, family 1, subfamily J, member 2 | 85T | G325A | D109N (LOH) |
| OR1J2 | NM_054107 | CCDS35121.1 | olfactory receptor, family 1, subfamily J, member 2 | 36T | G325A | D109N |
| OR8K1 | NM_001002907 | CCDS31528.1 | olfactory receptor, family 8, subfamily K, member 1 | 36T | C411A | L137M |
| OR8K1 | NM_001002907 | CCDS31528.1 | olfactory receptor, family 8, subfamily K, member 1 | 13T | T769C | F257L |
| RXFP1 | NM_021634 | CCDS43276.1 | relaxin/insulin-like family peptide receptor 1 | 7T | C368T | S123L |
| RXFP1 | NM_021634 | CCDS43276.1 | relaxin/insulin-like family peptide receptor 1 | 13T | C1636T | P546S |
| RXFP1 | NM_021634 | CCDS43276.1 | relaxin/insulin-like family peptide receptor 1 | 85T | G1837A | A613T |

*Accession numbers for mutated GPCR in Santa Cruz and GenBank.
†Nucleotide and amino acid change resulting from mutation.
"X" refers to stop codon.

TABLE 4

Somatic mutations identified in GRM3 in the melanoma validation panel

| Gene | Other names | CCDS accession* | Ref Seq accession* | No. of mutations (% tumors affected)# | Tumor | Exon | Nucleotide† | Amino Acid† | Functional domain‡ |
|---|---|---|---|---|---|---|---|---|---|
| GRM3 glutamate receptor, metabotropic 3 | GLUR3 GPRC1C MGLUR3 mGlu3 | 5600.1 | NM_000840 | 4 (8.5%) | B5_13326 | exon 1 | G289A | D97N | PBP1_mGluRgroupII |
|  |  |  |  |  | B5_13326 | exon 2 | G538A | D180N | PBP1_mGluRgroupII |
|  |  |  |  |  | B12_13738 | exon 2 | G1065A | W355X | PBP1_mGluRgroupII |
|  |  |  |  |  | 05MD_1430 | exon 5 | G2608A | E870K | N/A |
|  |  |  |  |  | C17_11550 | exon 5 | G2608A | E870K | N/A |

*Accession numbers for mutated GPCR in Santa Cruz and GenBank.
Number of non-synonymous and splice site mutations observed and percent of tumors affected for GRM3 in the panel of 47 melanoma cancers.
†Nucleotide and amino acid change resulting from mutation.
"X" refers to stop codon.
‡Abbreviations for the functional domains: PBP1_mGluR_groupII: Receptor family ligand binding region.

TABLE 5

Characteristics of melanoma patients with GPCR mutations

| Sample | Patient Age (years)* | Patient Gender | Tumor Source | Matched normal source |
|---|---|---|---|---|
| 1T† | 29 | F | Lung | Blood |
| 2T | 30 | M | Pectoral muscle | Blood |
| 3T | 18 | F | Forehead, subcutaneous | Blood |
| 4T | 33 | F | Supraclavicular, soft tissue | Blood |
| 4T | 34 | F | Lung | Blood |
| 5T | 47 | M | External iliac soft tissue | Blood |
| 6T | 42 | M | Neck, soft tissue | Blood |
| 7T† | 53 | M | Stomach | Blood |
| 8T | 61 | M | Inguinal soft tissue | Blood |
| 9T | 62 | M | Back, subcutaneous | Blood |
| 10T | 55 | M | Axillary soft tissue | Blood |
| 12T | 53 | M | Upper arm, subcutaneous | Blood |
| 13T† | 49 | M | Chest wall, subcutaneous | Blood |
| 15T | 39 | M | Thigh, subcutaneous | Blood |
| 16T† | 62 | M | Lung | Blood |
| 17T† | 33 | M | Shoulder, subcutaneous | Blood |
| 18T | 55 | M | Clavicle, soft tissue | Blood |
| 19T† | 49 | M | Scapula, subcutaneous | Blood |
| 20T | 58 | F | Axillary soft tissue | Blood |
| 21T | 59 | M | Omentum | Blood |
| 22T | 51 | M | Chest wall, subcutaneous | Blood |
| 23T | 44 | M | Lung | Blood |
| 24T | 49 | M | Axillary soft tissue | Blood |
| 26T | 48 | F | Lung | Blood |
| 28T | 28 | F | Axillary soft tissue | Blood |
| 29T | 51 | M | Inguinal soft tissue | Blood |
| 30T | 53 | F | Lung | Blood |
| 31T | 49 | F | Thigh, subcutaneous | Blood |
| 32T | 58 | M | Omentum | Blood |
| 33T | 33 | M | Chest wall subcutaneous, & pleura | Blood |

TABLE 5-continued

Characteristics of melanoma patients with GPCR mutations

| Sample | Patient Age (years)* | Patient Gender | Tumor Source | Matched normal source |
|---|---|---|---|---|
| 34T† | 31 | M | Shoulder, subcutaneous | Blood |
| 35T | 23 | F | Thigh, subcutaneous | Blood |
| 36T† | 25 | M | Thigh, subcutaneous | Blood |
| 37T | 38 | F | Omentum | Blood |
| 39T | 56 | M | Mesentery | Blood |
| 41T | 45 | M | Neck, soft tissue | Blood |
| 43T | 19 | F | Popliteal soft tissue | Blood |
| 44T | 56 | M | Lung | Blood |
| 45T | 48 | M | Mediastinum | Blood |
| 48T | 28 | M | Back, soft tissue | Blood |
| 49T | 43 | M | Thigh, subcutaneous | Blood |
| 50T | 49 | F | Inguinal soft tissue | Blood |
| 51T | 50 | F | Adnexa | Blood |
| 52T | 39 | F | Lung | Blood |
| 55T | 60 | M | Lung | Blood |
| 56T | 52 | M | Lung | Blood |
| 58T | 46 | F | Hip, subcutaneous | Blood |
| 59T | 64 | F | Abdomen, subcutaneous | Blood |
| 60T | 46 | M | Flank, subcutaneous | Blood |
| 62T | 58 | F | Thigh, subcutaneous | Blood |
| 63T | 30 | M | Jejunum | Blood |
| 64T† | 32 | F | Ovary | Blood |
| 68T | 49 | M | Lung | Blood |
| 69T | 36 | M | Axillary soft tissue | Blood |
| 71T | 67 | M | Lung | Blood |
| 72T | 53 | M | Liver | Blood |
| 73T | 45 | F | Breast | Blood |
| 74T | 40 | F | Lower extremity, subcutaneous | Blood |
| 76T | 40 | M | Neck, soft tissue | Blood |
| 77T | 39 | M | Lung | Blood |
| 78T | 27 | F | Lung | Blood |
| 80T | 36 | F | Popliteal soft tissue | Blood |
| 81T | 60 | F | Upper arm, subcutaneous | Blood |
| 83T | 33 | F | Back, subcutaneous | Blood |
| 84T | 60 | F | Thigh, subcutaneous | Blood |
| 85T† | 44 | M | Chest wall, subcutaneous | Blood |
| 86T | 42 | F | Liver | Blood |
| 88T | 37 | F | Chest wall, subcutaneous | Blood |
| 90T | 19 | M | Neck, soft tissue | Blood |
| 91T | 55 | F | Subcostal soft tissue | Blood |
| 92T | 37 | F | Femur | Blood |
| 94T | 44 | M | Adrenal gland | Blood |
| 95T† | 58 | F | Inguinal soft tissue | Blood |
| 96T | 49 | M | Inguinal soft tissue | Blood |
| 98T | 58 | F | Small Bowel | Blood |
| 99T | 57 | M | Liver | Blood |
| 100T | 28 | M | Chest wall, soft tissue | Blood |
| 103T | 35 | F | Axillary soft tissue | Blood |
| 104T | 56 | M | Thigh, subcutaneous | Blood |
| 105T | 28 | M | Neck, soft tissue | Blood |
| 106T | 41 | F | Lung | Blood |
| B5_13326 | 47 | F | Right axillary LN | Blood |
| B12_13738 | 72 | M | L neck LN | Blood |
| 05MD_14306 | 53 | M | Left axillary LN | Blood |
| C17_11550 | 67 | M | Left axillary LN | Blood |

*Patient's age when tumor was surgically removed.
Abbreviations:
F, female;
M, male.
†Tumor samples used in MIP capture

TABLE 6

Primers used for PCR amplification of the GRM3 gene (GRM3-CCDS accession 5600.1; Ref. Seq. accession NM 000840)

| Primer Exon | Forward Primer | SEQ ID NO: | Reverse Primer | SEQ ID NO: |
|---|---|---|---|---|
| GRM3-1 Exon 1 | CTAGCATGACACATTGGCTCC | 22 | AATGGCATAGGATCCATCAGG | 34 |
| GRM3-2 Exon 2 | AGAGAGTGTGGTGCCCTTCTC | 23 | CTGCAACAGTTCTCGGATCAC | 35 |
| GRM3-3 Exon 2 | GCTGAGATCTTGCGCTTCTTC | 24 | TGGACTCTTGCTCGTAGTTGC | 36 |
| GRM3-4 Exon 2 | GTGATCCGAGAACTGTTGCAG | 25 | TTTAAAGGCTCTTGGCTTACCC | 37 |
| GRM3-5 Exon 2 | GTTCGACCGCTACTTCCAGAG | 26 | GCACAGAGGCATTTGATTCC | 38 |
| GRM3-6 Exon 3 | CCTTGGAATCACCATTTCCTG | 27 | CCAGACCCACAATCCATACAG | 39 |
| GRM3-7 Exon 3 | CTTGAAAGTTGGTCACTGGGC | 28 | GCAATGCAGTTTGTCTTGGTC | 40 |
| GRM3-8 Exon 3 | AAGCACAACAACACACCCTTG | 29 | GATGCACGTGGTGTACATGG | 41 |
| GRM3-9 Exon 3 | CTGCTGACCAAGACAAACTGC | 30 | GCATTTGAAATTACCCAACTCG | 42 |
| GRM3-10 Exon 4 | ACACAAATGGTGTTTGCTTGC | 31 | ATGTGTTGCCTGTTCTTGGC | 43 |

TABLE 6-continued

Primers used for PCR amplification of the GRM3 gene
(GRM3-CCDS accession 5600.1; Ref. Seq. accession NM_000840)

| Primer Exon | Forward Primer | SEQ ID NO: | Reverse Primer | SEQ ID NO: |
|---|---|---|---|---|
| GRM3-11 Exon 5 | CCATTGTATCCTTCATGCTATTACC | 32 | GACTGACCATGTCAGACCCTG | 44 |
| GRM3-12 Exon 1 | TCAGGAGTGAAGTTGGGTGT | 33 | CCCAGCCTCCATTAGTTCAC | 45 |

TABLE 7

Primers used for construction of the GRM3 gene

| Gene Name | Forward Primer | SEQ ID NO: | Reverse Primer | SEQ ID NO: |
|---|---|---|---|---|
| Cloning wild type GRM3 into pCDF1-MCS2-EF2-Puromycin/pcDNA3.1 | gctgtctagagccaccatgaagatgttgacaagactgcaagttct | 7 | atcagcggccgcctacttatcgtcgtcatccttgtaatccagagatgaggtggtggagtc | 12 |
| Site-directed mutational primer for inserting G561E | gcagacctaactgaatgctatgacctt | 8 | aaggtcatagcattcagttaggtctgc | 13 |
| Site-directed mutational primer for inserting S610L | ttggtcaaagcattgggccgagaactc | 9 | gagttctcggcccaatgctttgaccaa | 14 |
| Site-directed mutational primer for inserting E767K | gaaaatttcaacaaagctaagttcata | 10 | tatgaacttagctttgttgaaattttc | 15 |
| Site-directed mutational primer for inserting E870K | tgcaatgggcggaaagtcctcgactcc | 11 | ggagtcgaggactttccgcccattgca | 16 |

TABLE 8

BRAF and NRAS genotypes of cells used in the AZD-6244 inhibition study

| Tumor line | BRAF | NRAS |
|---|---|---|
| 68T (Ser154Phe/Asp280Asn/Arg352Trp/Glu870Lys) | MUT | WT |
| 63T (Glu573Lys) | WT | MUT |
| 29T (Splice site) | MUT | WT |
| 36T (Gly561Glu) | MUT | WT |
| 55T (WT) | WT | WT |
| 76T (Gly88Glu/Ser610Leu) | WT | WT |
| 39T (Glu517Lys) | WT | WT |
| 71T (WT) | MUT | WT |
| 49T (WT) | MUT | WT |
| 13T (WT) | WT | WT |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of diagnosing a subject as having melanoma, or susceptible to developing melanoma, comprising detecting the presence or absence of at least one mutation in the glutamate receptor, metabotropic 3 (GRM3) gene in a skin sample obtained from the subject, wherein the at least one mutation is selected from G1682A, C1829T, G2299A and G2608A (SEQ ID NO: 1), wherein the presence of the at least one mutation indicates the subject has melanoma or is susceptible to developing melanoma.

2. The method of claim 1, further comprising providing a test output to a user.

3. The method of claim 2, wherein the output comprises the presence or absence of the at least one mutation, a diagnosis, a treatment recommendation, or any combination thereof.

4. The method of claim 1, further comprising providing an appropriate therapy to the subject.

5. The method of claim 4, wherein the appropriate therapy is surgical removal of tumor tissue, radiation therapy, chemotherapy, administration of a GRM3 inhibitor, administration of an MEK inhibitor, or any combination of two or more thereof.

6. The method of claim 5, wherein the MEK inhibitor is AZD-6244.

7. A method of selecting a subject diagnosed with melanoma as a candidate for treatment with a GRM3 inhibitor, an MEK inhibitor, or both, comprising detecting the presence or absence of at least one mutation in the GRM3 gene in a melanoma sample obtained from the subject, wherein the mutation is selected from G1682A, C1829T, G2299A and G2608A (SEQ ID NO: 1), wherein the presence of the at least one mutation identifies the subject as a candidate for treatment with a GRM3 inhibitor, an MEK inhibitor, or both.

8. The method of claim 7, wherein the MEK inhibitor is AZD-6244.

9. The method of claim 7, further comprising providing a test output to a user.

10. The method of claim 9, wherein the output comprises the presence or absence of the at least one mutation, a diagnosis, a treatment recommendation, or any combination thereof.

11. The method of claim 1, wherein the at least one mutation is G1682A.

12. The method of claim 1, wherein the at least one mutation is C1829T.

13. The method of claim 1, wherein the at least one mutation is G2299A.

14. The method of claim 1, wherein the at least one mutation is G2608A.

15. The method of claim 7, wherein the at least one mutation is G1682A.

16. The method of claim 7, wherein the at least one mutation is C1829T.

17. The method of claim 7, wherein the at least one mutation is G2299A.

18. The method of claim 7, wherein the at least one mutation is G2608A.

19. The method of claim 1, wherein detecting the presence or absence of at least one mutation in the GRM3 gene comprises amplifying GRM3 nucleic acid from the skin sample using GRM3-specific primers, wherein the GRM3-specific primers comprise one or more of SEQ ID NOs: 22-45.

20. The method of claim 7, wherein detecting the presence or absence of at least one mutation in the GRM3 gene comprises amplifying GRM3 nucleic acid from the melanoma sample using GRM3-specific primers, wherein the GRM3-specific primers comprise one or more of SEQ ID NOs: 22-45.

* * * * *

SEQUENCE LISTING

<160> NUMBER OF SEQ ID NOS: 48

<210> SEQ ID NO 1
<211> LENGTH: 2640
<212> TYPE: DNA

<213> ORGANISM: Homo sapiens

<400> SEQUENCE: 1

| | | | | | |
|---|---|---|---|---|---|
| atgaagatgt | tgacaagact | gcaagttctt | accttagctt | tgttttcaaa | gggatttttta | 60 |
| ctctctttag | gggaccataa | ctttctaagg | agagagatta | aaatagaagg | tgaccttgtt | 120 |
| ttaggggcc | tgtttcctat | taacgaaaaa | ggcactggaa | ctgaagaatg | tgggcgaatc | 180 |
| aatgaagacc | gagggattca | acgcctggaa | gccatgttgt | ttgctattga | tgaaatcaac | 240 |
| aaagatgatt | acttgctacc | aggagtgaag | ttgggtgttc | acattttgga | tacatgttca | 300 |
| agggatacct | atgcattgga | gcaatcactg | gagtttgtca | gggcatcttt | gacaaaagtg | 360 |
| gatgaagctg | agtatatgtg | tcctgatgga | tcctatgcca | ttcaagaaaa | catcccactt | 420 |
| ctcattgcag | gggtcattgg | tggctcttat | agcagtgttt | ccatacaggt | ggcaaacctg | 480 |
| ctgcggctct | tccagatccc | tcagatcagc | tacgcatcca | ccagcgccaa | actcagtgat | 540 |
| aagtcgcgct | atgattactt | tgccaggacc | gtgcccccg | acttctacca | ggccaaagcc | 600 |
| atggctgaga | tcttgcgctt | cttcaactgg | acctacgtgt | ccacagtagc | ctccgagggt | 660 |
| gattacgggg | agacagggat | cgaggccttc | gagcaggaag | cccgcctgcg | caacatctgc | 720 |
| atcgctacgc | ggagaaggt | gggccgctcc | aacatccgca | gtcctacga | cagcgtgatc | 780 |
| cgagaactgt | tgcagaagcc | caacgcgcgc | gtcgtggtcc | tcttcatgcg | cagcgacgac | 840 |
| tcgcgggagc | tcattgcagc | cgccagccgc | gccaatgcct | ccttcacctg | ggtggccagc | 900 |
| gacggctggg | gcgcgcagga | gagcatcatc | aagggcagcg | agcatgtggc | ctacggcgcc | 960 |
| atcaccctgg | agctggcctc | ccagcctgtc | cgccagttcg | accgctactt | ccagagcctc | 1020 |
| aacccctaca | caaccaccg | caaccccctgg | ttccgggact | tctgggagca | aaagtttcag | 1080 |
| tgcagcctcc | agaacaaacg | caaccacagg | cgcgtctgcg | acaagcacct | ggccatcgac | 1140 |
| agcagcaact | acgagcaaga | gtccaagatc | atgtttgtgg | tgaacgcggt | gtatgccatg | 1200 |
| gcccacgctt | tgcacaaaat | gcagcgcacc | ctctgtccca | acactaccaa | gctttgtgat | 1260 |
| gctatgaaga | tcctggatgg | gaagaagttg | tacaaggatt | acttgctgaa | aatcaacttc | 1320 |
| acggctccat | tcaacccaaa | taaagatgca | gatagcatag | tcaagtttga | cacttttgga | 1380 |
| gatggaatgg | ggcgatacaa | cgtgttcaat | ttccaaaatg | taggtggaaa | gtattcctac | 1440 |
| ttgaaagttg | gtcactgggc | agaaacctta | tcgctagatg | tcaactctat | ccactggtcc | 1500 |
| cggaactcag | tccccacttc | ccagtgcagc | gaccctgtg | ccccaatga | aatgaagaat | 1560 |
| atgcaaccag | gggatgtctg | ctgctggatt | gcatcccct | gtgaaccta | cgaataccctg | 1620 |
| gctgatgagt | ttacctgtat | ggattgtggg | tctggacagt | ggcccactgc | agacctaact | 1680 |
| ggatgctatg | accttcctga | ggactacatc | aggtgggaag | acgcctgggc | cattggccca | 1740 |
| gtcaccattg | cctgtctggg | ttttatgtgt | acatgcatgg | ttgtaactgt | ttttatcaag | 1800 |
| cacaacaaca | cacccttggt | caaagcatcg | ggccagaac | tctgctacat | cttattgttt | 1860 |
| ggggttggcc | tgtcatactg | catgacattc | ttcttcattg | ccaagccatc | accagtcatc | 1920 |
| tgtgcattgc | gccgactcgg | gctggggagt | tccttcgcta | tctgttactc | agccctgctg | 1980 |
| accaagacaa | actgcattgc | ccgcatcttc | gatggggtca | agaatggcgc | tcagaggcca | 2040 |
| aaattcatca | gccccagttc | tcaggttttc | atctgcctgg | gtctgatcct | ggtgcaaatt | 2100 |
| gtgatggtgt | ctgtgtggct | catcctggag | gccccaggca | ccaggaggta | tacccttgca | 2160 |
| gagaagcggg | aaacagtcat | cctaaaatgc | aatgtcaaag | attccagcat | gttgatctct | 2220 |
| cttacctacg | atgtgatcct | ggtgatctta | tgcactgtgt | acgccttcaa | aacgcggaag | 2280 |

```
tgcccagaaa atttcaacga agctaagttc ataggttttα ccatgtacac cacgtgcatc   2340
atctggttgg ccttcctccc tatattttat gtgacatcaa gtgactacag agtgcagacg   2400
acaaccatgt gcatctctgt cagcctgagt ggctttgtgg tcttgggctg tttgtttgca   2460
cccaaggttc acatcatcct gtttcaaccc cagaagaatg ttgtcacaca cagactgcac   2520
ctcaacaggt tcagtgtcag tggaactggg accacatact ctcagtcctc tgcaagcacg   2580
tatgtgccaa cggtgtgcaa tgggcgggaa gtcctcgact ccaccacctc atctctgtga   2640
```

<210> SEQ ID NO 2
<211> LENGTH: 879
<212> TYPE: PRT
<213> ORGANISM: Homo sapiens

<400> SEQUENCE: 2

```
Met Lys Met Leu Thr Arg Leu Gln Val Leu Thr Leu Ala Leu Phe Ser
1               5                   10                  15

Lys Gly Phe Leu Leu Ser Leu Gly Asp His Asn Phe Leu Arg Arg Glu
                20                  25                  30

Ile Lys Ile Glu Gly Asp Leu Val Leu Gly Gly Leu Phe Pro Ile Asn
            35                  40                  45

Glu Lys Gly Thr Gly Thr Glu Glu Cys Gly Arg Ile Asn Glu Asp Arg
        50                  55                  60

Gly Ile Gln Arg Leu Glu Ala Met Leu Phe Ala Ile Asp Glu Ile Asn
65                  70                  75                  80

Lys Asp Asp Tyr Leu Leu Pro Gly Val Lys Leu Gly Val His Ile Leu
                85                  90                  95

Asp Thr Cys Ser Arg Asp Thr Tyr Ala Leu Glu Gln Ser Leu Glu Phe
            100                 105                 110

Val Arg Ala Ser Leu Thr Lys Val Asp Glu Ala Glu Tyr Met Cys Pro
        115                 120                 125

Asp Gly Ser Tyr Ala Ile Gln Glu Asn Ile Pro Leu Leu Ile Ala Gly
    130                 135                 140

Val Ile Gly Gly Ser Tyr Ser Ser Val Ser Ile Gln Val Ala Asn Leu
145                 150                 155                 160

Leu Arg Leu Phe Gln Ile Pro Gln Ile Ser Tyr Ala Ser Thr Ser Ala
                165                 170                 175

Lys Leu Ser Asp Lys Ser Arg Tyr Asp Tyr Phe Ala Arg Thr Val Pro
            180                 185                 190

Pro Asp Phe Tyr Gln Ala Lys Ala Met Ala Glu Ile Leu Arg Phe Phe
        195                 200                 205

Asn Trp Thr Tyr Val Ser Thr Val Ala Ser Glu Gly Asp Tyr Gly Glu
    210                 215                 220

Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
                245                 250                 255

Asp Ser Val Ile Arg Glu Leu Leu Gln Lys Pro Asn Ala Arg Val Val
            260                 265                 270

Val Leu Phe Met Arg Ser Asp Asp Ser Arg Glu Leu Ile Ala Ala Ala
        275                 280                 285

Ser Arg Ala Asn Ala Ser Phe Thr Trp Val Ala Ser Asp Gly Trp Gly
    290                 295                 300

Ala Gln Glu Ser Ile Ile Lys Gly Ser Glu His Val Ala Tyr Gly Ala
```

```
305                 310                 315                 320
Ile Thr Leu Glu Leu Ala Ser Gln Pro Val Arg Gln Phe Asp Arg Tyr
                325                 330                 335

Phe Gln Ser Leu Asn Pro Tyr Asn Asn His Arg Asn Pro Trp Phe Arg
                340                 345                 350

Asp Phe Trp Glu Gln Lys Phe Gln Cys Ser Leu Gln Asn Lys Arg Asn
                355                 360                 365

His Arg Arg Val Cys Asp Lys His Leu Ala Ile Asp Ser Ser Asn Tyr
        370                 375                 380

Glu Gln Glu Ser Lys Ile Met Phe Val Val Asn Ala Val Tyr Ala Met
385                 390                 395                 400

Ala His Ala Leu His Lys Met Gln Arg Thr Leu Cys Pro Asn Thr Thr
                405                 410                 415

Lys Leu Cys Asp Ala Met Lys Ile Leu Asp Gly Lys Lys Leu Tyr Lys
                420                 425                 430

Asp Tyr Leu Leu Lys Ile Asn Phe Thr Ala Pro Phe Asn Pro Asn Lys
            435                 440                 445

Asp Ala Asp Ser Ile Val Lys Phe Asp Thr Phe Gly Asp Gly Met Gly
        450                 455                 460

Arg Tyr Asn Val Phe Asn Phe Gln Asn Val Gly Gly Lys Tyr Ser Tyr
465                 470                 475                 480

Leu Lys Val Gly His Trp Ala Glu Thr Leu Ser Leu Asp Val Asn Ser
                485                 490                 495

Ile His Trp Ser Arg Asn Ser Val Pro Thr Ser Gln Cys Ser Asp Pro
                500                 505                 510

Cys Ala Pro Asn Glu Met Lys Asn Met Gln Pro Gly Asp Val Cys Cys
                515                 520                 525

Trp Ile Cys Ile Pro Cys Glu Pro Tyr Glu Tyr Leu Ala Asp Glu Phe
            530                 535                 540

Thr Cys Met Asp Cys Gly Ser Gly Gln Trp Pro Thr Ala Asp Leu Thr
545                 550                 555                 560

Gly Cys Tyr Asp Leu Pro Glu Asp Tyr Ile Arg Trp Glu Asp Ala Trp
                565                 570                 575

Ala Ile Gly Pro Val Thr Ile Ala Cys Leu Gly Phe Met Cys Thr Cys
            580                 585                 590

Met Val Val Thr Val Phe Ile Lys His Asn Asn Thr Pro Leu Val Lys
            595                 600                 605

Ala Ser Gly Arg Glu Leu Cys Tyr Ile Leu Leu Phe Gly Val Gly Leu
        610                 615                 620

Ser Tyr Cys Met Thr Phe Phe Phe Ile Ala Lys Pro Ser Pro Val Ile
625                 630                 635                 640

Cys Ala Leu Arg Arg Leu Gly Leu Gly Ser Ser Phe Ala Ile Cys Tyr
                645                 650                 655

Ser Ala Leu Leu Thr Lys Thr Asn Cys Ile Ala Arg Ile Phe Asp Gly
                660                 665                 670

Val Lys Asn Gly Ala Gln Arg Pro Lys Phe Ile Ser Pro Ser Ser Gln
            675                 680                 685

Val Phe Ile Cys Leu Gly Leu Ile Leu Val Gln Ile Val Met Val Ser
        690                 695                 700

Val Trp Leu Ile Leu Glu Ala Pro Gly Thr Arg Arg Tyr Thr Leu Ala
705                 710                 715                 720

Glu Lys Arg Glu Thr Val Ile Leu Lys Cys Asn Val Lys Asp Ser Ser
                725                 730                 735
```

```
Met Leu Ile Ser Leu Thr Tyr Asp Val Ile Leu Val Ile Leu Cys Thr
                740                 745                 750

Val Tyr Ala Phe Lys Thr Arg Lys Cys Pro Glu Asn Phe Asn Glu Ala
            755                 760                 765

Lys Phe Ile Gly Phe Thr Met Tyr Thr Thr Cys Ile Ile Trp Leu Ala
770                 775                 780

Phe Leu Pro Ile Phe Tyr Val Thr Ser Ser Asp Tyr Arg Val Gln Thr
785                 790                 795                 800

Thr Thr Met Cys Ile Ser Val Ser Leu Ser Gly Phe Val Val Leu Gly
                805                 810                 815

Cys Leu Phe Ala Pro Lys Val His Ile Ile Leu Phe Gln Pro Gln Lys
            820                 825                 830

Asn Val Val Thr His Arg Leu His Leu Asn Arg Phe Ser Val Ser Gly
                835                 840                 845

Thr Gly Thr Thr Tyr Ser Gln Ser Ser Ala Ser Thr Tyr Val Pro Thr
            850                 855                 860

Val Cys Asn Gly Arg Glu Val Leu Asp Ser Thr Thr Ser Ser Leu
865                 870                 875

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
ttgggtgttc acattttgga                                           20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
tcacgctgtc gtaggacttg                                           20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
tggaaggact catgaccaca                                           20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
tgctgtagcc aaattcgttg                                           20

<210> SEQ ID NO 7
<211> LENGTH: 45
```

```
<212> TYPE: DNA
<213> ORGANISM: Artificial Sequence
<220> FEATURE:
<223> OTHER INFORMATION: Synthetic polynucleotide

<400> SEQUENCE: 7
gctgtctaga gccaccatga agatgttgac aagactgcaa gttct              45

<210> SEQ ID NO 8
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 8
gcagacctaa ctgaatgcta tgacctt                                  27

<210> SEQ ID NO 9
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 9
ttggtcaaag cattgggccg agaactc                                  27

<210> SEQ ID NO 10
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 10
gaaaatttca acaaagctaa gttcata                                  27

<210> SEQ ID NO 11
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 11
tgcaatgggc ggaaagtcct cgactcc                                  27

<210> SEQ ID NO 12
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 12
atcagcggcc gcctacttat cgtcgtcatc cttgtaatcc agagatgagg tggtggagtc  60

<210> SEQ ID NO 13
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 13
```
aaggtcatag cattcagtta ggtctgc                                27

<210> SEQ ID NO 14
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 14
gagttctcgg cccaatgctt tgaccaa                                27

<210> SEQ ID NO 15
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 15
tatgaactta gctttgttga aattttc                                27

<210> SEQ ID NO 16
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 16
ggagtcgagg actttccgcc cattgca                                27

<210> SEQ ID NO 17
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 17
ccggcagaac atggaaataa ccattctcga gaatggttat ttccatgttc tgttttt      57

<210> SEQ ID NO 18
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 18
ccggcgaagc taagttcata ggtttctcga gaaacctatg aacttagctt cgttttt      57

<210> SEQ ID NO 19
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 19
ccgggcctgt ttcctattaa cgaaactcga gtttcgttaa taggaaacag gctttt       57

<210> SEQ ID NO 20
<211> LENGTH: 57
<212> TYPE: DNA
<213> ORGANISM: Artificial Sequence

```
<220> FEATURE:
<223> OTHER INFORMATION: Synthetic polynucleotide

<400> SEQUENCE: 20
ccgggcagat agcatagtca agtttctcga gaaacttgac tatgctatct gctttttt        57

<210> SEQ ID NO 21
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 21
ccggcctgtc atactgcatg acattctcga gaatgtcatg cagtatgaca ggttttt        57

<210> SEQ ID NO 22
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 22
ctagcatgac acattggctc c                                                21

<210> SEQ ID NO 23
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 23
agagagtgtg gtgcccttct c                                                21

<210> SEQ ID NO 24
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 24
gctgagatct tgcgcttctt c                                                21

<210> SEQ ID NO 25
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 25
gtgatccgag aactgttgca g                                                21

<210> SEQ ID NO 26
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 26
gttcgaccgc tacttccaga g                                                21
```

```
<210> SEQ ID NO 27
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 27
ccttggaatc accatttcct g                                          21

<210> SEQ ID NO 28
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 28
cttgaaagtt ggtcactggg c                                          21

<210> SEQ ID NO 29
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 29
aagcacaaca acacaccctt g                                          21

<210> SEQ ID NO 30
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 30
ctgctgacca agacaaactg c                                          21

<210> SEQ ID NO 31
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 31
acacaaatgg tgtttgcttg c                                          21

<210> SEQ ID NO 32
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 32
ccattgtatc cttcatgcta ttacc                                      25

<210> SEQ ID NO 33
<211> LENGTH: 20
<212> TYPE: DNA
<213> ORGANISM: Artificial Sequence
<220> FEATURE:
<223> OTHER INFORMATION: Synthetic polynucleotide
```

<400> SEQUENCE: 33
tcaggagtga agttgggtgt                                                       20

<210> SEQ ID NO 34
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 34
aatggcatag gatccatcag g                                                     21

<210> SEQ ID NO 35
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 35
ctgcaacagt tctcggatca c                                                     21

<210> SEQ ID NO 36
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 36
tggactcttg ctcgtagttg c                                                     21

<210> SEQ ID NO 37
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 37
tttaaaggct cttggcttac cc                                                    22

<210> SEQ ID NO 38
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 38
gcacagaggc atttgattcc                                                       20

<210> SEQ ID NO 39
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 39
ccagacccac aatccataca g                                                     21

<210> SEQ ID NO 40

```
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 40
gcaatgcagt ttgtcttggt c                                              21

<210> SEQ ID NO 41
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 41
gatgcacgtg gtgtacatgg                                                20

<210> SEQ ID NO 42
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 42
gcatttgaaa ttacccaact cg                                             22

<210> SEQ ID NO 43
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 43
atgtgttgcc tgttcttggc                                                20

<210> SEQ ID NO 44
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 44
gactgaccat gtcagaccct g                                              21

<210> SEQ ID NO 45
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 45
cccagcctcc attagttcac                                                20

<210> SEQ ID NO 46
<211> LENGTH: 97
<212> TYPE: DNA
<213> ORGANISM: Artificial Sequence
<220> FEATURE:
<223> OTHER INFORMATION: Synthetic polynucleotide

<400> SEQUENCE: 46
```

```
tgctgttgac agtgagcgcc ggctccattc aacccaaata tagtgaagcc acagatgtat    60
atttgggttg aatggagccg ttgcctactg cctcgga                             97

<210> SEQ ID NO 47
<211> LENGTH: 97
<212> TYPE: DNA
<213> ORGANISM: Artificial Sequence
<220> FEATURE:
<223> OTHER INFORMATION: Synthetic polynucleotide

<400> SEQUENCE: 47
tgctgttgac agtgagcgcc cgcttcttca actggaccta tagtgaagcc acagatgtat    60
aggtccagtt gaagaagcgg atgcctactg cctcgga                             97

<210> SEQ ID NO 48
<211> LENGTH: 4260
<212> TYPE: DNA
<213> ORGANISM: Homo sapiens

<400> SEQUENCE: 48
gtgcagttga gtcgcgagta cggctgagct gcgtaccggc ctccctggct ctcacactcc    60
ctctctgctc ccgctctcct aatctcctct ggcatgcggt cagcccctg cccagggacc    120 acaggagagt tcttgtaagg actgttagtc cctgcttacc tgaaagccaa gcgctctagc    180
agagctttaa agttggagcc gccaccctcc ctaccgcccc atgccccttc accccactcc    240
gaaattcacc gacctttgca tgcactgcct aaggatttca gagtgaggca aagcagtcgg    300
caaatctacc ctggctttc gtataaaaat cctctcgtct aggtaccctg gctcactgaa    360
gactctgcag atatacccctt ataagaggga gggtgggga gggaaaagaa cgagagaggg    420
aggaaagaat gaaaggaga ggatgccagg aggtccgtgc ttctgccaag agtcccaatt    480
agatgcgacg gcttcagcct ggtcaaggtg aaggaaagtt gcttccgcgc ctaggaagtg    540
ggtttgcctg ataagagaag gaggaggga ctcggctggg aagagctccc ctcccctccg    600
cggaagacca ctgggtcccc tctttcccca acctcctccc tctcttctac tccaccctc    660 cgttttccca ctccccactg actcggatgc ctggatgttc tgccaccggg cagtggtcca    720
gcgtgcagcc gggagggggc aggggcaggg ggcactgtga caggaagctg cgcgcacaag    780
ttggccattt cgagggcaaa ataagttctc ccttggattt ggaaaggaca aagccagtaa    840
gctacctctt ttgtgtcgga tgaggaggac caaccatgag ccagagcccg ggtgcaggct    900
caccgccgcc gctgccaccg cggtcagctc cagttcctgc caggagttgt cggtgcgagg    960
aattttgtga caggctctgt tagtctgttc ctcccttatt tgaaggacag gccaaagatc   1020
cagtttggaa atgagagagg actagcatga cacattggct ccaccattga tatctcccag   1080
aggtacagaa acaggattca tgaagatgtt gacaagactg caagttctta ccttagcttt   1140
gttttcaaag ggattttttac tctctttagg ggaccataac tttctaagga gagagattaa   1200
aatagaaggt gaccttgttt tagggggcct gtttcctatt aacgaaaaag gcactggaac   1260
tgaagaatgt gggcgaatca atgaagaccg agggattcaa cgcctggaag ccatgttgtt   1320
tgctattgat gaaatcaaca agatgattta cttgctacca ggagtgaagt tgggtgttca   1380
cattttggat acatgttcaa gggataccta tgcattggag caatcactgg agtttgtcag   1440
ggcatctttg acaaaagtgg atgaagctga gtatatgtgt cctgatggat cctatgccat   1500
tcaagaaaac atcccacttc tcattgcagg ggtcattggt ggctcttata gcagtgtttc   1560
```

```
catacaggtg gcaaacctgc tgcggctctt ccagatccct cagatcagct acgcatccac    1620
cagcgccaaa ctcagtgata agtcgcgcta tgattacttt gccaggaccg tgcccccga     1680 cttctaccag gccaaagcca tggctgagat cttgcgcttc ttcaactgga cctacgtgtc    1740
cacagtagcc tccgagggtg attacgggga gacagggatc gaggccttcg agcaggaagc    1800
ccgcctgcgc aacatctgca tcgctacggc ggagaaggtg ggccgctcca acatccgcaa    1860
gtcctacgac agcgtgatcc gagaactgtt gcagaagccc aacgcgcgcg tcgtggtcct    1920
cttcatgcgc agcgacgact cgcgggagct cattgcagcc gccagccgcg ccaatgcctc    1980
cttcacctgg gtggccagcg acggctgggg cgcgcaggag agcatcatca agggcagcga    2040
gcatgtggcc tacggcgcca tcaccctgga gctggcctcc cagcctgtcc gccagttcga    2100
ccgctacttc cagagcctca acccctacaa caaccaccgc aaccctggt tccgggactt     2160 ctgggagcaa aagtttcagt gcagcctcca gaacaaacgc aaccacaggc gcgtctgcga    2220
caagcacctg gccatcgaca gcagcaacta cgagcaagag tccaagatca tgtttgtggt    2280
gaacgcggtg tatgccatgg cccacgcttt gcacaaaatg cagcgcaccc tctgtcccaa    2340
cactaccaag ctttgtgatg ctatgaagat cctggatggg aagaagttgt acaaggatta    2400
cttgctgaaa atcaacttca cggctccatt caacccaaat aaagatgcag atagcatagt    2460
caagtttgac acttttggag atggaatggg gcgatacaac gtgttcaatt ccaaaatgt     2520 aggtggaaag tattcctact tgaaagttgg tcactgggca gaaaccttat cgctagatgt    2580
caactctatc cactggtccc ggaactcagt ccccacttcc cagtgcagcg acccctgtgc    2640
ccccaatgaa atgaagaata tgcaaccagg ggatgtctgc tgctggattt gcatcccctg    2700
tgaaccctac gaatacctgg ctgatgagtt tacctgtatg gattgtgggt ctggacagtg    2760
gcccactgca gacctaactg gatgctatga ccttcctgag gactacatca ggtgggaaga    2820
cgcctgggcc attggcccag tcaccattgc ctgtctgggt tttatgtgta catgcatggt    2880
tgtaactgtt tttatcaagc acaacaacac acccttggtc aaagcatcgg ccgagaact     2940 ctgctacatc ttattgtttg gggttggcct gtcatactgc atgacattct tcttcattgc    3000
caagccatca ccagtcatct gtgcattgcg ccgactcggg ctggggagtt ccttcgctat    3060
ctgttactca gccctgctga ccaagacaaa ctgcattgcc cgcatcttcg atggggtcaa    3120
gaatggcgct cagaggccaa aattcatcag ccccagttct caggttttca tctgcctggg    3180
tctgatcctg gtgcaaattg tgatggtgtc tgtgtggctc atcctggagg ccccaggcac    3240
caggaggtat accccttgcag agaagcggga aacagtcatc ctaaaatgca atgtcaaaga    3300
ttccagcatg ttgatctctc ttacctacga tgtgatcctg gtgatcttat gcactgtgta    3360
cgccttcaaa acgcggaagt gcccagaaaa tttcaacgaa gctaagttca taggttttac    3420
catgtacacc acgtgcatca tctggttggc cttcctccct atattttatg tgacatcaag    3480
tgactacaga gtgcagacga caaccatgtg catctctgtc agcctgagtg gctttgtggt    3540
cttgggctgt ttgtttgcac ccaaggttca catcatcctg tttcaacccc agaagaatgt    3600
tgtcacacac agactgcacc tcaacaggtt cagtgtcagt ggaactggga ccacatactc    3660
tcagtcctct gcaagcacgt atgtgccaac ggtgtgcaat gggcgggaag tcctcgactc    3720
caccacctca tctctgtgat tgtgaattgc agttcagttc ttgtgttttt agactgttag    3780
acaaaagtgc tcacgtgcag ctccagaata tggaaacaga gcaaaagaac aaccctagta    3840
ccttttttta gaaacagtac gataaattat ttttgaggac tgtatatagt gatgtgctag    3900
aactttctag gctgagtcta gtgccctat tattaacaat tcccccagaa catggaaata    3960
```

```
accattgttt acagagctga gcattggtga cagggtctga catggtcagt ctactaaaaa    4020
acaaaaaaaa aaaacaaaaa aaaaaaaaca aaagaaaaaa ataaaaatac ggtggcaata    4080
ttatgtaacc tttttttccta tgaagttttt tgtaggtcct tgttgtaact aatttaggat   4140
gagtttctat gttgtatatt aaagttacat tatgtgtaac agattgattt tctcagcaca    4200
aaataaaaag catctgtatt aatgtaaaga tactgagaat aaaaccttca aggttttcca    4260
```